(12) United States Patent
Moskowitz et al.

(10) Patent No.: US 11,965,178 B2
(45) Date of Patent: Apr. 23, 2024

(54) PLATELETS LOADED WITH ANTI-CANCER AGENTS

(71) Applicant: Cellphire, Inc., Rockville, MD (US)

(72) Inventors: Keith Andrew Moskowitz, Westfield, IN (US); Rafael Jorda, Merignac (FR); Ying Yi Zheng, Rockville, MD (US); Daniel Allen Sheik, West Lafayette, IN (US)

(73) Assignee: Cellphire, Inc., Rockville, MD (US)

( * ) Notice: Subject to any disclaimer, the term of this patent is extended or adjusted under 35 U.S.C. 154(b) by 599 days.

(21) Appl. No.: 16/698,645

(22) Filed: Nov. 27, 2019

(65) Prior Publication Data

US 2020/0206143 A1 Jul. 2, 2020

Related U.S. Application Data

(60) Provisional application No. 62/828,041, filed on Apr. 2, 2019, provisional application No. 62/775,141, filed on Dec. 4, 2018, provisional application No. 62/773,931, filed on Nov. 30, 2018.

(51) Int. Cl.

| | | |
|---|---|---|
| *C12N 5/078* | (2010.01) | |
| *A01N 1/02* | (2006.01) | |
| *A61K 9/127* | (2006.01) | |
| *A61K 9/50* | (2006.01) | |
| *A61K 31/337* | (2006.01) | |
| *A61K 31/502* | (2006.01) | |
| *A61K 31/704* | (2006.01) | |
| *A61K 35/19* | (2015.01) | |

(52) U.S. Cl.
CPC ........... *C12N 5/0644* (2013.01); *A01N 1/021* (2013.01); *A01N 1/0221* (2013.01); *A01N 1/0226* (2013.01); *A01N 1/0284* (2013.01); *A61K 9/1271* (2013.01); *A61K 9/5068* (2013.01); *A61K 31/337* (2013.01); *A61K 31/502* (2013.01); *A61K 31/704* (2013.01); *A61K 35/19* (2013.01); *C12N 2501/02* (2013.01); *C12N 2501/998* (2013.01); *C12N 2501/999* (2013.01); *C12N 2529/00* (2013.01)

(58) Field of Classification Search
CPC .............. C12N 5/0644; C12N 2501/02; C12N 2501/998; C12N 2501/999; C12N 2529/00; A01N 1/0221; A01N 1/0284; A01N 1/21; A01N 1/0226; A61K 35/19; A61K 9/1271; A61K 9/5068; A61K 31/337; A61K 31/502; A61K 31/704

See application file for complete search history.

(56) References Cited

U.S. PATENT DOCUMENTS

| | | |
|---|---|---|
| 3,928,566 A | 12/1975 | Briggs et al. |
| 3,932,943 A | 1/1976 | Briggs et al. |
| 4,059,967 A | 11/1977 | Rowe et al. |
| 4,157,383 A | 6/1979 | Sedlacek et al. |
| 4,455,299 A | 6/1984 | Grode |
| 4,481,189 A | 11/1984 | Prince |
| 4,670,013 A | 6/1987 | Barnes et al. |
| 4,865,871 A | 9/1989 | Livesey et al. |
| 4,994,367 A | 2/1991 | Bode |
| 5,059,518 A | 10/1991 | Kortright et al. |
| 5,213,814 A | 5/1993 | Goodrich |
| 5,332,578 A | 7/1994 | Chao |
| 5,364,756 A | 11/1994 | Livesey et al. |
| 5,423,738 A | 6/1995 | Robinson |
| 5,571,801 A | 11/1996 | Segall |
| 5,622,867 A | 4/1997 | Livesy |
| 5,656,498 A | 8/1997 | Iijima |
| 5,656,598 A | 8/1997 | Dunstan et al. |
| 5,723,281 A | 3/1998 | Segall et al. |
| 5,736,313 A | 4/1998 | Spargo |
| 5,759,542 A * | 6/1998 | Gurewich ...... C12Y 304/21073 435/212 |
| 5,800,978 A | 9/1998 | Goodrich |
| 5,817,381 A | 10/1998 | Chen |
| 5,827,741 A | 10/1998 | Beattie |
| 5,919,614 A | 7/1999 | Livesey |
| 5,958,670 A | 9/1999 | Goodrich |
| 5,993,804 A | 11/1999 | Read |
| 6,127,111 A | 10/2000 | Braun |
| 6,211,575 B1 | 4/2001 | Hansford |
| 6,221,575 B1 | 4/2001 | Roser |
| 6,372,423 B1 | 4/2002 | Braun |
| 6,596,296 B1 | 7/2003 | Nelson |
| 6,653,062 B1 | 11/2003 | DePablo |
| 6,723,497 B2 | 4/2004 | Wolkers |

(Continued)

FOREIGN PATENT DOCUMENTS

| | | |
|---|---|---|
| CA | 1261259 A | 9/1989 |
| CA | 2097063 C | 6/1992 |

(Continued)

OTHER PUBLICATIONS

Mullin et al.(Veterinary and Comparative Oncology (2014)).*
Xu et al. (scientific Reports ; 7:42632 (2017).*
Read et al. Proc Natl Acad Sci 92(2): (1985).*
"Cryoprotein." The American Heritage® Stedman's Medical Dictionary. Houghton Mifflin Company. Mar. 24, 2010. <Dictionary.com http://dictionary.reference.com/browse/cryoprotein>.
"Expose", http://dictionary.reference.com/browse/expose, accessed Jul. 18, 2009.
"Platelet." The American Heritage® Dictionary of the English Language, Fourth Edition. Houghton Mifflin Company, 2004. Mar. 23, 2010. <Dictionary.com http://dictionary.reference.com/browse/platelet>.

(Continued)

*Primary Examiner* — Shirley V Gembeh
(74) *Attorney, Agent, or Firm* — Double Helix Law; Emanuel Vacchiano

(57) ABSTRACT

In some embodiments provided herein is a method of preparing cargo-loaded platelets, comprising: treating platelets with a cargo and with a loading buffer comprising a salt, a base, a loading agent, and optionally ethanol, to form the cargo-loaded platelets.

15 Claims, 20 Drawing Sheets

(56) References Cited

U.S. PATENT DOCUMENTS

| | | |
|---|---|---|
| 6,770,478 B2 | 8/2004 | Crowe |
| 6,833,236 B1 | 12/2004 | Stienstra |
| 6,858,222 B2 | 2/2005 | Nelson |
| 7,033,603 B2 | 4/2006 | Nelson |
| 7,169,606 B2 | 1/2007 | DePablo |
| 7,514,095 B2 | 4/2009 | Nelson |
| 7,811,558 B2 | 10/2010 | Ho |
| 8,097,403 B2 | 1/2012 | Ho |
| 8,486,617 B2 | 7/2013 | Ho |
| 8,486,619 B2 | 7/2013 | Miller |
| 8,529,961 B2 | 9/2013 | Campbell |
| 8,877,060 B2 | 11/2014 | Sehal |
| 8,900,209 B2 | 12/2014 | Rosati |
| 9,402,866 B2 | 8/2016 | Radwanski et al. |
| 9,545,379 B2 | 1/2017 | Liu et al. |
| 9,863,699 B2 | 1/2018 | Corbin et al. |
| 9,878,011 B2 | 1/2018 | Landrigan et al. |
| 9,950,035 B2 | 4/2018 | Binder et al. |
| 10,400,017 B2 | 9/2019 | Higgins et al. |
| 10,441,634 B2 | 10/2019 | Landrigan et al. |
| 10,539,367 B2 | 1/2020 | Corbin et al. |
| 10,793,327 B2 | 10/2020 | Weimer et al. |
| 10,843,100 B2 | 11/2020 | Khan et al. |
| 10,969,171 B2 | 4/2021 | Corbin et al. |
| 10,976,105 B2 | 4/2021 | Corbin et al. |
| 11,052,045 B2 | 7/2021 | Liu et al. |
| 11,529,587 B2 | 12/2022 | Montgomery et al. |
| 11,701,388 B2 | 7/2023 | Moskowitz et al. |
| 11,752,468 B2 | 9/2023 | Montgomery et al. |
| 11,767,511 B2 | 9/2023 | Moskowitz et al. |
| 2001/0019819 A1 | 9/2001 | Wolkers et al. |
| 2001/0028880 A1 | 10/2001 | Fisher |
| 2001/0046487 A1 | 11/2001 | Roser et al. |
| 2002/0009500 A1 | 1/2002 | Wolkers et al. |
| 2002/0076445 A1 | 6/2002 | Crowe |
| 2003/0022333 A1 | 1/2003 | Bronshtein |
| 2003/0073238 A1 | 4/2003 | Dzekunov et al. |
| 2003/0148449 A1 | 8/2003 | Kuliopulos et al. |
| 2003/0157475 A1 | 8/2003 | Schenk |
| 2004/0136974 A1 | 7/2004 | Crowe et al. |
| 2004/0147024 A1 | 7/2004 | Crowe |
| 2004/0152964 A1 | 8/2004 | Crowe |
| 2004/0185524 A1 | 9/2004 | Crowe |
| 2004/0265293 A1 | 12/2004 | Crowe et al. |
| 2005/0028559 A1 | 2/2005 | Hiromatsu |
| 2005/0048460 A1 | 3/2005 | Crowe |
| 2005/0074402 A1 | 4/2005 | Cagnolini |
| 2005/0181978 A1 | 8/2005 | Rojkjaer et al. |
| 2005/0191286 A1 | 9/2005 | Gandy |
| 2005/0222029 A1 | 10/2005 | Bartel et al. |
| 2006/0034809 A1 | 2/2006 | Ho et al. |
| 2006/0035383 A1 | 2/2006 | Ho |
| 2006/0051731 A1 | 3/2006 | Ho |
| 2006/0223050 A1 | 10/2006 | Crowe et al. |
| 2007/0087061 A1 | 4/2007 | Drake |
| 2007/0166389 A1 | 7/2007 | Bakaltcheva |
| 2007/0178104 A1 | 8/2007 | Awdalla |
| 2007/0243137 A1 | 10/2007 | Hainfeld |
| 2007/0243178 A1* | 10/2007 | Ho .................. A01N 1/0284 |
| | | 435/1.3 |
| 2007/0248612 A1 | 10/2007 | Wilson |
| 2007/0249047 A1 | 10/2007 | McKenna, Jr. |
| 2008/0064628 A1 | 3/2008 | Goodall et al. |
| 2008/0145834 A1 | 6/2008 | Ho et al. |
| 2008/0286366 A1 | 11/2008 | Fischer et al. |
| 2008/0299212 A1 | 12/2008 | Kim |
| 2009/0035289 A1* | 2/2009 | Wagner .................. A61K 35/16 |
| | | 435/325 |
| 2009/0111118 A1 | 4/2009 | Mylvaganam et al. |
| 2009/0175905 A1 | 7/2009 | Tseng et al. |
| 2009/0299212 A1 | 12/2009 | Principe et al. |
| 2010/0055067 A1 | 3/2010 | Park |
| 2010/0135969 A1 | 6/2010 | Mishra |
| 2010/0159023 A1 | 6/2010 | Bjornstrup et al. |
| 2010/0190717 A1 | 7/2010 | Bevec |
| 2010/0196461 A1 | 8/2010 | Simpkins |
| 2010/0267928 A1 | 10/2010 | Heckl |
| 2010/0273141 A1 | 10/2010 | Bakaltcheva et al. |
| 2011/0008804 A1 | 1/2011 | Kain et al. |
| 2011/0027257 A1 | 2/2011 | Burnouf |
| 2011/0183311 A1 | 7/2011 | Ho |
| 2011/0189151 A1 | 8/2011 | Stossel et al. |
| 2012/0009221 A1 | 1/2012 | Hoerr et al. |
| 2012/0028236 A1 | 2/2012 | Sehgal |
| 2012/0095085 A1 | 4/2012 | Layzer et al. |
| 2012/0100522 A1 | 4/2012 | Saghbini et al. |
| 2012/0141434 A1 | 6/2012 | Peled et al. |
| 2012/0156306 A1 | 6/2012 | Weissman et al. |
| 2012/0264815 A1 | 10/2012 | Sullenger et al. |
| 2012/0276581 A1 | 11/2012 | Arav et al. |
| 2012/0321722 A1 | 12/2012 | Liu |
| 2013/0059380 A1 | 3/2013 | Ho et al. |
| 2013/0061849 A1 | 3/2013 | Lemper |
| 2013/0122107 A1 | 5/2013 | Bakaltcheva |
| 2013/0195959 A1 | 8/2013 | Patel |
| 2013/0210903 A1 | 8/2013 | Sullenger et al. |
| 2014/0037750 A1 | 2/2014 | Radwanski et al. |
| 2014/0065120 A1 | 3/2014 | Nichols |
| 2014/0329323 A1 | 11/2014 | Nygaard et al. |
| 2014/0330226 A1 | 11/2014 | Coffey |
| 2014/0356948 A1 | 12/2014 | Jeon et al. |
| 2015/0064259 A1 | 3/2015 | Simpkins et al. |
| 2015/0306212 A1 | 10/2015 | Kahvejian et al. |
| 2015/0313943 A1 | 11/2015 | Kishikawa et al. |
| 2015/0313944 A1* | 11/2015 | Feng .................. A61P 17/02 |
| | | 435/372 |
| 2015/0361453 A1 | 12/2015 | Gresele et al. |
| 2016/0082044 A1 | 3/2016 | Liu et al. |
| 2016/0206783 A1 | 7/2016 | Dietz |
| 2016/0219870 A1 | 8/2016 | Wang et al. |
| 2016/0231338 A1 | 8/2016 | Aster et al. |
| 2016/0235781 A1 | 8/2016 | Emanuele |
| 2016/0324897 A1 | 11/2016 | Ingber et al. |
| 2017/0198335 A1 | 7/2017 | Muller |
| 2017/0274012 A1 | 9/2017 | Bode et al. |
| 2017/0333593 A1 | 11/2017 | Willard |
| 2018/0009874 A1 | 1/2018 | Wilcox et al. |
| 2018/0070581 A1 | 3/2018 | Tarrand et al. |
| 2018/0092348 A1 | 4/2018 | She et al. |
| 2018/0169027 A1 | 6/2018 | Zhang et al. |
| 2018/0169139 A1 | 6/2018 | Feuerstein |
| 2018/0235894 A1 | 8/2018 | Gu et al. |
| 2018/0311176 A1 | 11/2018 | Ozsolak |
| 2018/0312903 A1 | 11/2018 | Grölz |
| 2019/0008143 A1 | 1/2019 | Dee |
| 2019/0076478 A1 | 3/2019 | Hale |
| 2019/0192564 A1 | 6/2019 | Hijazi et al. |
| 2020/0046771 A1 | 2/2020 | Kuhn et al. |
| 2020/0060262 A1 | 2/2020 | Stolla |
| 2020/0076455 A1 | 3/2020 | Sharf |
| 2020/0078407 A1 | 3/2020 | Bhattacharya et al. |
| 2020/0093853 A1 | 3/2020 | Feuerstein |
| 2020/0208109 A1 | 7/2020 | Moskowitz et al. |
| 2020/0208110 A1 | 7/2020 | Lee et al. |
| 2020/0224164 A1 | 7/2020 | Moskowitz et al. |
| 2020/0281980 A1 | 9/2020 | Willard et al. |
| 2020/0291356 A1 | 9/2020 | Jorda et al. |
| 2020/0346167 A1 | 11/2020 | Montgomery et al. |
| 2021/0046120 A1 | 2/2021 | Moskowitz et al. |
| 2021/0046121 A1 | 2/2021 | Moskowitz et al. |
| 2021/0069240 A1 | 3/2021 | Jorda et al. |
| 2021/0100846 A1 | 4/2021 | Lee et al. |
| 2021/0180016 A1 | 6/2021 | Moskowitz et al. |
| 2021/0189341 A1 | 6/2021 | Sheik et al. |
| 2021/0299179 A1 | 9/2021 | Moskowitz et al. |
| 2021/0308066 A1 | 10/2021 | Moskowitz et al. |
| 2021/0308185 A1 | 10/2021 | Moskowitz et al. |
| 2021/0315935 A1 | 10/2021 | Moskowitz et al. |
| 2021/0353680 A1 | 11/2021 | Bhattacharya et al. |
| 2021/0368782 A1 | 12/2021 | Dee et al. |
| 2022/0168353 A1 | 6/2022 | Moskowitz et al. |
| 2022/0211029 A1 | 7/2022 | Moskowitz et al. |
| 2022/0273724 A1 | 9/2022 | Moskowitz et al. |
| 2022/0279777 A1 | 9/2022 | Moskowitz et al. |

(56) References Cited

U.S. PATENT DOCUMENTS

| | | |
|---|---|---|
| 2023/0112136 A1 | 4/2023 | Jorda et al. |
| 2023/0149467 A1 | 5/2023 | Montgomery et al. |
| 2023/0149468 A1 | 5/2023 | Antebi et al. |
| 2023/0158455 A1 | 5/2023 | Montgomery et al. |
| 2023/0226493 A1 | 7/2023 | Montgomery |
| 2023/0248771 A1 | 8/2023 | Moskowitz et al. |
| 2023/0248772 A1 | 8/2023 | Willard |
| 2023/0285465 A1 | 9/2023 | Moskowitz et al. |
| 2023/0346839 A1 | 11/2023 | Bhattacharya et al. |
| 2023/0356150 A1 | 11/2023 | Montgomery et al. |

FOREIGN PATENT DOCUMENTS

| | | |
|---|---|---|
| CA | 2136848 A1 | 12/1993 |
| CA | 2393315 A1 | 6/2001 |
| CA | 2840568 A1 | 1/2013 |
| CA | 3053041 A1 | 2/2020 |
| CN | 103524613 | 1/2014 |
| CN | 103907595 | 7/2014 |
| CN | 108715834 A | 10/2018 |
| CN | 109942687 A | 6/2019 |
| EP | 0397890 A1 | 11/1990 |
| EP | 0967862 | 1/2003 |
| EP | 0967862 B1 | 1/2003 |
| EP | 1374890 A2 | 1/2004 |
| EP | 1652538 | 5/2006 |
| EP | 1784639 A2 | 5/2007 |
| EP | 3307283 B1 | 12/2018 |
| EP | 3681518 A1 | 7/2020 |
| EP | 3551198 B1 | 2/2022 |
| JP | H08109136 | 4/1996 |
| JP | 2005053841 | 3/2005 |
| JP | 2012143554 A | 8/2012 |
| WO | WO 1990/005461 | 5/1990 |
| WO | 9012581 A1 | 11/1990 |
| WO | 1991017655 A1 | 11/1991 |
| WO | WO 1992008349 | 5/1992 |
| WO | WO 1993000806 | 1/1993 |
| WO | 1993023997 A1 | 12/1993 |
| WO | 9428950 A1 | 12/1994 |
| WO | 1998034478 A1 | 8/1998 |
| WO | 1999055346 A1 | 11/1999 |
| WO | 2001007921 A2 | 2/2001 |
| WO | 2001058266 A1 | 8/2001 |
| WO | 2003014305 A2 | 2/2003 |
| WO | 2003039582 A1 | 5/2003 |
| WO | 2003090839 A1 | 11/2003 |
| WO | WO 2004050896 | 6/2004 |
| WO | 2004078187 A1 | 9/2004 |
| WO | 2005002499 A2 | 1/2005 |
| WO | 2005020893 A2 | 3/2005 |
| WO | 2005021706 A2 | 3/2005 |
| WO | WO 2005077299 | 8/2005 |
| WO | 2005002499 A3 | 11/2005 |
| WO | WO 2006020773 | 2/2006 |
| WO | 2006059329 A1 | 6/2006 |
| WO | 2004050896 A3 | 12/2006 |
| WO | 2006020773 A3 | 7/2007 |
| WO | 2010046949 A1 | 4/2010 |
| WO | 2011020107 A2 | 2/2011 |
| WO | WO 2011020107 | 2/2011 |
| WO | 2012018484 A2 | 4/2012 |
| WO | 2012074637 A2 | 7/2012 |
| WO | 2014051537 A1 | 4/2014 |
| WO | WO 2014055949 | 4/2014 |
| WO | 2014066142 A1 | 5/2014 |
| WO | WO 2014118817 | 8/2014 |
| WO | 2015073587 A2 | 5/2015 |
| WO | 2015191632 A1 | 12/2015 |
| WO | WO 2016014854 | 1/2016 |
| WO | WO 2016057041 | 4/2016 |
| WO | 2016077682 A1 | 5/2016 |
| WO | 2016141325 A1 | 9/2016 |
| WO | 2016205144 A1 | 12/2016 |
| WO | WO 2016201081 | 12/2016 |
| WO | WO 2017040238 | * 3/2017 |
| WO | 2017123539 A1 | 7/2017 |
| WO | WO 2018106250 | 6/2018 |
| WO | 2019055683 A1 | 3/2019 |
| WO | WO 2020023905 | 1/2020 |
| WO | 2020056009 A1 | 3/2020 |
| WO | WO 2020112963 | 6/2020 |
| WO | WO 2020113035 | 6/2020 |
| WO | WO 2020113090 | 6/2020 |
| WO | WO 2020113101 | 6/2020 |
| WO | 2020165152 A1 | 8/2020 |
| WO | 2020186193 A1 | 9/2020 |
| WO | 2020227149 A1 | 11/2020 |
| WO | 2021011857 A1 | 1/2021 |
| WO | 2021034716 A1 | 2/2021 |
| WO | 2021034719 A1 | 2/2021 |
| WO | 2021046409 A1 | 3/2021 |
| WO | 2021108538 A1 | 6/2021 |
| WO | 2021108539 A1 | 6/2021 |
| WO | 2021158622 A1 | 8/2021 |
| WO | 2021158625 A1 | 8/2021 |
| WO | 2021158641 A1 | 8/2021 |
| WO | 2021158645 A1 | 8/2021 |
| WO | 2021158646 A1 | 8/2021 |
| WO | 2021232015 A1 | 11/2021 |
| WO | 2022103861 A1 | 5/2022 |
| WO | 2022178177 A1 | 8/2022 |
| WO | 2022178191 A1 | 8/2022 |
| WO | 2022178177 A4 | 10/2022 |
| WO | 2023081804 A1 | 5/2023 |

OTHER PUBLICATIONS

"Rounding". Dictionary.com. Dictionary.com Unabridged (v 1.1 ). Random House, Inc. http://dictionary.reference.com/browse/rounding (accessed: Oct. 27, 2008).

Adams, ed., Ducry, et al., "The principles of freeze-drying," DNA Repair Protocols, Methods in Molecular Biology, Humana Press, US, 2007, Chapter 2, 368:15-38.

Agam et al. "Passive Participation of Fixed Platelets in Aggregation Facilitated by Covalently Bound Fibrinogen" Blood 61:1, pp. 186-191, 1983.

Ahmadzada, et al., "Fundamentals of siRNA and miRNA therapeutics and a review of targeted nanoparticle delivery systems in breast cancer," Biophysical Reviews, 2018, 10:69-86.

Al Ghaithi, "Evaluation of the total Thrombus-Formation System (T-TAS)," Platelets, 2018, 1-8.

Arav, et al., "Freeze drying (lyophilization) of red blood cells," Journal of Trauma, 2011, 70:S61-S64.

Arnold P., et al., "The preparation and clinical administration of lyophilized platelet material to children with acute leukemia and aplastic anemia," The Journal of Pediatrics, 1956, 49(5):517-522.

Chen, et al., "Advance of molecular imaging technology and targeted imaging agent in imaging and therapy," Biomed. Res. Int., 2014, 819324, 12 pages.

Chen, et al., "Stabilizaton of peptides against proteolysis through disulfide-bridged conjugation with synthetic aromatics," Org. Biomol. Chem., 2017, 15(8):1921-1929.

Christenson et al., "Autologous fibrin glue reinforced by platelets in surgery of ascending aorta", Thorac. Cardiovasc. Surg., vol. 52, p. 225-229, 2004.

Christopher, et al., "MicroRNA therapeutics: discovering novel targets and developing specific therapy," Perspect. Clin. Res., 2016, 7(2):68-74.

Cox, et al., "Platelets and the innate immune system: mechanisms of bacterial-induced platelet activation," Journal of Thrombosis and Haemostasis, 2011, 9:1097-1107.

Daidone, "Usefulness of the Total Thrombus-formation Analysis System (T-TAS) in the diagnosis and characterization of von Willebrand disease," Haemophillia, 2016, 22:949-956.

Daly, et al., "Hemostatic regulators of tumor angiogenesis: a source of antiangiogenic agents for cancer treatment?" Journal of the National Cancer Institute, 2003, 95(22):1660-1673.

(56) References Cited

OTHER PUBLICATIONS

Diener, "Antiplatelet agents and randomized trials," Review in Neurological Diseases, 2007, 4(4):177-183.
European Search Report in EP Appln. No. 05784165.2, dated Mar. 26, 2008.
European Search Report in EP Appln. No. 16808270.9, dated Nov. 22, 2018.
European Search Report in EP Appln. No. 16842662.5, dated Jul. 26, 2019.
European Search Report in EP Appln. No. 17738796.6, dated Jul. 23, 2019.
Fijnheer et al., "Platelet activation during preparation of platelet concentrates: a comparison of the platelet-rich plasma and the buffy coat methods," Transfusion, 1990, 30(7):634-638.
Fischer et al., "Primary and secondary hemostatic functionalities of rehydrated, lyophilized platelets," 2006, Transfusion, 46:1943-1950.
Fitzpatrick, et al., "Thrombosomes: a platelet-derived hemostatic agent for control of noncompressible hemorrhage," Transfusion, 2013, 53:100S-106S.
Gilbert et al., "Platelet-derived microparticles express high affinity receptors for factor VIII.", J.Biol.Chem., 1991, 266:17261-17268.
Giles et al., "A combination of factor Xa and phosphatidylcholine-phosphatidylserine vesicles bypasses factor VIII in vivo", Br. J., Haematol., 1988, 69(4):491-497.
Greene, et al., "Chapter 9: Component Preparation and Manufacturing," Transfusion Medicine and Hemostasis, Elsevier Science, 2009, pp. 45-50.
Heitz, et al., "Twenty years of cell-penetrating peptides: from molecular mechanisms to therapeutics," British Journal of Pharmacology, 2009, 157:195-206.
Hemker, et al., "Calibrated automated thrombin generation measurement in clotting plasma," Pathophysiolo. Haemost. Thromb., 2003, 33:4-15.
Hoffman et al., "Coagulation Factor IXa Binding to Activated Platelets and Platelet-Derived Microparticles: A Flow Cytometric Study," Thromb. Haemost., 1992, 68:74-78.
Holcomb, et al., "Optimal fluid therapy for traumatic hemorrhagic shock," Crit. Care Clin., 2017, 33(1):15-36.
Holme et al., "Platelet-derived microvesicles and activated platelets express factor Xa activity," Blood Coagul. Fibrinolysis, 1995, 6:302-310.
Hong, et al., "Transfection of human platelets with short interfering RNA," Clin. Transl. Sci., 2011, 4(3):180-182.
Hrachovinova et al., "Interaction of P-selectin and PSGL-1 generates microparticles that correct hemostasis in a mouse model of hemophilia A," Nat Med., 2003, 9(8): 1020-1025.
International Search Report and Written Opinion in PCT Appln. No. PCT/US2019/050624, dated Nov. 20, 2019, 23 pages.
Ito, et al., "Total Thrombus-formation Analysis System (T-TAS) can predict periprocedural bleeding events in patients undergoing catheter ablation for atrial fibrillation," Journal of American Heart Association, 2015, 5(1):e002744, 12 pages.
Kerrigan, "Platelet interactions with bacteria," The non-thrombotic role of platelets in health and disease; Chapter 4, 2015, 65-84.
Kerrigan, et al., "Molecular basis for *Staphylococcus aureus* mediated platelet aggregate formation under arterial shear in vitro," Arteriosclerosis Thrombosis and Vascular Biology, 2008, 28(2):334-340.
Kirby et al., "Preparation of liposomes containing Factor VIII for oral treatment of haemophilia," 1984, J. Microencapsul. 1(1): 33-45.
Lam, et al., "siRNA versus miRNA as therapeutics for gene silencing," Molecular Therapy—Nucleic Acids, 2015, 4:e252.
Lannan, et. al., "Breaking the Mold: Transcription Factors in the Anucleate Platelet and Platelet-Derived Microparticles," Front Imunnol., 2015, 6:48, 17 pages.
Makielski, K.M., et al., "Development and implementation of a novel immune thrombocytopenia bleeding score for dogs," J. Vet. Intern. Med., 2018, 32(3):1-10.

Mazzucco et al., "The use of autologous platelet gel to treat difficult-to-heal wounds: a pilot study," Transfusion, 2004, 44:1013-1018.
MedWow, "Manufacturer Specifications—CS-2000 Plus, Baxter," Apr. 19, 2011, retrieved on Sep. 26, 2019 from http://www.medwow.com/med/apheresis-machine/baxter/cs-3000-plus/5782.model-spec, 2 pages.
Merten et al., "Platelet Microparticles Promote Platelet Interaction with Subendothelial Matrix in a Glycoprotein lib/Illa Dependent Mechanism", Circulation, 1999, 99:2577-2582.
Miajlovic, et al., "Both complement- and fibrinogen-dependent mechanisms contribute to platelet aggregation mediated by *Staphylococcus aureus* clumping factor B," Infection and Immunity, 2007, 75(7):3335-3343.
Montecinos, et al., "Selective targeting of bioengineered platelets to prostate cancer vasculature: new paradigm for the therapeutic modalities," 2015, 19(7):1530-1537.
Natan, et al., "Freeze-drying of mononuclear cells derived from umbilical cord blood followed by colony formation," PLoS One, 2009, 4(4):e5240.
Nieuwland et al., "Cell-derived microparticles generated in patients during cardiopulmonary bypass are highly procoagulant", Circulation, 1997, 96:3534-3541.
Novakowski, et. al., "Delivery of mRNA to platelets using lipid nanoparticles," Scientific Reports, 2019, 9:552, 11 pages.
O'Brien, et al., "Multiple mechanisms for the activation of human platelet aggregation by *Staphylococcus aureus*: roles for the clumping factors ClfA and ClfB, the serine-aspartate repeat protein SdrE and protein A," Molecular Microbiology, 2002, 44(4):1033-1044.
Oikarinen et al., "Augmentation of the narrow traumatized anterior alveolar ridge to facilitate dental implant placement," Dent. Traumatol., 2003, 19:19-29.
Oliver, "Dry state preservation of nucleated cells: progress and challenge," Cryobiology, 2011, 63(3):307, abstract.
PCT International Preliminary Report on Patentability in International Appln. No. PCT/US2017/012836, dated Jul. 17, 2018.
PCT International Preliminary Report on Patentability in International Appln. No. PCT/US2005/28559, dated May 8, 2007.
PCT International Preliminary Report on Patentability in International Appln. No. PCT/US2015/060533, dated May 16, 2017.
PCT International Preliminary Report on Patentability in International Appln. No. PCT/US2016/036657, dated Dec. 12, 2017.
PCT International Preliminary Report on Patentability in International Appln. No. PCT/US2016/048846, dated Mar. 6, 2018.
PCT International Preliminary Report on Patentability in International Appln. No. PCT/US2016/065681, dated Jun. 11, 2019.
PCT International Search Report and Written Opinion in International Appln. No. PCT/US2005/28559, dated Mar. 23, 2007.
PCT International Search Report and Written Opinion in International Appln. No. PCT/US2015/060533, dated Jan. 28, 2016.
PCT International Search Report and Written opinion in International Appln. No. PCT/US2016/036657, dated Aug. 29, 2016.
PCT International Search Report and Written Opinion in International Appln. No. PCT/US2016/048846, dated Nov. 16, 2016.
PCT International Search Report and Written Opinion in International Appln. No. PCT/US2016/065681, dated Feb. 17, 2017.
PCT International Search Report and Written Opinion in International Appln. No. PCT/US2017/012836, dated Apr. 7, 2017.
PCT International Search Report and Written Opinion in International Appln. No. PCT/US2018/050924, dated Nov. 20, 2018.
PCT International Search Report and Written Opinion in PCT Appln. No. PCT/US2019/043723, dated Oct. 9, 2019, 16 pages.
Pierce et al., "Platelet-derived growth factor and transforming growth factor-beta enhance tissue repair activities by unique mechanisms", J. Cell Biol., 1989, 109:429-440.
Prior et al., "A Sprayable Hemostat Containing Fibrillar Collagen, Bovine Thrombin, and Autologous Plasma", Ann.Thorac.Surg., 1999, 68:479-485.
Rosing et al., "Impaired factor X and prothrombin activation associated with decreased phospholipid exposure in platelets from a patient with a bleeding disorder", Blood, 1985, 65:1557-1561.
Rowley, et. al., "Platelet mRNA: the meaning behind the message," Curr. Opin. Hematol., 2012, 19(5):385-391.

(56) References Cited

OTHER PUBLICATIONS scbcinfo.org [online], Strong, ed., "Indications for platelet transfusion therapy," available on or before Dec. 25, 2005, via Internet Archive: Wayback Machine URL <https://web.archive.org/web/20051225110714/http://www.scbcinfo.org/publications/bulletin_v2_n2.htm>, 7 pages.
Serebruany, et al., "Crossreactivity of Human versus Swine Platelet Surface Antigens Is Similar for Glycoproteins Ib and IIIa, but Not for the Glycoprotein IIb/IIIa Complex," J.Thromb. and Thromb., 1998, 5:37-41.
Sims et al., "Complement Proteins C5b-9 Cause Release of Membrane Vesicles from the Platelet Surface That Are Enriched in the Membrane Receptor for Coagulation Factor Va and Express Prothrombinase Activiy", J. Biol Chem., 1988, 263:18205-18212.
Sims et al., "Regulatory control of complement on blood platelets. Modulation of platelet procoagulant responses by a membrane inhibitor of the C5b-9 complex", J Biol. Chem., 1989, 264:19228-19235.
Steed, "The role of growth factors in wound healing," Surg. Clin. North Am., 1997, 77:575-586.
Strober, "Trypan blue exclusion test of cell viability," Current Protocols in Immunology, 1997, A.3B.1-A.3B.2.
Tacar, et al., "Doxorubicin: an update on anticancer molecular action, toxicity and novel drug delivery systems," The Journal of Pharmacy and Pharmacology, 2013, 65(2):157-170.
Tans et al., "Comparison of anticoagulant and procoagulant activities of stimulated platelets and platelet-derived microparticles", Blood, 1991, 77:2641-2648.
Taune, et al., "Whole blood coagulation assays ROTEM and T-TAS to monitor dabigatran t dabigatran treatment," Thrombosis Research, 2017, 153:76-82.
T-TAS.info [online], Publications, 2019, retrieved on Aug. 28, 2019, retrieved from URL<https://www.t-tas.info/pub/>, 8 pages.
Valentini, et al., "Use of CD9 and CD61 for the characterization of AML-M7 by flow cytometry in a dog," Vet. Comp. Oncol., 2011, 10:312-318.
Valeri, et al., "Survival of baboon biotin-X-N-hydroxysuccinimide and 111In-oxine-labelled autologous fresh and lyophilized reconstituted platelets," Vox Sanguinis, 2005, 88:122-129.
Vlieghe, et al., "Synthetic therapeutic peptides: science and market," Drug Discovery Today, 2010, 15:40-56.
Wajon et al., "Intraoperative Plateletpheresis and Autologous Platelet Gel Do Not Reduce Chest Tube Drainage or Allogeneic Blood Transfusion After Reoperative Coronary Artery Bypass Graft", Anesth. Analg., 2001, 93:536-542.
Wilkerson, M.J., et al., "Platelet size, platelet surface-associated IgG, and reticulated platelets in dogs with immune-mediated thrombocytopenia," Veterinary Clinical Pathology, 2001, 30(3):141-149.
Wilson, et al., "A simple rapid method for layering blood on Ficoll-Isopaque gradients," Journal of Immunological Methods, 1975, 9(1): 67-68.
Wolkers et al., "Human Platelets Loaded with Trehalose Survive Freeze-Drying", Cryobiology 42:79-87, 2001.
WPI Database No. AN 2014-E98028 / CN103524613, Jan. 22, 2014: 2 pages.
Xu, et al., "Doxorubicin-loaded platelets as a smart drug delivery system: an improved therapy for lymphoma," Scientific Reports, 2017, 7:42632.
Yarovoi et al., "Factor VIII ectopically expressed in platelets: efficacy in hemophilia A treatment", Blood 102(12): 4006-4013, 2003.
Zhou, et. al., "Loading Trehalose into Red Blood Cells by Improved Hypotonic Method," Cell Preservation Technology, 2008, 6(2):119-122.
Samanbar et al., "Evaluation Of The Hemostatic Ability of The New Device 'Total Thrombus Formation Analysis System' (T-TAS) for Thrombocytopeniatients. Invitro effect of lyophilized human platelets", Cellphire, Inc. Jul. 2022, 1 page, Poster.
Sheik et al., "Stably Loading Human Platelets with Gadolinium Conjugates to Enhance Magnetic Resonance Imaging", Cellphire, Inc., 2020,1 page.
Sum et al., "Wound-healing properties of trehalose-stabilized freeze-dried outdated platelets", Transfusion, vol. 47, Issue 4, Apr. 2007, pp. 672-679, doi: 10.1111/j.1537-2995.2007.01170.x.
Swami, et.al., "von Willebrand Disease: A Concise Review and Update for the Practicing Physician", Clinical and Applied Thrombosis/Hemostasis, vol. 23 (8), Nov. 2017, pp. 900-910, DOI: 10.1177/1076029616675969.
Trivedi, et. al., "Freeze-Dried Platelets Promote Clot Formation, Attenuate Endothelial Cell Permeability, And Decrease Pulmonary Vascular Leak In A Murine Model Of Hemorrhagic Shock", The Journal of Trauma and Acute Care Surgery, vol. 90, Issue 2, Feb. 1, 2021, pp. 203-214, doi: 10.1097/TA.0000000000002984.
Van Der Meer et al, Platelet preservation: Agitation and containers, Transfusion and Apheresis Science, vol. 44, Issue 3, Jun. 2011, pp. 297-304, //doi.org/10.1016/j.transci.2011.03.005.
Van Der Meijden et al., "Platelet- and erythrocyte-derived microparticles trigger thrombin generation via factor Xlla", Journal of Thrombosis and Haemostasis, vol. 10, Issue 7, Apr. 26, 2012, pp. 1355-1362, doi.org/10.1111/i.1538-7836.2012.04758.x.
Vibhudutta et al., "Trehalose Stabilized Freeze Dried Human Platelets, Thrombosomes, Reduce Blood Loss In Thrombocytopeniabbit Ear Bleed Model By As Much As 89.5%", Cellphire, Inc. P-0454, www.bodevet.com, Mar. 2017, 1 page, Poster.
Vibhudutta et al., "Trehalose Stabilized Freeze Dried Human Platelets, Thrombosomes, Persist In Circulation 24 Hours After Infusion and Are Non-Immunogenic In New Zealand White Rabbits", International Society of Blood Transfusion Vox Sanguinis, vol. 99, Suppl. 1, P-0454, 2010, p. 262, Abstract.
Vibhudutta et al., "Trehalose Stabilized Freeze Dried Human Platelets, Thrombosomes, Persist In Circulation 24 Hours After Infusion and Are Non-Immunogenic In New Zealand White Rabbits", Cellphire, Inc. P-0454, 1 page, Poster.
Vibhudutta et al., "Trehalose Stabilized Freeze Dried Human Platelets, Thrombosomes, Reduce Blood Loss In Thrombocytopeniabbit Ear Bleed Model By As Much As 89.5%", International Society of Blood Transfusion Vox Sanguinis, vol. 99, Suppl. 1, P-0452, 2010, p. 261, Abstract.
Viswanathan et al., "Clopidogrel Alters Thrombus Quantity and Quality in Patients With Type II Diabetes Mellitus and Stable Coronary Artery Disease", Journal of the American College of Cardiology, vol. 61, No. 10, Mar. 2013, E1154, 1 page.
Wei et al., "ICAM-5/Telencephalin Is a Functional Entry Receptor for Enterovirus D68", Cell Host Microbe, vol. 20, Issue 5, Nov. 9, 2016, pp. 631-641, doi: 10.1016/j.chom.2016.09.013.
Whitman et al., "Design of the CRYPTICS Trail: A Randomized Controlled Trial Comparing Cryopreserved to Liquid Stored Platelets in Patients Undergoing Cardiac Surgery", Journal of Thoracic and Cardiovascular Surgery, 2022, doi.org/10.1016/j.xjon.2022.11.003.
Wright et al., "Doxorubicin delivery via novel lyophilized/reconstituted platelet-product has anti-cancer activity", Hematology & Transfusion International Journal, vol. 9, Issue 3, 2021, pp. 41-51.
Xu et al., "EACA Loaded Platelets Sustain Clots More Efficiently Than Free EACA", Cellphire, Inc., Jul. 2021, 1 page, Poster.
Xu et al., "EACA Loaded Platelets Sustain Clots More Efficiently Then Free EACA", Cellphire, Inc., 2021. 2 page.
Xu et al., "Human Platelet Derived Lyophilized Hemostatic Retains Hemostatic Properties Heparin Complexation with Protamine", Cellphire, Inc. Jul. 2022, 1 page, Poster.
Zafar et. al., "Badimon Perfusion Chamber: An Ex Vivo Model of Thrombosis", Methods Molecular Biology, vol. 1816, 2018, pp. 161-171, doi: 10.1007/978-1-4939-8597-5_12.
Zhou et al., "Hemostatic and Thrombogenic Properties of Lyophilized Human Platelets", CellPhire, Inc. Jul. 2021, 1 page, Poster.
Zhou et al., "Lyophilized Human Platelets Promote Coagulation in Humanized Mouse VWF Transgenic Models of Hemostasis and Thrombosis", Cellphire, Inc., 2021, 1 page.
International Search Report and Written Opinion in PCT Appln. No. PCT/US2020/022705, dated Jul. 29, 2020, 12 pages.

(56) References Cited

OTHER PUBLICATIONS

International Search Report and Written Opinion in PCT Appln. No. PCT/US2020/031172, dated Aug. 12, 2020, 9 pages.
Morrison et al. "Storage of apheresis platelet concentrates after manual replacement of >95% of plasma with PAS 5," Vox Sangunis, May 2014, 107(3):247-253.
Alquwaizani, et.al., "Anticoagulants: A Review of the Pharmacology, Dosing, and Complications", Current Emergency and Hospital Medicine Reports, vol. 1, No. 2, Apr. 21, 2013, pp. 83-97, DOI: 10.1007/s40138-013-0014-6.
Barroso, et. al., "Safety Evaluation Of A Lyophilized Platelet Derived Hemostatic Product", Transfusion, vol. 58(12), Dec. 2018, pp. 2969-2977, DOI: 10.1111/trf.14972.
Bohoněk, Miloš. "Cryopreservation of Platelets: Advances and Current Practice." Cryopreservation Biotechnology in Biomedical and Biological Sciences, Chapter 4. IntechOpen, Dec. 7, 2018, pp. 47-70.
Cap, et. al., "Trauma Induced Coagulopathy", Chapter 22: Platelet Transfusion, Springer International Publishing, 2016, pp. 347-376.
Colman, "Are hemostasis and thrombosis two sides of the same coin?", Journal of Experimental Medicine, Mar. 20, 2006, vol. 203, No. 3, pp. 493-495, doi: 10.1084/jem.20060217.
Cowles, "Anticoagulant effect of aspirin goes beyond platelet aggregation", Hematology/Oncology, May 1, 2007, 3 pages.
Crowe et. al., "Stabilization of Dry Mammalian Cells: Lessons from Nature", Integrative and Comparative Biology, vol. 45, Issue 5, Nov. 2005, pp. 810-820, https://doi.org/10.1093/icb/45.5.810.
Crowe, et. al., "Stabilization of membranes in human platelets freeze-dried with trehalose", Chemistry and Physics of Lipids, vol. 122, Issues 1-2, Jan. 2003, pp. 41-52, https://doi.org/10.1016/S0009-3084(02)00177-9.
Dickerson, "Lyophilized Human Platelets Restore Hemostasis in the Presence of the P2Y12 Inhibitors Cangrelor, Ticagrelor and Clopidogrel", Cellphire Therapeutics Inc., Rockville, MD, 7 pages.
Dickerson, "Lyophilized Human Platelets Restore Hemostasis in the Presence of the P2Y12 Inhibitors Cangrelor, Ticagrelor and Clopidogre", American Society of Hematology, Blood, 3.22 Disorders Of Coagulation Or Fibrinolysis, Nov. 5, 2020, 6 pages.
Dickerson, "Lyophilized human platelets support thrombosis unlike normal platelets in the presence of GPIIb/IIIa antagonists", Cellphire Therapeutics Inc., Rockville, MD, 1 page.
Dickson, et. al., "A scalable, micropore, platelet rich plasma separation device." Biomedical Microdevices, vol. 14(6), Jul. 2012, pp. 1095-1102. DOI:10.1007/s10544-012-9675-2.
Dumont, et. al, "A randomized controlled trial evaluating recovery and survival of 6% dimethyl sulfoxide-frozen autologous platelets in healthy volunteers", Transfusion vol. 53(1), Jan. 2013, pp. 128-137.
Eikelboom, et. al., "Combined antiplatelet and anticoagulant therapy clinical benefits and risks", Journal of Thrombosis and Haemostasis, vol. 5, Suppl 1, Jul. 2007, pp. 255-263, DOI: 10.1111/j.1538-7836.2007.02499.x.
EP Application No. 19840600.1 Extended European Search Report dated Mar. 25, 2022, 8 pages.
Etchill, et. al., "Platelet Transfusion In Critical Care And Surgery: Evidence-Based Review Of Contemporary Practice And Future Directions", SHOCK, vol. 47, No. 5, May 1, 2017, pp. 537-549.
Fischer, et. al., "The interaction of factor VIIa with rehydrated, lyophilized platelets", Platelets, vol. 19 (3), May 2008, pp. 182-191, DOI: 10.1080/09537100701493794.
Fischer, et. al., "Thrombus Formation with Rehydrated, Lyophilized Platelets", Hematology (Amsterdam, Netherlands), vol. 7 (6), Dec. 2002, pp. 359-369, DOI:10.1080/1024533021000047954.
Gao, et. al., "Development of Optimal Techniques for Cryopreservation of Human Platelets: I. Platelet activation during cold storage (at 22 and 8° C.) and cryopreservation", Cryobiology vol. 38(3), May 1999, pp. 225-235, DOI: 10.1006/cryo.1999.2162.
Hagedorn, et. al., "Factor XIIa Inhibitor Recombinant Human Albumin Infestin-4 Abolishes Occlusive Arterial Thrombus Formation Without Affecting Bleeding", Circulation, vol. 121, Issue 13, Apr. 6, 2010, pp. 1510-1517, DOI: 10.1161/CIRCULATIONAHA.109.924761.
Heitmeier, et. al., "Pharmacological profile of asundexian, a novel, orally bioavailable inhibitor of factor XIa", Journal of Thrombosis and Haemostasis, vol. 20, No. 6, Jun. 2022, pp. 1400-1411, https://doi.org/10.1111/jth.15700.
Holmes, et. al., "Combining Antiplatelet and Anticoagulant Therapies", Journal of The American College of Cardiology, vol. 54, No. 2, Jul. 7, 2009, pp. 95-109.
Huebner, et. al., "Freeze-dried plasma enhances clot formation and inhibits fibrinolysis in the presence of tissue plasminogen activator similar to pooled liquid plasma", Transfusion, vol. 57, Issue 8, Aug. 2017, pp. 2007-2015, DOI:10.1111/trf.14149.
Human Translation of Chinese patent No. CN103907595 Published Jul. 9, 2014, Trehalose-containing platelet low temperature preservation solution and application thereof, First Inventor Zhao Shuming.
International Partial Search Report in International Appln No. PCT/US2022/016866, dated May 11, 2022, 13 pages.
International Search Report and Written Opinion in International Appln. No. PCT/US2020/031172, dated Aug. 12, 2020, 8 pages.
International Search Report and Written Opinion in International Appln. No. PCT/US2021/032783, dated Aug. 24, 2021, 13 pages.
International Search Report and Written Opinion in International Appln. No. PCT/US2021/058814, dated Mar. 17, 2020, 14 pages.
International Search Report and Written Opinion in International Appln. No. PCT/US2022/016866, dated Jul. 4, 2022, 18 pages.
International Search Report and Written Opinion in International Appln. No. PCT/US2022/016883, dated May 11, 2022.
Jennings, et. al., "Antiplatelet and anticoagulant agents: Key differences in mechanisms of action, clinical application, and therapeutic benefit in patients with non-ST-segment-elevation acute coronary syndromes", Current Opinion in Cardiology vol. 23, No. 4, Jul. 2008, pp. 302-308, DOI: 10.1097/HCO.0b013e3283021ad9.
Jennings, et. al., "The pharmacodynamics of parenteral glycoprotein IIb/IIIa inhibitors", Journal of Interventional Cardiology, vol. 15, No. 1, Feb. 2002, pp. 45-60, DOI: 10.1111/j.1540-8183.2002.tb01034.x.
Joshi, et. al., "Lyophilised Reconstituted Human Platelets Increase Thrombus Formation In A Clinical Ex Vivo Model Of Deep Arterial Injury", Thrombosis and Haemostasis, vol. 108, No. 1, 2012, pp. 176-182, DOI: 10.1160/TH12-02-0059.
Li, et.al., "Extended antiplatelet therapy with clopidogrel alone versus clopidogrel plus aspirin after completion of 9- to 12-month dual antiplatelet therapy for acute coronary syndrome patients with both high bleeding and ischemic risk. Rationale and design of the OPT-BIRISK double-blinded, placebo-controlled randomized trial", American Hear Journal, vol. 228, Oct. 2020, pp. 1-7, https://doi.org/10.1016/j.ahj.2020.07.005.
Lo, et. al., "Development of a multi-compartment microfiltration device for particle fractionation" 16th International Conference on Miniaturized Systems for Chemistry and Life Sciences, MicroTAS 2012—Okinawa, Japan, Oct. 28, 2012-Nov. 1, 2012, 3 pages.
Machine Language Translation of Chinese Patent No. CN108715834, 10 pages.
Machine Language Translation of Japanese Patent JP2012143554 Titled "[EN] Polysulfone-Based Hollow Fiber Membrane, Hollow Fiber Membrane Module for Cleaning Platelet Suspension, and Cleaning Method of Platelet Suspension."
Mailer, et. al., "Commentary on "Pharmacological profile of asundexian, a novel, orally bioavailable inhibitor of factor XIa": Small molecule factor XIa inhibitor asundexian allows for safer anticoagulation", Journal of Thrombosis and Haemostasis, vol. 20, Issue 6, Jun. 2022, pp. 1309-1311, https://doi.org/10.1111/jth.15722.
Marder, "Bleeding Complications Of Thrombolytic Treatment", American Journal of Hospital Pharmacy, vol. 47, Suppl 2, Sep. 1990, pp. S15-S19.
McCarrel, et. al., "Temporal Growth Factor Release from Platelet-Rich Plasma, Trehalose Lyophilized Platelets, and Bone Marrow Aspirate and Their Effect on Tendon and Ligament Gene Expres-

(56) References Cited

OTHER PUBLICATIONS sion" Journal of Orthopaedic Research : Official Publication of the Orthopaedic Research Society, vol. 27(8), Aug. 1, 2009, pp. 1033-1042, DOI: 10.1002/jor.20853.

Mehendale, et. al., "Platelet Enrichment From Whole Blood In A Clog-Free Microfluidic Radial Pillar Device (RAPID)", Biomedical Microdevices, bioRxiv, Oct. 4, 2017, DOI: https://doi.org/10.1101/197749.

Mehendale, et. at., "Platelet Enrichment In A Continuous And Clog-Free Microfluidic Filter With Sunflower Head Geometry", 20th International Conference on Miniaturized Systems for Chemistry and Life Sciences, Dublin, Ireland, Oct. 9-13, 2016, pp. 272-273.

Mihatov, et. al., "Individualizing Dual Antiplatelet Therapy (DAPT) Duration Based on Bleeding Risk, Ischemic Risk, or Both: An Analysis From the DAPT Study", Cardiovascular Revascularization Medicine, vol. 41, Aug. 2022, pp. 105-112, https://doi.org/10.1016/j.carrev.2022.01.006.

Montague, "Strategies To Improve Haemostasis In Trauma: Evaluation Of Thrombosomes In The Presence Of Native Platelet Dysfunction", vol. 100, Issue Suppl 3, 2014, pp. A91-A92, DOI:10.1136/heartjnl-2014-306118.158.

Pietramaggiori, et. al., "Trehalose Lyophilized Platelets For Wound Healing", Wound Repair And Regeneration : Official Publication Of The Wound Healing Society [and] the European Tissue Repair Society, vol. 15 (2), Mar. 9, 2007, pp. 213-220. doi:10.1111/j.1524-475X.2007.00207.x.

Read, et. al., "Preservation of hemostatic and structural properties of rehydrated lyophilized platelets: potential for long-term storage of dried platelets for transfusion", Proceedings of the National Academy of Sciences of the USA, vol. 92, Jan. 1995, pp. 397-401, DOI: 10.1073/pnas.92.2.397.

Robson, et. al., "Coronavirus RNA Proofreading: Molecular Basis and Therapeutic Targeting", Molecular Cell, vol. 79, No. 5, 3 Sep. 3, pp. 710-727, DOI:10.1016/j.molcel.2020.07.027, XP055785471.

Sane, et. al., "Bleeding During Thrombolytic Therapy For Acute Myocardial Infarction: Mechanisms and Management", Annals Of Internal Medicine, vol. 111, No. 12, Dec. 15, 1989, pp. 1010-1022.

Schoug, et.al., "Differential effects of polymers PVP90 and Ficoll400 on storage stability and viability of Lactobacillus coryniformis Si3 freeze-dried in sucrose", Journal of Applied Microbiology, vol. 108, No. 3, pp. 1032-1040, Feb. 8, 2010.

Sibbing, et. al., "Antiplatelet effects of clopidogrel and bleeding in patients undergoing coronary stent placement", Journal of Thrombosis and Haemostasis, vol. 8, Issue 2, pp. 250-256, DOI: 10.1111/j.1538-7836.2009.03709.x.

Abdelgawwad, et al., "Transfusion of plateletes loaded with recombinant ADAMTS13 is efficacious for inhibiting arterial thrombosis in mice and in human," Arterioscler. Thromb. Vas. Biol., 2018, 38(11):2731-2743.

Bynum, et al., "Evaluation of a lyophilized platelet-derived hemostatic product," Transfusion, 2019, 49:1490-1498.

Cellphire, "Loading Platelets with Biological Agents for Enhanced Local Delivery," 2006, 14 pages.

Dennison, "A simple and universal method for making up buffer solutions," Biochem. Edu., 1988, 16(4):210-211.

Dielis, et al., "Coagulation factors and the protein C system as determinants of thrombin generation in a normal population," J. Thromb. Haemost., 2008, 6:125-131.

Dong, et al., "Ristocetin-dependent, but not botrocetin-dependent, binding of von Willebrand factor to the platelet glycoprotein Ib-IX-V complex correlates with shear-dependent interactions," Blood, 2001, 97:162-+168.

International Preliminary Report on Patentability in PCT Appln. No. PCT/US2018/050924, dated Mar. 17, 2020, 17 pages.

International Search Report and Written Opinion in PCT Appln. No. PCT/US2019/063549, dated Feb. 4, 2020, 10 pages.

International Search Report and Written Opinion in PCT Appln. No. PCT/US2019/063650, dated Feb. 27, 2020, 11 pages.

International Search Report and Written Opinion in PCT Appln. No. PCT/US2019/063736, dated Feb. 20, 2020, 10 pages.

International Search Report and Written Opinion in PCT Appln. No. PCT/US2019/063750, dated Feb. 19, 2020, 10 pages.

Kariko, et al., "Phosphate-enhanced transfection of cationic lipid-complexed mRNA and plasmid DNA," Biochim. Biophys. Acta, 1998, 1369(2):320-334.

Mishra, et al., "Cell-penetrating peptides and peptide nucleic acid-coupled MRI contrast agents: evaluation of cellular delivery and target binding," Bioconjugate Chem., 2009, 20:1860-1868.

Morris, et al., "A peptide carrier for the delivery of biologically active proteins into mammalian cells," Nature Biotechnology, 2001, 19:1173-1176.

Szekely and Lex, "Antifibrinolytics," Heart, Lung and Vessels, 2014, 6(1):5-7.

Volz, et al., "Inhibition of platelet GPVI induces intratumor hemorrhage and increases efficacy of chemotherapy in mice," Blood, 2019, 133(25):2696-2706.

Wang, et al., "Commonly used dietary supplements on coagulation function during surgery," Medicines, 2015, 2:157-185.

Appleman et al., "Cryopreservation of canine platelets," Journal of veterinary internal medicine, Jan. 2009, 23(1):138-145.

Clemmons et al., "Acquisition and aggregation of canine blood platelets: basic mechanisms of function and differences because of breed origin," American journal of veterinary research, Jan. 1, 1984, 45(1):137-144.

Extended European Search report in EP Appln. No. 18856149.2, dated May 26, 2021, 9 pages.

Lee et al., "Novel treatment modalities: New platelet preparations and subsititutes," British journal of haematology, Sep. 2001, 114(3):496-505.

PCT International Preliminary Report on Patentability in PCT Appln. No. PCT/US2019/063549, dated Jun. 10, 2021, 9 pages.

PCT International Preliminary Report on Patentability in PCT Appln. No. PCT/US2019/063650, dated Jun. 10, 2021, 9 pages.

PCT International Preliminary Report on Patentability in PCT Appln. No. PCT/US2019/063750, dated Jun. 10, 2021, 8 pages.

PCT International Preliminary Report on Patentability in PCT Appln. No.PCT/US2019/063736, dated Jun. 10, 2021, 8 pages.

PCT International Search Report and Written Opinion in International Appln. No. PCT/US2021/016390, dated May 18, 2021, 13 pages.

PCT International Search Report and Written Opinion in PCT Appln. No. PCT/US2021/016360, dated May 21, 2021, 13 pages.

PCT International Search Report and Written Opinion in PCT Appln. No. PCT/US2021/016363, dated May 18, 2021, 15 pages.

PCT International Search Report and Written Opinion in PCT Appln. No. PCT/US2021/016389, dated May 18, 2021, 15 pages.

Srivastava, et. al., "The rebirth of the contact pathway: a new therapeutic target", Current Opinion in Hematology, vol. 27, No. 5, Sep. 2020, pp. 311-319, doi: 10.1097/MOH.0000000000000603.

Tang, et. al., "Targeted repair of heart injury by stem cells fused with platelet nanovesicles", Nature Biomedical Engineering, vol. 2, No. 1, May 30, 2018, pp. 17-26, DOI:10.1038/s41551-017-0182-x.

Tsai, et.al, "Increased risk of bleeding in patients on clopidogrel therapy after drug-eluting stents implantation: insights from the HMO Research Network-Stent Registry (HMORN-stent)", Circulation Cardiovascular Interventions, vol. 3, Issue 3, Jun. 1, 2010, pp. 230-235, DOI: 10.1161/CIRCINTERVENTIONS. 109.919001.

Undas, et. al., "Antithrombotic properties of aspirin and resistance to aspirin: beyond strictly antiplatelet actions", Blood, vol. 109, No. 6, Mar. 15, 2007, pp. 2285-2292, DOI: 10.1182/blood-2006-01-010645.

Valeri, et. al., "Freezing human platelets with 6 percent dimethyl sulfoxide with removal of the supernatant solution before freezing and storage at—80° C. without postthaw processing" Transfusion, vol. 45 (12), Dec. 2005, pp. 1890-1898, DOI: 10.1111/j.1537-2995.2005.00647.x.

Wickramasinghe, "Washing Cryopreserved Blood Products Using Hollow Fibres", Food and Bioproducts Processing, vol. 77, Issue 4, Dec. 1999, pp. 287-292, DOI:org/10.1205/096030899532574.

(56) References Cited

OTHER PUBLICATIONS

Xu, et.al., "Thrombosomes As a Treatment Option for Low-Dose Heparin Reversal", Cellphire Therapeutics, Inc., Rockville, MD, 2020 Annual Meeting, 3 pages.
Extended European Search report in EP Appln. No. 16923314.5, dated Jun. 18, 2020, 7 pages.
Invitation to Pay Additional Fees in PCT Appln. No. PCT/US2020/022705, dated May 18, 2020, 2 pages.
Ishler, "StablePlate RX Canine Promotes in vitro Thromblin Generation and Thrombus Formation Under High Shear," Journal of Veterinary Internal Medicine, 2019 ACVIM Forum Research Abstract Program, p. 2483, Abstract Only.
Tsegaye et al., "Platelet activation suppresses HIV-1 infection of T cells," Retrovirology, 2013, 10:48.
Bannai et al., "The effects of pH and agitation on platelet preservation", The Journal Of AABB Transfusion, vol. 25, Jan.-Feb. 1985, pp. 57-59, https://doi.org/10.1046/j.1537-2995.1985.25185116505.x.
Böck et al., "Cryopreservation of human platelets with dimethyl sulfoxide: changes in biochemistry and cell function", Transfusion, vol. 35, No. 11, Nov.-Dec. 1995, pp. 921-924, doi: 10.1046/i.1537-2995.1995.351196110896.x.
Booth et al., "Lyophilized human platelets are superior to apheresis or fresh-drawn platelets in their ability to accelerate thrombin production", Cellphire, Inc. Jul. 2022, 1 page, Poster.
Charkhkar et al., "Amyloid beta modulation of neuronal network activity in vitro", Brain Research, vol. 1629, Dec. 2015, pp. 1-9, doi: 10.1016/j.brainres.2015.09.036.
Chelliah et. al., "P-selectin antagonism reduces thrombus formation in humans", Journal of Thrombosis and Haemostasis, vol. 7, No. 11, Nov. 2009, pp. 1915-1919. doi: 10.1111/j.1538-7836.2009.03587.x.
Crowe et al., "Freeze-dried platelets: Moving towards clinical use", Cryobiology, vol. 66, Issue 3, Jun. 2013, p. 348, Abstract, doi.org/10.1016/j.cryobiol.2013.02.028.
Dee et al., Trehalose Stabilized Freeze Dried Human Platelets, Thrombosomes, Express Surface Markers, Thromboelastogram (TEG) Values And Size Distribution Similar To Two To Three Day Old Stored Platelets, Cliphire, Inc., P-0453, 2019, 1 page, Poster.
Dickerson et al., "Lyophilized Human Platelets Restore Hemostasis in the Presence of the P2Y12 Inhibitors Cangrelor, Ticagrelor and Clopidogrel", Cellphire, Inc., 2020, 6 pages, Poster.
Dickerson et al., "Lyophilized human platelets support thrombosis unlike normal platelets in the presence of GPIIb/IIIa antagonists", Cellphire, Inc., AS-ISTH-2021-01436, 2021. 2 pages, Abstract.
Dickerson et al., "Thrombosomes As a Treatment Option for Low-Dose Heparin Reversal", Cellphire, Inc, Oct. 2020. 1 page, Poster.
Dinçer et al., "Effect of taurine on wound healing", Amino Acids, vol. 10, Issue 1, Mar. 1996, pp. 59-71, doi: 10.1007/BF00806093.
Extended European Search Report in EP Appln. No. 19888909.9 dated Sep. 28, 2022.
Extended European Search Report in EP Appln. No. 19888994.1 dated Nov. 7, 2022.
Extended European Search Report in EP Appln. No. 19891082.0 dated Sep. 30, 2022.
Extended European Search Report in EP Appln. No. 20769409.2 dated Dec. 6, 2022.
Extended European Search Report in EP Appln. No. 20802506.4 dated Jan. 4, 2023.
Fitzpatrick et al., "A Novel Lyophilized Platelet Derivative Produces Effective Hemostasis in Uncontrolled Bleeding/Shock Model without Systemic Thrombosis", Blood, vol. 118, Issue 21, Nov. 18, 2011, pp. 719-722, doi.org/10.1182/blood.V118.21.719.719.
Fitzpatrick et al., "Freeze-dried platelets: Advancing towards clinical use", Cryobiology, vol. 67, Issue 3, Dec. 2013, p. 420, Abstract, doi.org/10.1016/j.cryobiol.2013.09.086.
Fitzpatrick et al., "Stabilization and preservation of a platelet derived hemostatic agent, Thrombosomes", Cryobiology, vol. 63, Issue 3, Dec. 2011, p. 306, Abstract, doi:10.1016/j.cryobiol.2011.09.005.
Fitzpatrick et al., "Trehalose Stabilized Freeze Dried Human Platelets, Thrombosomes, Express Surface Markers, Thromboelastogram (TEG) Values And Size Distribution Similar To Two To Three Day Old Stored Platelets", International Society of Blood Transfusion Vox Sanguinis, vol. 99, Suppl. 1, P-0453, 2010, p. 262, Abstract.
Fitzpatrick, "Novel platelet products under development for the treatment of thrombocytopenia or acute hemorrhage", Transfusion and Apheresis Science, vol. 58, Issue 1, Feb. 2019, pp. 7-11, doi: 10.1016/j.transci.2018.12.010.
Godier et al., "Management of antiplatelet therapy for non elective invasive procedures of bleeding complications: proposals from the French working group on perioperative haemostasis (GIHP), in collaboration with the French Society of Anaesthesia and Intensive Care Medicine (SFAR)" Anaesthesia, Critical Care and Pain Medicine, vol. 38, Issue 3, Jun. 2019, pp. 289-302, doi: 10.1016/j.accpm.2018.10.004.
Goggs, et. al., "Lyophilized Platelets Versus Cryopreserved Platelets For Management Of Bleeding In Thrombocytopenic Dogs: A Multicenter Randomized Clinical Trial", Journal Of Veterinary Internal Medicine, Nov. 2020, vol. 34, Issue 6, pp. 2384-2397, doi: 10.1111/jvim.15922.
Grosset et al., "Rapid presymptomatic detection of PrPSc via conformationally responsive palindromic PrP peptides", Peptides, vol. 26, Issue 11, Nov. 2005, pp. 2193-2200, doi: 10.1016/j.peptides.2005.03.006.
Hale et al., "A Novel Use Of the NOD SCID Mouse Model for Hemostatic Efficacy", Cellphire, Inc., 2019, 1 page.
Inaba et al., "Dried platelets in a swine model of liver injury", Shock, vol. 41, Issue 5, May 2014, pp. 429-434, doi: 10.1097/SHK.0000000000000141.
Ishler et al., "Lyophilized Human Platelets Interact with Fresh Platelets to Promote Hemostasis Under Shear In Vitro", Cellphire, Inc., 2021, 2 page, Abstract.
Ishler et al., "Lyophilized Human Platelets Interact with Fresh Platelets to Promote Hemostasis Under Shear In Vitro", Cellphire, Inc., PB0990, Jul. 2021, 1 page, Poster.
Ishler et al., "Lyophilized Platelets Show Hemostatic Function Independent of von Willebrand Factor", Cellphire, Inc., Department of Discovery and Research, ISth 2020 Virtual Congress, Jul. 2020, 1 page, Poster.
Ishler et al., "StablePlate RX® Canine Promotes In Vitro Thrombin Generation and Thrombus Formation Under High Shear", Cellphire, Inc., 2019, 1 page, Poster1.
Ishler et al., "StablePlate RX® Canine Promotes In Vitro Thrombin Generation and Thrombus Formation Under High Shear", Cellphire, Inc., 2019, 1 page, Poster2.
Joshi et al., "Thrombosomes Show Dose-Dependent Increase in Thrombus Formation in a Model of Deep Arterial Injury", Blood, vol. 118, Issue 21, Nov. 18, 2011, Abstract 2319, 8 pages, doi.org/10.1182/blood.V118.21.2319.2319.
Kuhn et al., "Assessing Circulation Persistence of Human Platelet Products in a NOD-SCID Mouse Model", Cellphire, Inc. Jul. 2022, 1 page, Poster.
Lassila et al., "Dynamic Monitoring of Platelet Deposition on Severely Damaged Vessel Wall in Flowing Blood. Effects of Different Stenoses on Thrombus Growth", Arteriosclerosis, vol. 10, No. 2, Mar.-Apr. 1990, pp. 306-315, doi: 10.1161/01.atv.10.2.306.
Lee et al., "High Efficiency Transfection and Preservation of Platelets with Tumor Suppressing Short RNA", Cellphire, Inc. Jul. 2020, 1 page, Poster.
Lee et al., "Lyophilized Human Platelets Exhibit Adhesive Interactions with *Staphylococcus aureus*", Cellphire, Inc. Jul. 2020, 1 page, Poster.
Lucking et. al., "Characterisation and reproducibility of a human ex vivo model of thrombosis", Thrombosis Research, vol. 126, No. 5, Nov. 2010, pp. 431-435, doi: 10.1016/j.thromres.2010.06.030.
Marris, "The war against wounds", Nature, Mar. 21, 2007, Issue 446, pp. 369-371.
Mathews et al., "Development of Lyophilized Platelet-Derived Extracellular Vesicles for Multiple Indications", Cellphire, Inc., Oct. 2020, 1 page, Poster.

(56) References Cited

OTHER PUBLICATIONS

Mathews et al., "Development of Lyophilized Platelet-Derived Extracellular Vesicles for Multiple Indications", Cellphire, Inc., 2020, 1 page, Abstract.
Meisel et. al., "A Simplified Direct Lipid Mixing Lipoplex Preparation: Comparison of Liposomal-, Dimethylsulfoxide-, and Ethanol-Based Methods", Scientific Reports, vol. 6, Article 27662, Jun. 21, 2016, 12 pages, doi: 10.1038/srep27662.
Midgett et al., "Combination of freeze-dry microscopy, differential scanning calorimetry, and electron microscopy analysis as a guide for lyophilization cycle optimization to enhance Thrombosomes function", Cryobiology, vol. 63, Issue 3, 2011, p. 320, Abstract, doi:10.1016/j.cryobiol.2011.09.054.
Moskowitz et al., "Hemostatic Properties of Infusible Trehalose-Stabilized Lyophilized Platelet Derivatives", Blood, vol. 104, Issue 11, Nov. 16, 2004, p. 834, Abstract, doi.org/10.1182/blood.V104.11.834.834.
Moskowitz, "Thrombosomes for the Treatment of Bleeding Associated with Aggressive Anticoagulation", Cellphire, Inc., Dec. 2021, 40 pages, Posters.
Müller et. al., "Factor XI and XII as antithrombotic targets", Current Opinion In Hematology, vol. 15, No. 5, Sep. 2011, pp. 349-355, doi: 10.1097/MOH.0b013e3283497e61.
NasrEldin, "Effect of cold storage on platelets quality stored in a small containers: Implications for pediatric transfusion", Pediatric Hematology Oncology Journal, vol. 2, Issue 2, Aug. 2017, pp. 29-34, doi.org/10.1016/j.phoj.2017.07.001.
Ohanian, et. al., "Freeze-Dried Platelets Are A Promising Alternative In Bleeding Thrombocytopeniatients with Hematological Malignancies", American Journal of Hematology, vol. 97, Issue 3, Mar. 1, 2022, pp. 256-266, doi: 10.1002/ajh.26403.
Pati et al., "Targeting the Endotheliopathy of Trauma in Hemorrhagic Shock and Traumatic Brain Injury with Freeze-Dried Platelets", Defense Technical Information Center, U.S. Army Medical Research and Development Command, Medicine and Medical Research; Biology, Sep. 1, 2020, 22 pages,.
Powner, et. al., "Counteracting The Effects Of Anticoagulants And Antiplatelet Agents During Neurosurgical Emergencies", Neurosurgery, vol. 57, No. 5, Nov. 2005 pp. 823-831.
Reddoch et al., "Extended Storage of Refrigerated Platelets in Isoplate and Intersol PAS: An Evaluation of Two FDA-Approved Methods of Collection", Blood, vol. 128, Issue 22, Dec. 2, 2016, 3 pages, doi.org/10.1182/blood.V128.22.2631.2631.
Bullok, et al., "Permeation Peptide Conjugates for In Vivo Molecular Imaging Applications", Molecular Imaging, Jan.-Mar. 2006, vol. 5, Issue 1, pp. 1-25.
Extended European Search Report in EP Appln. No. 19860896.0 dated Jun. 14, 2023.
Ghaithi et al., "Evaluation of the Total Thrombus-Formation System (T-TAS): application to human and mouse blood analysis", Platelets, vol. 30, Issue 7, 2019, pp. 893-900, doi: 10.1080/09537104.2018.1535704.
International Partial Search Report in International Appln No. PCT/US2022/079280, dated Feb. 20, 2023, 14 pages.
International Search Report and Written Opinion in International Appln No. PCT/US2022/079280, dated Apr. 21, 2023, 27 pages.
International Search Report and Written Opinion in International Appln. No. PCT/US2023/066965, dated Aug. 4, 2023, 10 pages.
Ishler et al., "Lyophilized Human Platelets Show Hemostatic Function Independent of von Willebrand Factor", Abstract No. PB1533, ISth 2020 Virtual Congress Presentation, Jul. 2020, Res Pract Thromb Haemost. 2020; 4 (Suppl 1). https://abstracts.isth.org/abstract/lyophilized-human-platelets-show-hemostatic-function-independent-of-von-willebrand-factor/.
Machine Language Translation of Chinese Patent No. CN109942687 A, Shen et at., Titled [EN], "68Ga Marks EACA Modification c-Met Molecular Imaging Probe And Preparation And Application", Jun. 28, 2019, 10 pages.
Millipore Sigma, "Dulbecco's Modified Eagle's Medium (DMEM)Formulation", Merck KGaA, Sigma-Aldrich Solutions, 2023, 15 pages, retreived from https://www.sigmaaldrich.com/US/en/technical-documents/technical-article/cell-culture-and-cell-culture-analysis/mammalian-cell-culture/dulbecco-modified-eagle-medium-formulation.
Ogiwara, et al., "Procoagulant Activity of Antifibrinolytic Agents; A Novel Hemostatic Mechanism of Tranexamic Acid and Epsilon-Aminocaproic Acid", Blood, Nov. 19, 2010, vol. 116, Issue 21, Abstract 1151, 3 pages, https://doi.org/10.1182/blood.V116.21.1151.1151.
Pan, et al., "Wound healing monitoring using near infrared fluorescent fibrinogen", Biomedical Optics Express, Jul. 27, 2010, vol. 1, Issue 1, pp. 285-294, doi: 10.1364/boe.1.000285.
Pietramaggiori et al., "Freeze-dried platelet-rich plasma shows beneficial healing properties in chronic wounds", Wound Repair And Regeneration, vol. 14, Issue 5, Sep. 29, 2006, pp. 573-580, doi.org/10.1111/j.1743-6109.2006.00164.x.
Reuss et al., "Intracellular delivery of carbohydrates into mammalian cells through swelling-activated pathways", The Journal Of Membrane Biology, vol. 200, Issue 2, Jul. 15, 2004, pp. 67-81, doi: 10.1007/s00232-004-0694-7.
Török et al., "Preservation of Trehalose-Loaded Red Blood Cells by Lyophilization", Cell Preservation Technology, vol. 3, No. 2, Jul. 11, 2005, pp. 96-11, doi.org/10.1089/cpt.2005.3.96.
Wang et al., "Solubility and Molecular Interactions of Trimetazidine Hydrochloride in 12 Monosolvents and Solvent Mixtures of Methanol + (Ethanol, N,N-Dimethylformamide or Ethyl Acetate)", Journal Of Chemical Engineering Data, Folume 63, Sep. 6, 2018, pp. 3704-3714, doi.org/10.1021/acs.jced.8b00235.
Wikström et al., "Viability of freeze dried microencapsulated human retinal pigment epithelial cells", European Journal Of Pharmaceutical Sciences, vol. 47, Issue 2, Sep. 29, 2012, pp. 520-526, doi: 10.1016/j.ejps.2012.06.014.
Zhang et al., "Coupling of liquid chromatography with mass spectrometry by desorption electrospray ionization (DESI)", Chemical Communications, Issue 14, Feb. 28, 2011, pp. 4171-4173, doi.org/10.1039/C0CC05736C.
Abreu-Blanco et al., "Therapeutic effect of Lyophilized human platelets in an in vitro surrogate model of Bernard-Soulier syndrome and in patient samples", Cellphire, Inc., Oct. 14-17, 2023, 2 pages, abstract.
Abreu-Blanco et al., "Therapeutic effect of Lyophilized human platelets in an in vitro surrogate model of Bernard-Soulier syndrome and in patient samples", Cellphire, Inc., Association For The Advancement Of Blood & Biotherapies, Oct. 14-17, 2023, 1 page, poster.
Extended European Search Report in EP Appln. No. 20855485.7 dated Sep. 15, 2023.
Extended European Search Report in EP Appln. No. 20855619.1 dated Sep. 15, 2023.
Booth et al., "Lyophilized human platelets are superior to apheresis or fresh-drawn platelets in their ability to accelerate thrombin production", Cellphire, Inc. Jul. 2022, 1 page, abstract.
Chen et al., "Expanding the Potential of Doxorubicin-Loaded Cryopreserved Platelets for Targeted Cancer Drug Delivery", Cellphire, Inc., 21st International Drug Delivery and Nanomedicines Symposium, Sep. 15-17, 2023, 1 page, poster.
Chen et al., "Stabilized Platelets: A Drug Delivery System for Potential Human Hepatocellular Carcinoma Therapy", Cellphire, Inc. ISth 2023, Montréal, Jun. 24-28, 2023, 1 page, poster.
Durbin et al., "Platelet Extracellular Vesicles as a Therapeutic Agent in Hemorrhagic Shock", Oregon Health & Science University Department of Surgery, Division of Trauma, Sep. 20, 2023, 23 pages.
Gybel-Brask et al., "Freeze-dried platelets (Thrombosomes®) reverses CPB-induced platelet dysfunction ex-vivo", RegionH, Rigshospitalet, The Center of Diagnostic Investigations, 2023, 1 page, poster.
International Search Report and Written Opinion in International Appln. No. PCT/US2023/066904, dated Sep. 12, 2023, 12 pages.
Kuhn et al., "Mechanism of Action of a Freeze-dried Platelet-derived Hemostatic Product", Cellphire, Inc. Cellular Therapeutics in Trauma and Critical Care, May 8-11, 2023, 1 page, poster.
Sheik et al., "Stably Loading Human Platelets with Gadolinium Conjugates to Enhance Magnetic Resonance Imaging", Cellphire, Inc., 2020, 3 pages, poster.

(56) References Cited

OTHER PUBLICATIONS 2.palomar.edu [online], "The Five Kingdoms Of Life," Feb. 1998, retrieved on May 17, 2021, retrieved from URL <https://www2.palomar.edu/users/warmstrong/trfeb98.htm>; 18 pages.

Chen et al., "Modifying murine von Willebrand factor A1 domain for in vivo assessment of human platelet therapies," Nature biotechnology, Jan. 2008, 26(1):114-119.

diapharma.com [online], "DiaPharmaProductList," retrieved on Feb. 18, 2021, retrieved from URL<http://diapharma.com/wp-content/uploads/2016/03/DiaPharmaProductList_ML-00-00002REV7.pdf>, 4 pages.

Gaertner et al., "Migrating platelets are mechano-scavengers that collect and bundle bacteria," Cell, Nov. 30, 2017, 171(6):1368-1382.

Healthline.com [online], "How Many Cells Are in the Human Body? Fast Facts," Jul. 18, 2018, retrieved on May 17, 2021, retrieved from URL<https://www.https://www.healthline.com/health/number-of-cells-in-body>, 11 pages.

helena.com [online], "Ristocetin Cofactor Assay," retrieved on Feb. 18, 2021, retrieved from URL <https://www.helena.com/Procedures/Pro064Rev5.pdf>, 2 pages.

Homepage.haemonetics.com [online], "TEG® 5000 Thrombelastograph® Hemostasis Analyzer System," retrieved Feb. 18, 2021, retrieved from URL<http://homepage.haemonetics.com/en/products/devices/surgical-and-diagnostic-devices/teg-5000>, 3 pages.

Kishbaugh et al., "Intervening with Platelet Therapies," NEHL at the National Zoo, 2017, vol. 4 #2, 4 Pages.

Luo et al., "Construction and in vitro studies of magnetic-apoferritin nanocages conjugated with KGDS peptide targeted at activated platelets for the MRI diagnosis of thrombus," Journal of Nanoparticle Research, Aug. 2019, 21(8):1-12.

microbenotes.com [online], "Types of Plant Cell—Definition, Structure, Functions, Diagrams," Feb. 25, 2020, retrieved May 17, 2021, retrieved from URL<microbenotes.com/types-of-plant-cell/>, 31 pages.

PCT International Preliminary Report on Patentability in International Appln. No. PCT/US2019/043723, dated Feb. 11, 2021, 14 pages.

PCT International Preliminary Report on Patentability in International Appln. No. PCT/US2019/050624, dated Mar. 25, 2021, 10 pages.

PCT International Search Report and Written Opinion for International Appln. No. PCT/US2020/62214, dated Mar. 17, 2021, 9 pages.

PCT International Search Report and Written Opinion in International Appln. No. PCT/US2020/046522, dated Nov. 10, 2020, 10 Pages.

PCT International Search Report and Written Opinion in International Appln. No. PCT/US2020/046525, dated Nov. 10, 2020, 11 Pages.

PCT International Search Report and Written Opinion in International Appln. No. PCT/US2020/062216, dated Feb. 9, 2021, 9 pages.

PCT International Search Report and Written Opinion in International Appln. No. PCT/US2020/049489, dated Feb. 16, 2021, 8 Pages.

PCT International Search Report and Written Opinion in International Appln. No. PCT/US2020/042492, dated Nov. 24, 2020, 9 pages.

Robson et al., "Coronavirus RNA proofreading: molecular basis and therapeutic targeting," Molecular Cell, Aug. 4, 2020, 18 Pages.

Scheinkönig et al., "Adoption of long-term cultures to evaluate the cryoprotective potential of trehalose for freezing hematopoietic stem cells," Bone marrow transplantation, Sep. 2004, 34(6):531-536.

thrombinoscope.com [online], "Thrombin Calibrator," retrieved on Feb. 18, 2021, retrieved from URL <https://www.thrombinoscope.com/method-products/products/>, 2 pages.

Ullah et al., "A Review on Malarial Parasite," World Journal of Zoology, 2015, 10(4):285-290.

Whitney et al. "Ratiometric Activatable Cell-Penetrating Peptides Provide Rapid In Vivo Readout of Thrombin Activation," Angewandte Chemie International Edition, 2013, 52:325-330.

* cited by examiner

FIG. 4A-C

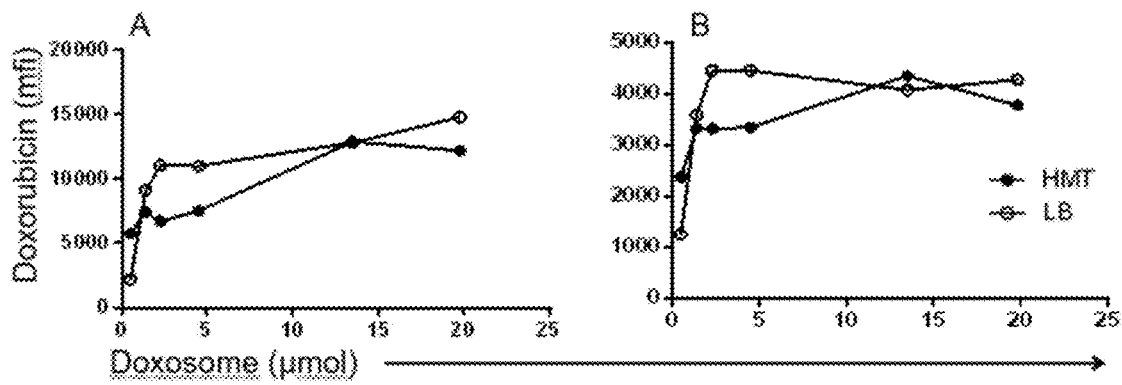
FIGS. 6A (left) & 6B (right)
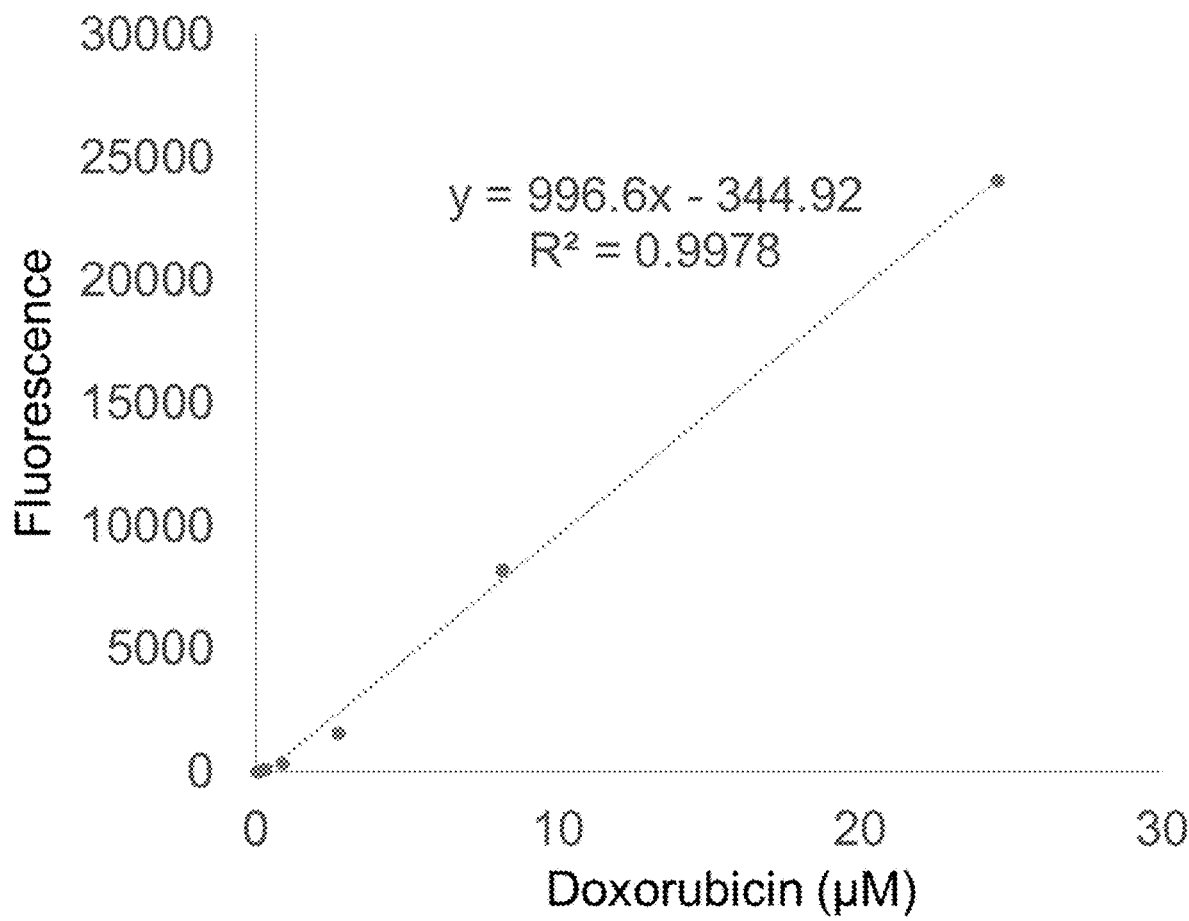
FIG. 7

PLATELETS LOADED WITH ANTI-CANCER AGENTS

CROSS-REFERENCE TO RELATED APPLICATIONS

This application claims priority to U.S. Provisional Patent Application No. 62/773,931, filed on Nov. 30, 2018, U.S. Provisional Patent Application No. 62/775,141, filed on Dec. 4, 2018, and U.S. Provisional Patent Application No. 62/828,041, filed on Apr. 2, 2019. The contents of each of these applications are incorporated herein by reference in their entireties.

TECHNICAL FIELD

The present disclosure in some embodiments relates to the use of platelets, platelet derivatives, or thrombosomes (e.g., freeze-dried platelet derivatives) as biological carriers of cargo, such as pharmaceutical drugs, also referred to herein as drug-loaded platelets, platelet derivatives, or thrombosomes. Also provided herein in some embodiments are methods of preparing platelets, platelet derivatives, or thrombosomes loaded with the drug of interest.

The present disclosure relates to the field of blood and blood products. More specifically, it relates to platelets, cryopreserved platelets, and/or lyopreserved platelet compositions, including those containing stabilized platelets or compositions derived from platelets. The drug-loaded platelets can be stored under typical ambient conditions, refrigerated, cryopreserved, for example with dimethyl sulfoxide (DMSO), and/or lyophilized after stabilization (e.g., thrombosomes)

BACKGROUND

Blood is a complex mixture of numerous components. In general, blood can be described as comprising four main parts: red blood cells, white blood cells, platelets, and plasma. The first three are cellular or cell-like components, whereas the fourth (plasma) is a liquid component comprising a wide and variable mixture of salts, proteins, and other factors necessary for numerous bodily functions. The components of blood can be separated from each other by various methods. In general, differential centrifugation is most commonly used currently to separate the different components of blood based on size and, in some applications, density.

Unactivated platelets, which are also commonly referred to as thrombocytes, are small, often irregularly-shaped (e.g., discoidal or ovoidal) megakaryocyte-derived components of blood that are involved in the clotting process. They aid in protecting the body from excessive blood loss due not only to trauma or injury, but to normal physiological activity as well. Platelets are considered crucial in normal hemostasis, providing the first line of defense against blood escaping from injured blood vessels. Platelets generally function by adhering to the lining of broken blood vessels, in the process becoming activated, changing to an amorphous shape, and interacting with components of the clotting system that are present in plasma or are released by the platelets themselves or other components of the blood. Purified platelets have found use in treating subjects with low platelet count (thrombocytopenia) and abnormal platelet function (thrombasthenia). Concentrated platelets are often used to control bleeding after injury or during acquired platelet function defects or deficiencies, for example those occurring during surgery and those due to the presence of platelet inhibitors.

Loading platelets with pharmaceutical drugs may allow targeted delivery of the drugs to sites of interest. Further, drug-loaded platelets may be lyophilized or cryopreserved to allow for long-term storage. In some embodiments the loading of a drug in the platelets mitigates systemic side effects associated with the drug and lowers the threshold of therapeutic dose necessary by facilitating targeted treatment at site of interest. See, Xu P., et. al., Doxorubicin-loaded platelets as a smart drug delivery system: An improved therapy for lymphoma, *Scientific Reports*, 7, Article Number: 42632, (2017), which is incorporated by reference herein in its entirety.

SUMMARY OF THE INVENTION

In some embodiments provided herein is a method of preparing cargo-loaded platelets, cargo-loaded platelet derivatives, or cargo-loaded thrombosomes (e.g., freeze-dried platelet derivatives), comprising:
  treating platelets, platelet derivatives, or thrombosomes with a cargo and with at least one loading agent and optionally one or more plasticizers such as organic solvents, such as organic solvents selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof,
to form the cargo-loaded platelets, cargo-loaded platelet derivatives, or cargo-loaded thrombosomes.

In some embodiments, the method of preparing cargo-loaded platelets can include treating the platelets, the platelet derivatives, and/or the thrombosomes with the cargo with one loading agent. In some embodiments, the method of preparing cargo-loaded platelets, cargo-loaded platelet derivatives, or cargo-loaded thrombosomes can include treating the platelets, the platelet derivatives, or the thrombosomes with the cargo with multiple loading agents.

In some embodiments, suitable organic solvents include, but are not limited to alcohols, esters, ketones, ethers, halogenated solvents, hydrocarbons, nitriles, glycols, alkyl nitrates, water or mixtures thereof. In some embodiments, suitable organic solvents includes, but are not limited to methanol, ethanol, n-propanol, isopropanol, acetic acid, acetone, methyl ethyl ketone, methyl isobutyl ketone, methyl acetate, ethyl acetate, isopropyl acetate, tetrahydrofuran, isopropyl ether (IPE), tert-butyl methyl ether, dioxane (e.g., 1,4-dioxane), acetonitrile, propionitrile, methylene chloride, chloroform, toluene, anisole, cyclohexane, hexane, heptane, ethylene glycol, nitromethane, dimethylformamide, dimethyl sulfoxide, N-methyl pyrrolidone, dimethylacetamide, and combinations thereof. The presence of organic solvents, such as ethanol, can be beneficial in the processing of platelets, platelet derivatives, and/or thrombosomes. In particular, the organic solvent may open up and/or increase the flexibility of the plasma membrane of the platelets, platelet derivatives, and/or thrombosomes, which allows a higher amount of cargo (e.g., drug) to be loaded into the platelets, platelet derivatives, and/or thrombosomes. In some embodiments, the organic solvent can aid in solubilizing molecules to be loaded.

In some embodiments provided herein is a method of preparing drug-loaded platelets, drug-loaded platelet derivatives, or drug-loaded thrombosomes, comprising:

treating platelets, platelet derivatives, or thrombosomes with a drug and with a loading buffer comprising a base, a loading agent, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof, to form the drug-loaded platelets, the drug-loaded platelet derivatives, or the drug-loaded thrombosomes.

In some embodiments provided herein is a method of preparing cargo-loaded platelets, cargo-loaded platelet derivatives, or cargo-loaded thrombosomes, comprising:

treating platelets, platelet derivatives, or thrombosomes with a cargo and with a loading buffer comprising a salt, a base, a loading agent, and optionally at least one organic solvent to form the cargo-loaded platelets, cargo-loaded platelet derivatives, or the cargo-loaded thrombosomes.

In some embodiments provided herein is a method of preparing cargo-loaded platelets, cargo-loaded platelet derivatives, or cargo-loaded thrombosomes, comprising:

treating platelets, platelet derivatives, or thrombosomes with a cargo and with a loading agent and optionally at least one organic solvent to form the cargo-loaded platelets, the cargo-loaded platelet derivatives, or the cargo-loaded thrombosomes.

In some embodiments provided herein is a method of preparing drug-loaded platelets, drug-loaded platelet derivatives, or drug-loaded thrombosomes, comprising:

treating platelets, platelet derivatives, or thrombosomes with a drug and with a loading buffer comprising a base, a loading agent, and optionally at least one organic solvent to form the drug-loaded platelets, the drug-loaded platelet derivatives, or the drug-loaded thrombosomes.

In some embodiments provided herein is a method of preparing drug-loaded platelets, drug-loaded platelet derivatives, or drug-loaded thrombosomes, comprising:

treating platelets, platelet derivatives, or thrombosomes with a drug and with a loading buffer comprising a salt, a base, a loading agent, and optionally at least one organic solvent to form the drug-loaded platelets, the drug-loaded platelet derivatives, or the drug-loaded thrombosomes.

In some embodiments provided herein is a method of preparing drug-loaded platelets, drug-loaded platelet derivatives, or drug-loaded thrombosomes, comprising:

a) providing platelets, platelet derivatives, or thrombosomes; and b) treating the platelets, the platelet derivatives, or the thrombosomes with a drug and with a loading buffer comprising a salt, a base, a loading agent, and optionally at least one organic solvent to form the drug-loaded platelets, drug-loaded platelet derivatives, or the drug-loaded thrombosomes.

In some embodiments, the method further comprises cryopreserving the drug-loaded platelets, drug-loaded platelet derivatives, or the drug-loaded thrombosomes. In some embodiments, the method further comprises cold storing the drug-loaded platelets, drug-loaded platelet derivatives, or the drug-loaded thrombosomes. In some embodiments, the method further comprises drying the drug-loaded platelets or the drug-loaded platelet derivatives. In some embodiments, the method further comprises freeze-drying the drug-loaded platelets or the drug-loaded platelet derivatives. In such embodiments, the method may further comprise rehydrating the drug-loaded platelets, drug-loaded platelet derivatives, or drug-loaded thrombosomes obtained from the drying step.

In some embodiments, the method that further comprises drying the drug-loaded platelets or drug-loaded platelet derivatives and rehydrating the drug-loaded platelets or the drug-loaded platelet derivatives obtained from the drying step provides rehydrated platelets or platelet derivatives comprising at least 10% of the amount of the drug of step (b).

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or platelet derivatives comprising from about 1 nM to about 100 mM, such as about 10 nM to about 10 mM, such as about 100 nM to 1 mM, of the drug.

In some embodiments, the platelets, platelet derivatives, or thrombosomes are treated with the drug and with the buffer sequentially, in either order.

Thus, in some embodiments provided herein is a method of preparing drug-loaded platelets, drug-loaded platelet derivatives, or drug-loaded thrombosomes, comprising:

(1) treating platelets, platelet derivatives, or thrombosomes with a drug to form a first composition; and (2) treating the first composition with a buffer comprising a salt, a base, a loading agent, and optionally at least one organic solvent to form the drug-loaded platelets, drug-loaded platelet derivatives, or drug-loaded thrombosomes.

In some embodiments of the methods of preparing cargo-loaded platelets, such as drug-loaded platelets, as provided herein, the methods do not comprise treating platelets, platelet derivatives, or thrombosomes with ethanol.

In some embodiments of the methods of preparing cargo-loaded platelets, such as drug-loaded platelets, as provided herein, the methods do not comprise treating platelets, platelet derivatives, or thrombosomes with a solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof.

In some embodiments of the methods of preparing cargo-loaded platelets, such as drug-loaded platelets, as provided herein, the methods do not comprise treating platelets, platelet derivatives, or thrombosomes with an organic solvent.

In some embodiments of the methods of preparing cargo-loaded platelets, such as drug-loaded platelets, as provided herein, the methods do not comprise treating platelets, platelet derivatives, or thrombosomes with a solvent.

In some embodiments of the methods of preparing cargo-loaded platelets, such as drug-loaded platelets, as provided herein, the methods comprise treating platelets, platelet derivatives, or thrombosomes with a solvent, such as an organic solvent, such as organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof, such as ethanol.

In some embodiments, the method further comprises drying the drug-loaded platelets or the drug-loaded platelet derivatives obtained in step (2). In some embodiments, the method further comprises cryopreserving, lyopreserving (e.g., freeze-drying) the drug-loaded platelets or the drug-loaded platelet derivatives. In some embodiments, the method further comprises cold storing the drug-loaded platelets, the drug-loaded platelet derivatives, the drug-loaded thrombosomes, or compositions containing drug-loaded platelets at suitable storage temperatures, such as standard room temperature storing (e.g., storing at a temperature ranging from about 20 to about 30° C.) or cold storing (e.g., storing at a temperature ranging from about 1 to about 10° C.). In some embodiments, the method further comprises cryopreserving, freeze-drying, thawing, rehydrating, and combinations thereof, the drug loaded platelets, the drug-loaded platelet derivatives, or the drug-loaded thrombosomes. For example, in such embodiments, the method may further comprise rehydrating the drug-loaded platelets, the drug-loaded platelet derivatives, or the drug-loaded thrombosomes obtained from the drying step.

In some embodiments, the method that further comprises drying the drug-loaded platelets or drug-loaded platelet derivatives and rehydrating the drug-loaded platelets or the drug-loaded platelet derivatives obtained from the drying step provides rehydrated platelets or platelet derivatives comprising at least 10% of the amount of the drug of step (1).

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or platelet derivatives comprising from about 1 nM to about 1000 mM, such as about 10 nM to about 100 mM, such as about 100 nM to 10 mM, of the drug of step (1).

In some embodiments provided herein is a method of preparing drug-loaded platelets, drug-loaded platelet derivatives, or drug-loaded thrombosomes, comprising:
(1) treating the platelets, platelet derivatives, or thrombosomes with a buffer comprising a salt, a base, a loading agent, and optionally ethanol, to form a first composition; and
(2) treating the first composition with a drug, to form the drug-loaded platelets, the drug-loaded platelet derivatives, or the drug-loaded thrombosomes.

In some embodiments, the method further comprises drying the drug-loaded platelets, the drug-loaded platelet derivatives, or the drug-loaded thrombosomes obtained in step (2). In some embodiments, the method further comprises freeze-drying the drug-loaded platelets or the drug-loaded platelet derivatives. In such embodiments, the method may further comprise rehydrating the drug-loaded platelets or the drug-loaded platelet derivatives obtained from the drying step.

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or platelet derivatives comprising at least 10% of the amount of the drug of step (2).

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or thrombosomes comprising from about 1 nM to about 1000 mM, such as about 10 nM to about 10 mM, such as about 100 nM to 1 mM, of the drug of step (2).

In some embodiments, the platelets or thrombosomes are treated with the drug and with the buffer concurrently.

Thus, in some embodiments provided herein is a method of preparing drug-loaded platelets, drug-loaded platelet derivatives, or the drug-loaded thrombosomes, comprising:
treating the platelets, the platelet derivatives, or the thrombosomes with a drug in the presence of a buffer comprising a salt, a base, a loading agent, and optionally ethanol, to form the drug-loaded platelets, the drug-loaded platelet derivatives, or the drug-loaded thrombosomes.

In some embodiments, the method further comprises drying the drug-loaded platelets or the drug-loaded platelet derivatives. In some embodiments, the method further comprises freeze-drying the drug-loaded platelets or the drug-loaded platelet derivatives. In such embodiments, the method may further comprise rehydrating the drug-loaded platelets or the drug-loaded platelet derivatives obtained from the drying step.

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or the thrombosomes comprising at least 10% of the amount of the drug prior to loading.

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or thrombosomes comprising from about 1 nM to about 1000 mM, such as about 10 nM to about 10 mM, such as about 100 nM to 1 mM, of the drug.

In some embodiments, platelets, platelet derivatives, or thrombosomes are pooled from a plurality of donors. Such platelets, platelet derivatives, and thrombosomes pooled from a plurality of donors may be also referred herein to as pooled platelets, platelet derivatives, or thrombosomes. In some embodiments, the donors are more than 5, such as more than 10, such as more than 20, such as more than 50, such as up to about 100 donors. In some embodiments, the donors are from about 5 to about 100, such as from about 10 to about 50, such as from about 20 to about 40, such as from about 25 to about 35.

Thus, provided herein in some embodiments is a method of preparing drug-loaded platelets, drug-loaded platelet derivatives, or drug-loaded thrombosomes comprising
A) pooling platelets, platelet derivatives, or thrombosomes from a plurality of donors; and
B) treating the platelets, platelet derivatives, or thrombosomes from step (A) with a drug and with a loading buffer comprising a salt, a base, a loading agent, and optionally ethanol, to form the drug-loaded platelets, the drug-loaded platelet derivatives, or the drug-loaded thrombosomes.

In some embodiments, the method further comprises drying the drug-loaded platelets or the drug-loaded platelet derivatives obtained in step (B). In some embodiments, the method further comprises freeze-drying the drug-loaded platelets or the drug-loaded platelet derivatives. In such embodiments, the method may further comprise rehydrating the drug-loaded platelets or the drug-loaded platelet derivatives obtained from the drying step.

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or rehydrated platelet derivatives comprising at least 10% of the amount of the drug of step (B).

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or rehydrated platelet derivatives comprising from about 1 nM to about 1000 mM, such as about 10 nM to about 10 mM, such as about 100 nM to 1 mM, of the drug of step (B).

In some embodiments, the pooled platelets, platelet derivatives, or thrombosomes are treated with the drug and with the buffer sequentially, in either order.

Thus, provided herein in some embodiments is a method of preparing drug-loaded platelets, drug-loaded platelet derivatives, or drug-loaded thrombosomes comprising:
A) pooling platelets, platelet derivatives, or thrombosomes from a plurality of donors; and B)
   (1) treating the platelets, platelet derivatives, or thrombosomes from step (A) with a drug to form a first composition; and
   (2) treating the first composition with a buffer comprising a salt, a base, a loading agent, and optionally ethanol, to form the drug-loaded platelets, drug-loaded platelet derivatives, or drug-loaded thrombosomes.

In some embodiments, the method further comprises drying the drug-loaded platelets or the drug-loaded platelet derivatives obtained in step (B)(2). In some embodiments, the method further comprises freeze-drying the drug-loaded platelets or the drug-loaded platelet derivatives. In such embodiments, the method may further comprise rehydrating the drug-loaded platelets or the drug-loaded platelet derivatives obtained from the drying step.

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or rehydrated platelet derivatives comprising at least 10% of the amount of the drug of step (B)(1).

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or platelet derivatives comprising from about 1 nM to about 1000 mM, such as about 10 nM to about 10 mM, such as about 100 nM to 1 mM, of the drug of step (B)(1).

Thus, provided herein in some embodiments is a method of preparing drug-loaded platelets, drug-loaded platelet derivatives, or drug-loaded thrombosomes comprising:
A) pooling platelets, platelet derivatives, or thrombosomes from a plurality of donors; and B)
   (1) treating the platelets, the platelet derivatives, or the thrombosomes from step (A) with a buffer comprising a salt, a base, a loading agent, and optionally ethanol, to form a first composition; and
   (2) treating the first composition with a drug to form the drug-loaded platelets, the drug-loaded platelet derivatives, or the drug-loaded thrombosomes.

In some embodiments, the method further comprises drying the drug-loaded platelets or the drug-loaded platelet derivatives obtained in step (B)(2). In some embodiments, the method further comprises freeze-drying the drug-loaded platelets or the drug-loaded platelet derivatives. In such embodiments, the method may further comprise rehydrating the drug-loaded platelets or the drug-loaded platelet derivatives obtained from the drying step.

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or thrombosomes comprising at least 10% of the amount of the drug of step (B)(2).

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or thrombosomes comprising from about 1 nM to about 1000 mM, such as about 10 nM to about 10 mM, such as about 100 nM to 1 mM, of the drug of step (B)(2).

In some embodiments, the pooled platelets, platelet derivatives, or thrombosomes are treated with the drug and with the buffer concurrently.

Thus, in some embodiments provided herein is a method of preparing drug-loaded platelets, drug-loaded platelet derivatives, or drug-loaded thrombosomes, comprising:
A) pooling platelets, platelet derivatives, or thrombosomes from a plurality of donors; and
B) treating the platelets, the platelet derivatives, or the thrombosomes with a drug in the presence of a buffer comprising a salt, a base, a loading agent, and optionally ethanol, to form the drug-loaded platelets, the drug-loaded platelet derivatives, or the drug-loaded thrombosomes.

In some embodiments, the method further comprises drying the drug-loaded platelets or the drug-loaded platelet derivatives obtained in step (B). In some embodiments, the method further comprises freeze-drying the drug-loaded platelets or the drug-loaded platelet derivatives. In such embodiments, the method may further comprise rehydrating the drug-loaded platelets or the drug-loaded platelet derivatives obtained from the drying step.

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or thrombosomes comprising at least 10% of the amount of the drug of step (B).

In some embodiments, the method that further comprises drying the drug-loaded platelets or the drug-loaded platelet derivatives and rehydrating the drug-loaded platelets or the drug-loaded platelet derivatives obtained from the drying step provides rehydrated platelets or thrombosomes comprising from about 1 nM to about 1000 mM, such as about 10 nM to about 10 mM, such as about 100 nM to 1 mM, of the drug of step (B).

In some embodiments, the methods of preparing drug-loaded platelets, drug-loaded platelet derivatives, or drug-loaded thrombosomes that comprise pooling platelets, platelet derivatives, or thrombosomes from a plurality of donors comprise a viral inactivation step.

In some embodiments, the methods of preparing drug-loaded platelets, drug-loaded platelet derivatives, or drug-loaded thrombosomes that comprise pooling platelets, platelet derivatives, or thrombosomes from a plurality of donors do not comprise a viral inactivation step.

In some embodiments, the platelets, the platelet derivatives, or the thrombosomes are loaded with the drug in a period of time of 5 minutes to 48 hours, such as 10 minutes to 24 hours, such as 20 minutes to 12 hours, such as 30 minutes to 6 hours, such as 1 hour to 3 hours, such as about 2 hours. In some embodiments, a concentration of drug from about 1 nM to about 1000 mM, such as about 10 nM to about 10 mM, such as about 100 nM to 1 mM, is loaded in a period of time of 5 minutes to 48 hours, such as 10 minutes to 24 hours, such as 20 minutes to 12 hours, such as 30 minutes to 6 hours, such as 1 hour minutes to 3 hours, such as about 2 hours.

In some embodiments provided herein are drug-loaded platelets, drug-loaded platelet derivatives, or drug-loaded thrombosomes prepared by a method as disclosed herein. In some embodiments provided herein are rehydrated platelets, platelet derivatives, or thrombosomes prepared by a method as disclosed herein.

In some embodiments provided herein are drug-loaded platelets, drug-loaded platelet derivatives, or drug-loaded thrombosomes prepared with Prostaglandin E1 (PGE1) or Prostacyclin. In some embodiments provided herein are drug-loaded platelets, drug-loaded platelet derivatives, or drug-loaded thrombosomes that are not prepared with Prostaglandin E1 (PGE1) or Prostacyclin.

In some embodiments provided herein are drug-loaded platelets, drug-loaded platelet derivatives, or drug-loaded thrombosomes prepared with a chelating agent such as EGTA. In some embodiments provided herein are drug-loaded platelets, drug-loaded platelet derivatives, or drug-loaded thrombosomes that are not prepared with a chelating agent such as EGTA.

In some embodiments provided herein the method includes treating the first composition with Prostaglandin 1 (PGE1) or Prostacyclin. In some embodiments provided herein the method does not include treating the first composition with Prostaglandin 1 (PGE1) or Prostacyclin.

In some embodiments provided herein the method includes treating the first composition with a chelating agent such as EGTA. In some embodiments provided herein the method does not include treating the first composition with a chelating agent such as EGTA.

In some embodiments provided herein are drug-loaded platelets, drug-loaded platelet derivatives, or drug-loaded thrombosomes prepared with an anti-aggregation agent.

In some embodiments provided herein are drug-loaded platelets, drug-loaded platelet derivatives, or drug-loaded thrombosomes prepared with an anti-aggregation agent such as GPIIb/IIIa inhibitor. In some embodiments the GPIIb/IIIa inhibitor is GR144053. In some embodiments, GR144053 is present at a concentration of at least 1.2 µM.

In some embodiments provided herein are drug-loaded platelets, drug-loaded platelet derivatives, or drug-loaded thrombosomes prepared with an anti-aggregation agent before being treated with the drug. In some embodiments provided herein are drug-loaded platelets, drug-loaded platelet derivatives, or drug-loaded thrombosomes prepared with anti-aggregation agents concurrently with the drug.

In some embodiments provided herein are drug-loaded platelets, drug-loaded platelet derivatives, or drug-loaded thrombosomes prepared with a drug where the drug is a drug for the treatment of cancer. In some embodiments provided herein the cancer is hemangiosarcoma.

In some embodiments provided herein the drug for the treatment of cancer is doxorubicin. In some embodiments, the drug for the treatment of hemangiosarcoma is doxorubicin.

In some embodiments provided herein the cancer includes hemangiosarcoma. In some embodiments provided herein the drug is a drug for the treatment of hemangiosarcoma including doxorubicin.

In some embodiments provided herein the drug for the treatment of cancer is paclitaxel.

In some embodiments provided herein the drug for the treatment of cancer is a PARP inhibitor. In some embodiments provided herein the PAPR inhibitor is olaparib.

Drug-loaded platelets, drug-loaded platelet derivatives, or drug-loaded thrombosomes may shield the drug from exposure in circulation, thereby reducing or eliminating systemic toxicity (e.g. cardiotoxicity) associated with the drug. Drug-loaded platelets, drug-loaded platelet derivatives, or drug-loaded thrombosomes may also protect the drug from metabolic degradation or inactivation. Drug delivery with drug-loaded platelets, drug-loaded platelet derivatives, or drug-loaded thrombosomes may therefore be advantageous in treatment of diseases such as cancer, since drug-loaded platelets, drug-loaded platelet derivatives, or drug-loaded thrombosomes facilitate targeting of cancer cells while mitigating systemic side effects. Drug-loaded platelets, drug-loaded platelet derivatives, or drug-loaded thrombosomes may be used in any therapeutic setting in which expedited healing process is required or advantageous. Potential applications include, for example, targeted depletion of cancer cells with chemotherapy drugs.

Accordingly, in some embodiments, provided herein is a method of treating a disease as disclosed herein, comprising administering drug-loaded platelets, drug-loaded platelet derivatives, or drug-loaded thrombosomes as disclosed herein. Accordingly, in some embodiments, provided herein is a method of treating a disease as disclosed herein, comprising administering cold stored, room temperature stored, cryopreserved thawed, rehydrated, and/or lyophilized platelets, platelet derivatives, or thrombosomes as disclosed herein. In some embodiments, the disease is cancer.

DESCRIPTION OF DRAWINGS

FIGS. 6A and 6B provide a comparison of doxosome (liposome encapsulated doxorubicin) loading efficiency in platelets between conventional HMT buffer (Protocol 3, shown in continuous line) and trehalose-containing loading buffer (Protocol 4, shown in individual points). FIG. 6A shows platelets with CD42b antibodies, while FIG. 6B shows platelets without CD42b.

FIG. 7 shows the correlation between fluorescence and concentration of doxorubicin.

DETAILED DESCRIPTION

Figure 1:
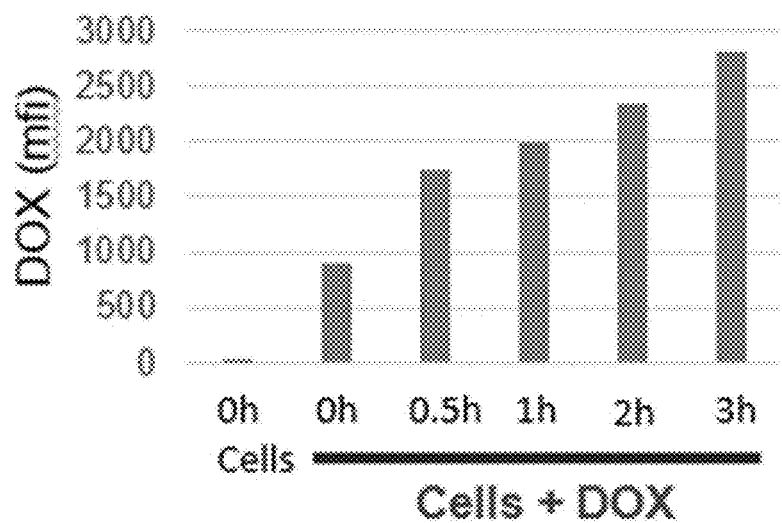
FIG. 1 shows resulting amounts of doxorubicin load in platelets as a function of incubation time when evaluated by flow cytometry.

Unless defined otherwise, all technical and scientific terms used herein have the same meaning as commonly understood by one of ordinary skill in the art to which the term belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the term "platelet" can include whole platelets, fragmented platelets, platelet derivatives, or thrombosomes. Thus, for example, reference to "drug-loaded platelets" may be inclusive of drug-loaded platelets as well as drug-loaded platelet derivatives or drug-loaded thrombosomes, unless the context clearly dictates a particular form.

As used herein and in the appended claims, the singular forms "a", "an", and "the" include plural referents unless the context clearly dictates otherwise. Thus, for example, reference to "a platelet" includes a plurality of such platelets. Furthermore, the use of terms that can be described using equivalent terms include the use of those equivalent terms. Thus, for example, the use of the term "subject" is to be understood to include the terms "patient", "individual" and other terms used in the art to indicate one who is subject to a treatment.

In some embodiments, rehydrating the drug-loaded platelets comprises adding to the platelets an aqueous liquid. In some embodiments, the aqueous liquid is water. In some embodiments, the aqueous liquid is an aqueous solution. In some embodiments, the aqueous liquid is a saline solution. In some embodiments, the aqueous liquid is a suspension.

In some embodiments, the rehydrated platelets have coagulation factor levels showing all individual factors (e.g., Factors VII, VIII and IX) associated with blood clotting at 40 international units (IU) or greater.

In some embodiments, the dried platelets, such as freeze-dried platelets, have less than about 10%, such as less than about 8%, such as less than about 6%, such as less than about 4%, such as less than about 2%, such as less than about 0.5% crosslinking of platelet membranes via proteins and/or lipids present on the membranes. In some embodiments, the rehydrated platelets, have less than about 10%, such as less than about 8%, such as less than about 6%, such as less than about 4%, such as less than about 2%, such as less than about 0.5% crosslinking of platelet membranes via proteins and/or lipids present on the membranes.

In some embodiments, the drug-loaded platelets and the dried platelets, such as freeze-dried platelets, having a particle size (e.g., diameter, max dimension) of at least about 0.2 μm (e.g., at least about 0.3 μm, at least about 0.4 μm, at least about 0.5 μm, at least about 0.6 μm, at least about 0.7 μm, at least about 0.8 μm, at least about 0.9 μm, at least about 1.0 μm, at least about 1.0 μm, at least about 1.5 μm, at least about 2.0 μm, at least about 2.5 μm, or at least about 5.0 μm). In some embodiments, the particle size is less than about 5.0 μm (e.g., less than about 2.5 μm, less than about 2.0 μm, less than about 1.5 μm, less than about 1.0 μm, less than about 0.9 μm, less than about 0.8 μm, less than about 0.7 μm, less than about 0.6 μm, less than about 0.5 μm, less than about 0.4 μm, or less than about 0.3 μm). In some embodiments, the particle size is from about 0.3 μm to about 5.0 μm (e.g., from about 0.4 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm).

In some embodiments, at least 50% (e.g., at least about 55%, at least about 60%, at least about 65%, at least about 70%, at least about 75%, at least about 80%, at least about 85%, at least about 90%, at least about 95%, or at least about 99%) of platelets and/or the dried platelets, such as freeze-dried platelets, have a particle size in the range of about 0.3 μm to about 5.0 μm (e.g., from about 0.4 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm). In some embodiments, at most 99% (e.g., at most about 95%, at most about 80%, at most about 75%, at most about 70%, at most about 65%, at most about 60%, at most about 55%, or at most about 50%) of platelets and/or the dried platelets, such as freeze-dried platelets, are in the range of about 0.3 μm to about 5.0 μm (e.g., from about 0.4 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm). In some embodiments, about 50% to about 99% (e.g., about 55% to about 95%, about 60% to about 90%, about 65% to about 85, about 70% to about 80%) of platelets and/or the dried platelets, such as freeze-dried platelets, are in the range of about 0.3 μm to about 5.0 μm (e.g., from about 0.4 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm).

In some embodiments, platelets are isolated prior to treating the platelets with a drug.

Accordingly, in some embodiments, the method for preparing drug-loaded platelets comprises:
  a) isolating platelets, for example in a liquid medium; and
  b) treating the platelets with a drug and with a loading buffer comprising a salt, a base, a loading agent, and optionally ethanol, to form the drug-loaded platelets.

Accordingly, in some embodiments, the method for preparing drug-loaded platelets comprises:
  a) isolating platelets, for example in a liquid medium;
  b) treating the platelets with a drug to form a first composition; and
  c) treating the first composition with a buffer comprising a salt, a base, a loading agent, and optionally at least one organic solvent to form the drug-loaded platelets.

In some embodiments, suitable organic solvents include, but are not limited to alcohols, esters, ketones, ethers, halogenated solvents, hydrocarbons, nitriles, glycols, alkyl nitrates, water or mixtures thereof. In some embodiments, suitable organic solvents includes, but are not limited to methanol, ethanol, n-propanol, isopropanol, acetic acid, acetone, methyl ethyl ketone, methyl isobutyl ketone, methyl acetate, ethyl acetate, isopropyl acetate, tetrahydrofuran, isopropyl ether (IPE), tert-butyl methyl ether, dioxane (e.g., 1,4-dioxane), acetonitrile, propionitrile, methylene chloride, chloroform, toluene, anisole, cyclohexane, hexane, heptane, ethylene glycol, nitromethane, dimethylformamide, dimethyl sulfoxide, N-methyl pyrrolidone, dimethylacetamide, and combinations thereof.

Accordingly, in some embodiments, the method for preparing drug-loaded platelets comprises:
  a) isolating platelets, for example in a liquid medium;
  b) treating the platelets with a buffer comprising a salt, a base, a loading agent, and optionally at least one organic solvent, to form a first composition; and
  c) treating the first composition with a drug, to form the drug-loaded platelets.

In some embodiments, no solvent is used. Thus, in some embodiments, the method for preparing drug-loaded platelets comprises:
  a) isolating platelets, for example in a liquid medium; and
  b) treating the platelets with a drug and with a loading buffer comprising a salt, a base, and a loading agent, to form the drug-loaded platelets,
    wherein the method does not comprise treating the platelets with an organic solvent such as ethanol.

Thus, in some embodiments, the method for preparing drug-loaded platelets comprises:
  a) isolating platelets, for example in a liquid medium;
  b) treating the platelets with a drug to form a first composition; and
  c) treating the first composition with a buffer comprising a salt, a base, and a loading agent, to form the drug-loaded platelets,
    wherein the method does not comprise treating the platelets with an organic solvent such as ethanol and the method does not comprise treating the first composition with an organic solvent such as ethanol.

Thus, in some embodiments, the method for preparing drug-loaded platelets comprises:
  a) isolating platelets, for example in a liquid medium;
  b) treating the platelets with a buffer comprising a salt, a base, and a loading agent, to form a first composition; and
  c) treating the first composition with a drug, to form the drug-loaded platelets.
    wherein the method does not comprise treating the platelets with an organic solvent such as ethanol and the method does not comprise treating the first composition with an organic solvent such as ethanol.

In some embodiments, isolating platelets comprises isolating platelets from blood.

In some embodiments, platelets are donor-derived platelets. In some embodiments, platelets are obtained by a process that comprises an apheresis step.

In some embodiments, platelets are derived in vitro. In some embodiments, platelets are derived or prepared in a culture prior to treating the platelets with a drug. In some embodiments, preparing the platelets comprises deriving or growing the platelets from a culture of megakaryocytes. In some embodiments, preparing the platelets comprises deriving or growing the platelets (or megakaryocytes) from a culture of human pluripotent stem cells (PCSs), including embryonic stem cells (ESCs) and/or induced pluripotent stem cells (iPSCs).

Accordingly, in some embodiments, the method for preparing drug-loaded platelets comprises:
a) preparing platelets; and
b) treating the platelets with a drug and with a loading buffer comprising a salt, a base, a loading agent, and optionally at least one organic solvent, to form the drug-loaded platelets.

Accordingly, in some embodiments, the method for preparing drug-loaded platelets comprises:
a) preparing platelets;
b) treating the platelets with a drug to form a first composition; and
c) treating the first composition with a buffer comprising a salt, a base, a loading agent, and optionally at least one organic solvent, to form the drug-loaded platelets.

Accordingly, in some embodiments, the method for preparing drug-loaded platelets comprises:
a) preparing platelets;
b) treating the platelets with a buffer comprising a salt, a base, a loading agent, and optionally at least one organic solvent, to form a first composition; and
c) treating the first composition with a drug, to form the drug-loaded platelets.

In some embodiments, no solvent is used. Thus, in some embodiments, the method for preparing drug-loaded platelets comprises:
a) preparing platelets; and
b) treating the platelets with a drug and with a loading buffer comprising a salt, a base, and a loading agent, to form the drug-loaded platelets,
wherein the method does not comprise treating the platelets with an organic solvent such as ethanol.

Thus, in some embodiments, the method for preparing drug-loaded platelets comprises:
a) preparing platelets;
b) treating the platelets with a drug to form a first composition; and
c) treating the first composition with a buffer comprising a salt, a base, and a loading agent, to form the drug-loaded platelets,
wherein the method does not comprise treating the platelets with an organic solvent such as ethanol and the method does not comprise treating the first composition with an organic solvent such as ethanol.

Thus, in some embodiments, the method for preparing drug-loaded platelets comprises:
a) preparing platelets;
b) treating the platelets with a buffer comprising a salt, a base, and a loading agent, to form a first composition; and
c) treating the first composition with a drug, to form the drug-loaded platelets.
wherein the method does not comprise treating the platelets with an organic solvent such as ethanol and the method does not comprise treating the first composition with an organic solvent such as ethanol.

In some embodiments, the loading agent is a saccharide. In some embodiments, the saccharide is a monosaccharide. In some embodiments, the saccharide is a disaccharide. In some embodiments, the saccharide is a non-reducing disaccharide. In some embodiments, the saccharide is sucrose, maltose, trehalose, glucose (e.g., dextrose), mannose, or xylose. In some embodiments, the loading agent is a starch.

In some embodiments, the loading agent is a carrier protein. In some embodiments, the carrier protein is albumin. In some embodiments, the carrier protein is bovine serum albumin (BSA).

As used herein, the term "drug" refers to any agent suitable for the treatment of cancer other than a messenger RNA (mRNA), a microRNA (also known as miRNA) and/or a small interfering RNA (also known as siRNA, short interfering RNA, or silencing RNA).

As used herein, the term "mRNA" refers to a single-stranded ribonucleic acid molecule used by cells for the translation of DNA into protein. Many mRNAs are naturally-occurring, but mRNAs can also be synthesized by those of ordinary skill in the art. Mature mRNAs can vary greatly in size and composition. mRNAs are necessary components of protein synthesis after exportation from the nucleus to the cytoplasm of the cell.

As used herein, the term "microRNA" refers to a ribonucleic acid duplex that targets and silences an mRNA molecule. Many miRNAs are naturally-occurring, but miRNAs can also be synthesized by those of ordinary skill in the art. Mature miRNAs are generally 19-25 nucleotides in length, have 3' overhangs of two nucleotides, target multiple mRNAs and are typically only partially complementary to their target mRNAs. miRNAs typically function by repressing translation and facilitating mRNA degradation.

As used herein, the term "small interfering RNA" refers to a double-stranded RNA that targets and silences an mRNA molecule. Many siRNAs are naturally-occurring, but siRNAs can also be synthesized by those of ordinary skill in the art. siRNA are generally derived from strands of exogenous growing (originating from outside an organism) RNA, which is taken up by the cell and undergoes further processing. Mature siRNAs are generally 19-27 nucleotides in length, have 3' overhangs of two nucleotides at each end that can be used to "interfere" with the translation of proteins by binding to and promoting the degradation of messenger RNA at specific sequences. Each siRNA strand has a 5' phosphate group and a 3' hydroxyl (OH) group. siRNA can be produced from dsRNA or hairpin looped RNA and processed into siRNAs by the Dicer enzyme. siRNA can also be incorporated into a multi-subunit protein complex called RNA-induced silencing complex (RISC).

miRNAs and siRNAs are distinct from other types of RNA molecules including, without limitation, messenger RNA ("mRNA"), ribosomal RNA ("rRNA"), small nuclear RNA ("snRNA"), transfer RNA ("tRNA"), and short hairpin RNA ("shRNA"). rRNA, snRNA, tRNA, and shRNA are all encompassed within the term "drug" as used herein. mRNA, rRNA, snRNA, and tRNA are canonical classes of RNA molecules, the function and structure of which are well-known to those of ordinary skill in the art.

shRNAs are short linear RNA molecules, portions of which associate with each other via base pairing to form a double stranded stem region (as opposed to the fully double stranded siRNAs), resulting in a characteristic "hairpin" or loop at one end of the molecule. Unlike miRNAs and siRNAs, shRNAs are typically introduced into cells using methods that differ from the methods used for introducing miRNA and siRNA (e.g., using transfection methods). For example, shRNAs can be introduced via plasmids or, alternatively, through viral or bacterial vectors. Both of these methods are DNA-based techniques, where the shRNA is transcribed, processed by the enzyme Drosha, and then further processed into siRNAs, by the Dicer enzyme, to eventually mediate RNAi.

As used herein, "thrombosomes" (sometimes also herein called "Tsomes" or "Ts", particularly in the Examples and Figures) are platelet derivatives that have been treated with an incubating agent (e.g., any of the incubating agents described herein) and lyopreserved (e.g., freeze-dried). In some cases, thrombosomes can be prepared from pooled platelets. Thrombosomes can have a shelf life of 2-3 years in dry form at ambient temperature and can be rehydrated with sterile water within minutes for immediate infusion.

In some embodiments, the drug is selected from the group consisting of one of the following:
  i. a small molecule (that is, an organic compound having a molecular weight up to about 2 KDalton);
  ii. a protein;
  iii. an oligopeptide;
  iv. a non-miRNA nucleic acid, a non-siRNA, and/or a non-mRNA (e.g., non-miRNA, DNA, other naturally or non-naturally occurring nucleic acids, including various modifications thereof); and
  v. an aptamer.

In various methods described herein, platelets are loaded with one or more any of a variety of drugs. In some embodiments, platelets are loaded with a small molecule. For example, platelets can be loaded with one or more of vemurafenib (ZELBORAF®), dabrafenib (TAFINLAR®), encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, LXH254, trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, CS3006, WX-554, PD98059, CI1040 (PD184352), hypothemycin, FRI-20 (ON-01060), VTX-Ile, 25-OH-D3-3-BE (B3CD, bromoacetoxycalcidiol), FR-180204, AEZ-131 (AEZS-131), AEZS-136, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASNO07, FR148083, 5-7-oxozeaenol, 5-iodotubercidin, GDC0994, ONC201, buparlisib (BKM120), alpelisib (BYL719), WX-037, copanlisib (ALIQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASNO03, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, GSK2636771, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl) phenyl]-3-phenylquinoxaline, MK-2206, edelfosine, erucylphophocholine, erufosine, SR13668, OSU-A9, PH-316, PHT-427, PIT-1, DM-PIT-1, triciribine (triciribine phosphate monohydrate), API-1, N-(4-(5-(3-acetamidophenyl)-2-(2-aminopyridin-3-yl)-3H-imidazo[4,5-b] pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, MLN0128, AZD-2014, CC-223, AZD2014, CC-115, everolimus (RAD001), temsirolimus (CCI-779), ridaforolimus (AP-23573), tipifarnib, BMS-214662, L778123, L744832, FTI-277, PRI-724, CWP232291, PNU74654, PKF115-584, PKF118-744, PKF118-310, PFK222-815, CGP 049090, ZTM000990, BC21, methyl 3-{[(4-methylphenyl)sulfonyl] amino}benzoate (MSAB), AV65, iCRT3, iCRT5, iCRT14, SM04554, LGK 974, XAV939, curcumin (e.g., Meriva®), DIF-1, genistein, NSC668036, FJ9, BML-286 (3289-8625), IWP, IWP-1, IWP-2, JW55, G007-LK, pyrvinium, foxy-5, Wnt-5a, ipafricept (OMP-54F28), vantictumab (OMP-18R5), SM04690, SM04755, nutlin-3a, IWR1, JW74, okadaic acid, SB239063, SB203580, adenosine diphosphate (hydroxymethyl)pyrrolidinediol (ADP-HPD), 2-[4-(4-fluorophenyl)piperazin-1-yl]-6-methylpyrimidin-4(3H)-one, PJ34, J01-017a, IC261, PF670462, bosutinib (BOSULIF®), PHA665752, imatinib (GLEEVEC®), ICG-001, Rp-8-Br-cAMP, SDX-308, WNT974, CGX1321, ETC-1922159, AD-REIC/Dkk3, WIKI4, windorphen, NTRC 0066-0, CFI-402257, a (5,6-dihydro)pyrimido[4,5-e]indolizine, BOS172722, 563845, AZD5991, AMG 176, 483-LM, MIK665, TASIN-1 (Truncated APC Selective Inhibitor), osimertinib (AZD9291, merelectinib, TAGRISSO™), erlotinib (TARCEVA®), gefitinib (IRESSA®), neratinib (HKI-272, NERLYNX®), lapatinib (TYKERB®), vetanib (CAPRELSA®), rociletinib (CO-1686), olmutinib (OLITA™, HM61713, BI-1482694), naquotinib (ASP8273), nazartinib (EGF816, NVS-816), PF-06747775, icotinib (BPI-2009H), afatinib (BIBW 2992, GILOTRIF®), dacomitinib (PF-00299804, PF-804, PF-299, PF-299804), avitinib (AC0010), AC0010MA EAI045, canertinib (CI-1033), poziotinib (NOV120101, HM781-36B), AV-412, WZ4002, brigatinib (AP26113, ALUNBRIG®), pelitinib (EKB-569), tarloxotinib (TH-4000, PR610), BPI-15086, Hemay022, ZN-e4, tesevatinib (KDO19, XL647), YH25448, epitinib (HMPL-813), CK-101, MM-151, AZD3759, ZD6474, PF-06459988, varlintinib (ASLAN001, ARRY-334543), AP32788, HLX07, D-0316, AEE788, HS-10296, GW572016, pyrotinib (SHR1258), palbociclib, ribociclib, abemaciclib, olaparib, veliparib, iniparib, rucaparib, CEP-9722, E7016, E7449, PRN1371, BLU9931, FIIN-4, H3B-6527, NVP-BGJ398, ARQ087, TAS-120, CH5183284, Debio 1347, INCB054828, JNJ-42756493 (erdafitinib), rogaratinib (BAY1163877), FIIN-2, LY2874455, lenvatinib (E7080), ponatinib (AP24534), regorafenib (BAY 73-4506), dovitinib (TKI258), lucitanib (E3810), cediranib (AZD2171), nintedanib (OFEV®, BIM 1120), brivanib (BMS-540215), ASP5878, AZD4547, BGJ398 (infigratinib), E7090, HMPL-453, MAX-40279, XL999, orantinib (SU6668), pazopanib (VOTRIENT®), anlotinib, AL3818, PRIMA-1 (p53 reactivation induction of massive apoptosis-1), APR-246 (PRIMA-1MET), 2-sulfonylpyrimidines such as PK11007, pyrazoles such as PK7088, zinc metallochaperone-1 (ZMC1; NSC319726/ZMC 1), a thiosemicarbazone (e.g., COTI-2), CP-31398, STIMA-1 (SH Group-Targeting Compound That Induces Massive Apoptosis), MIRA-1 (NSC19630) and its analogs, e.g., MIRA-2 and MIRA-3, RITA (NSC652287), chetomin (CTM), stictic acid (NSC87511), p53R3, SCH529074, WR-1065, arsenic compounds, gambogic acid, spautin-1, YK-3-237, NSC59984, disulfiram (DSF), G418, RETRA (reactivate transcriptional activity), PD0166285, 17-AAG, geldanamycin, ganetespib, AUY922, IPI-504, vorinostat/SAHA, romidepsin/depsipeptide, HBI-8000, RG7112 (RO5045337), RO5503781, MI-773 (SAR405838), DS-3032b, AM-8553, AMG 232, MI-219, MI-713, MI-888, TDP521252, NSC279287, PXN822, ATSP-7041, spiroligomer, PK083, PK5174, PK5196, nutlin 3a, RG7388, Ro-2443, FTY-720, ceramide, OP449, vatalanib (PTK787/ZK222584), TKI-538, sunitinib (SU11248, SUTENT®), thalidomide, lenalidomide (REVLIMID®), axitinib (AG013736, INLYTA®), RXC0004, ETC-159, LGK974, WNT-059, AZD8931, AST1306, CP724714, CUDC101, TAK285, AC480, DXL-702, E-75, PX-104.1, ZW25, CP-724714, irbinitinib (ARRY-380, ONT-380), TAS0728, AST-1306, AEE-788, perlitinib (EKB-569), PKI-166, D-69491, HKI-357, AC-480 (BMS-599626), RB-200h, ARRY-334543 (ARRY-543, ASLAN001), CUDC-101, IDM-1, decitabine, cytosine arabinoside, ORY1001 (RG6016), GSK2879552, INCB059872, IMG7289, CC90011, MI1, MI2, MI3, Mi2-2 (MI-2-2), MI463, MI503, MIV-6R, EPZ004777, EPZ-5676, SGC0946, CN-SAH, SYC-522, SAH, SYC-534, MM-101, MM-102, MM-103, MM-401, WDR5-0101, WDR5-0102, WDR5-0103, OICR-9429, tivantinib (ARQ 197), golvatinib (E7050), cabozantinib (XL 184, BMS-907351), foretinib (GSK1363089), crizotinib (PF-02341066), MK-2461, BPI-9016M, TQ-B3139, MGCD265, MK-8033, capmatinib (INC280, INCB28060), tepotinib (MSC2156119J, EMD1214063), CE-35562, AMG-337, AMG-458, PHA-665725, PF-04217903, SU11274, PHA-665752, HS-10241, ARGX-111, glumetinib (SCC244), EMD 1204831, AZD6094 (savolitinib, volitinib, HMPL-504), PLB1001, ABT-700, AMG 208, INCB028060, AL2846, HTI-1066, PT2385, PT2977, 17 allylamino-17-demethoxygeldanamycin, eribulin (HALAVEN®, E389, ER-086526), ibrutinib (PCI-32675, Imbruvica®) (1-[(3R)-3-[4-amino-3-(4-phenoxyphenyl)pyrazolo[3,4-d]pyrimidin-1-yl]piperidin-1-yl] prop-2-en-1-one); AC0058 (AC0058TA); N-(3-((2-((3-fluoro-4-(4-methylpiperazin-1-yl)phenyl)amino)-7H-pyrrolo[2,3-d]pyrimidin-4-yl)oxy)phenyl)acrylamide; acalabrutinib (ACP-196, Calquence®, rINN) (4-[8-amino-3-[(2S)-1-but-2-ynoylpyrrolidin-2-yl]imidazo[1,5-a] pyrazin-1-yl]-N-pyridin-2-ylbenzamide); zanubrutinib (BGB-3111) ((7R)-2-(4-phenoxyphenyl)-7-(1-prop-2-enoylpiperidin-4-yl)-1,5,6,7-tetrahydropyrazolo[1,5-a]pyrimidine-3-carboxamide); spebrutinib (AVL-292, 1202757-89-8, Cc-292) (N-[3-[[5-fluoro-2-[4-(2-methoxyethoxy) anilino]pyrimidin-4-yl]amino]phenyl]prop-2-enamide); poseltinib (HM71224, LY3337641) (N-[3-[2-[4-(4-methylpiperazin-1-yl)anilino]furo[3,2-d]pyrimidin-4-yl]oxyphenyl]prop-2-enamide); evobrutinib (MSC 2364447, M-2951) (1-[4-[[[6-amino-5-(4-phenoxyphenyl)pyrimidin-4-yl] amino]methyl]piperidin-1-yl]prop-2-en-1-one); tirabrutinib (ONO-4059, GS-4059, ONO/GS-4059, ONO-WG-307) (1-[4-[[[6-amino-5-(4-phenoxyphenyl)pyrimidin-4-yl]amino] methyl]piperidin-1-yl]prop-2-en-1-one); vecabrutinib (SNS-062) ((3R,4S)-1-(6-amino-5-fluoropyrimidin-4-yl)-3-[(3R)-3-[3-chloro-5-(trifluoromethyl)anilino]-2-oxopiperidin-1-yl]piperidine-4-carboxamide); dasatinib (Sprycel®; BMS-354825) (N-(2-chloro-6-methylphenyl)-2-[[6-[4-(2-hydroxyethyl)piperazin-1-yl]-2-methylpyrimidin-4-yl] amino]-1,3-thiazole-5-carboxamide); PRN1008, PRN473, ABBV-105, CG'806, ARQ 531, BIIB068, AS871, CB1763, CB988, GDC-0853, RN486, GNE-504, GNE-309, BTK Max, CT-1530, CGI-1746, CGI-560, LFM A13, TP-0158, dtrmwxhs-12, CNX-774, entrectinib, nilotinib, 1-((3S,4R)-4-(3-fluorophenyl)-1-(2-methoxyethyl)pyrrolidin-3-yl)-3-(4-methyl-3-(2-methylpyridin-5-yl)-1-phenyl-1H-pyrazol-5-yl)urea, AG 879, AR-772, AR-786, AR-256, AR-618, AZ-23, AZ623, DS-6051, Go 6976, GNF-5837, GTx-186, GW 441756, LOXO-101, LOXO-195, MGCD516, PLX7486, RXDX101, TPX-0005, TSR-011, venetoclax (ABT-199, RG7601, GDC-0199), navitoclax (ABT-263), ABT-737, TW-37, sabutoclax, obatoclax, BIX-01294 (BIX), UNC0638, A-366, UNC0642, DCG066, UNC0321, BRD 4770, UNC 0224, UNC 0646, UNC0631, BIX-01338, INNO-406, KX2-391, saracatinib, PP1, PP2, ruxolitinib, lestaurtinib (CEP-701), momelotinib (GS-0387, CYT-387), pacritinib (SB1518), fedratinib (SAR302503), BI2536, BI6727, GSK461364, amsacrine, azacitidine, busulfan, carboplatin, capecitabine, chlorambucil, cisplatin, cyclophosphamide, cytarabine, dacarbazine, daunorubicin, docetaxel, doxifluridine, doxorubicin, epirubicin, etoposide, fiudarabine, floxuridine, fludarabine, fluorouracil, gemcitabine, hydroxyurea, idarubicin, ifosfamide, irinotecan, lomustine, mechlorethamine, melphalan, mercaptopurine, methotrxate, mitomycin, mitoxantrone, oxaliplatin, paclitaxel, pemetrexed, procarbazine, streptozocin, tafluposide, temozolomide, teniposide, tioguanine, topotecan, uramustine, valrubicin, vinblastine, vincristine, vindesine, and vinorelbine.

In various methods described herein, platelets are loaded with one or more any of a variety of drugs. In some embodiments, platelets are loaded with a protein (e.g., an antibody or antibody conjugate). For example, platelets can be loaded with one or more of cetuximab (ERBITUX®), necitumumab (PORTRAZZA™, IMC-11F8), panitumumab (ABX-EGF, VECTIBIX®), matuzumab (EMD-7200), nimotuzumab (h-R3, BIOMAb EGFR®), zalutumab, MDX447, OTSA 101, OTSA101-DTPA-90Y, ABBV-399, depatuxizumab (humanized mAb 806, ABT-806), depatuxizumab mafodotin (ABT-414), SAIT301, Sym004, MAb-425, Modotuximab (TAB-H49), futuximab (992 DS), zalutumumab, Sym013, AMG 595, JNJ-61186372, LY3164530, IMGN289, KL-140, RO5083945, SCT200, CPGJ602, GP369, BAY1187982, FPA144 (bemarituzumab), bevacizumab (AVASTIN®), ranibizumab, trastuzumab (HERCEPTIN®), pertuzumab (PERJETA®), trastuzumab-dkst (OGIVRI®), ado-trastuzumab emtansine (KADCYLA®, T-DM1), Zemab, DS-8201a, MFGR1877S, B-701, rilotumumab (AMG102), ficlatuzumab (AV-299), FP-1039 (GSK230), TAK701, YYB101, onartuzumab (MetMAb), ipilimumab (YERVOY®), tremelimumab (CP-675,206), pembrolizumab (KEYTRUDA®), nivolumab (OPDIVO®), atezolizumab (TECENTRIQ®), avelumab (BAVENCIO®), durvalumab (IMFINZI™), BIOO-1, BIOO-2, and BIOO-3.

In various methods described herein, platelets are loaded with one or more any of a variety of drugs. In some embodiments, platelets are loaded with an oligopeptide. For example, platelets can be loaded with one or more of RGD-SSL-Dox, LPD-PEG-NGR, PNC-2, PNC-7, RGD-PEG-Suc-PD0325901, VWCS, FWCS, p16, Bac-7-ELP-p21, Pen-ELP-p21, TAT-Bim, Poropeptide-Bax, R8-Bax, CT20p-NP, RRM-MV, RRM-IL12, PNC-27, PNC-21, PNC-28, Tat-aHDM2, Int-H1-S6A, FBA, Pen-ELP-H1, BAC1-ELP-H1, goserelin, leuprolide, Buserelin, Triptorelin, Degarelix, Pituitary adenylate cyclase activating peptide (PACAP), cilengitide, ATN-161 (AcPHSCN-NH2), TTK, LY6K, IMP-3, P16_37-63, VEGFR1-A24-1084, uMMP-2, uTIMP-1, MIC-1/GDF15, RGS6, LGRS, PGI/II, CA242, EN2, UCP2, a HER-2 peptide, MUClm, HNP1-3, L-glutamine L-tryptophan (IM862), CPAA-783-EPPT1, serum C-peptide, WT1, KIF20A, GV1001, LY6K-177, PAP-114-128, E75, SU18, SU22, ANP, TCP-1, F56, WT1, TERT572Y, disruptin, TREM-1, LFC131, BPP, TH10, BC71, RC-3095, RC-3940-II, RC-3950, (KLAKLAK)2, RGD-(KLAKLAK)2, NGR-(KLAKLAK)2, and SAH-8 (stapled peptides).

In various methods described herein, platelets are loaded with one or more any of a variety of drugs. In some embodiments, platelets are loaded with a non-miRNA nucleic acid, a non-siRNA nucleic acid, and a non-mRNA nucleic acid (e.g., non-miRNA, DNA, other naturally or non-naturally occurring nucleic acids, and polymers thereof), including various modifications thereof). For example, platelets can be loaded with one or more of SPC2996, SIRNAPLUS, ALN-HTT, ISIS-199044, custirsen (OGX-011, ISI-112989, TV-1011), ISIS-AR-2.5RX (ISIS-ARRx, AZD-5312, ISIS-AZ1Rx, ISIS-560131), ISIS-STAT3-2.5Rx (ISIS-STAT3-2.5Rx, ISIS-481464, AZD-9150), BP-100-1.01, NOX-A12 (olaptesed peqol), PNT-2258, ATL-1103, RX-0201, ACT-GRO-777, litenimod, trabedersen (AP-2009), IMO-2055, OHR-118, imetelstat, GNKG-168, RG-6061, SPC-3042, STAT3 decoys, an anti-CD22 antibody-MXD3 antisense oligonucleotide conjugate, AST-008, ASncmtRNA, an EGFRAS GPNA, ASPH-1047 (ASPH-0047), STICKY SIRNA, aganirsen, B0-110, NOX-593, Adva-R46, EZN-4482, EZN-4496, EZN-3889, EZN-3892, EZN-4150, IMO-2125 (HYB-2125), OGX-225, ATL-1101, aqatolimod, AGX-1053, AEG-35156, qataparsen, ISS-1018, CpG-1826 (ODN-1826), CpG-2216 (ODN-2216), CpG-2395, oblimersen, pbi-shRNAK-ras LP, LNA anti-miR-155, ISIS-20408, ISIS-199044, AP-11014, NOX-A50, beclanorsen, ISIS-345794, ISIS-15421, GRO-29A, LOR-2501 (GTI-2501), ISIS-7597, ISIS-3466, ISIS-2503, and GEM-231.

In various methods described herein, platelets are loaded with one or more any of a variety of drugs. In some embodiments, platelets are loaded with an aptamer. For example, platelets can be loaded with one or more of ARC126 (RNA), AX102 (RNA), SL (2)-B (DNA), RNV66 (DNA), AS1411 (DNA), FCL-II (DNA, modified form AS1411), NOX-A12 (RNA), E0727 (RNA), CL428 (RNA), KDI130 (RNA), TuTu2231 (RNA), Trimeric apt (DNA), PNDA-3 (DNA), TTA140,41 (DNA), GBI-1042 (DNA), NAS-24 (DNA), YJ-1 (RNA), AGE-apt (DNA), A-P50 (RNA), GL21.T (RNA), OPN-R3 (RNA), AGC03 (DNA), cy-apt (DNA), BC15 (DNA), A9g (RNA), ESTA (DNA), M12-23 (RNA), OX40-apt (RNA), De160 (RNA), PSMA-4-1BB-apt (RNA), CD16α/c-Met-apt (RNA), VEGF-4-1BB apt (DNA), MP7 (DNA), aptPD-L1 (DNA), R5A1 (RNA), CL-42 (RNA), CD44-EpCAM aptamer (RNA), TIM3Apt (RNA), CD40apt (RNA), AptCTLA-4 (DNA), AON-D211-Aptamer (RNA/DNA), and BN-210.

In some embodiments, a drug loaded into platelets is modified. For example, a drug can be modified to increase its stability during the platelet loading process, while the drug is loaded into the platelet, and/or after the drug's release from a platelet. In some embodiments, the modified drug's stability is increased with little or no adverse effect on its activity. For example, the modified drug can have at least 70%, 75%, 80%, 85%, 90%, 95%, 96%, 97%, 98%, 99% or more of the activity of the corresponding unmodified drug. In some embodiments, the modified drug has 100% (or more) of the activity of the corresponding unmodified drug. Various modifications that stabilize drugs are known in the art. In some embodiments, the drug is a nucleic acid, which nucleic acid is stabilized by one or more of a stabilizing oligonucleotide (see, e.g., U.S. Application Publication No. 2018/0311176), a backbone/side chain modification (e.g., a 2-sugar modification such as a 2'-fluor, methoxy, or amine substitution, or a 2'-thio (—SH), 2'-azido (—N3), or 2'-hydroxymethyl (—CH2OH) modification), an unnatural nucleic acid substitution (e.g., an S-glycerol, cyclohexenyl, and/or threose nucleic acid substitution, an L-nucleic acid substitution, a locked nucleic acid (LNA) modification (e.g., the ribose moiety of an LNA nucleotide is modified with an extra bridge connecting the 2' oxygen and 4' carbon), conjugation with PEG, a nucleic acid bond modification or replacement (e.g., a phosphorothioate bond, a methylphosphonate bond, or a phosphorodiamidate bond), a reagent or reagents (e.g., intercalating agents such as coralyne, neomycin, and ellipticine; also see US Publication Application Nos. 2018/0312903 and 2017/0198335, each of which are incorporated herein by reference in their entireties, for further examples of stabilizing reagents). In some embodiments, the drug is a polypeptide, which polypeptide is stabilized by one or more of cyclization of the peptide sequence [e.g., between side chains or ends of the peptide sequence (for example, head to tail, N-backbone to N-backbone, end to N-backbone, end to side chain, side chain to N-backbone, side chain to side chain) through disulfide, lanthionine, dicarba, hydrazine, or lactam bridges], a backbone/side chain modification, an unnatural residue substitution (e.g., a D-amino acid, an N-methyl-α-amino acid, a non-proteogenic constrained amino acid or a β-amino acid), a peptide bond modification or replacement [e.g., NH-amide alkylation, the carbonyl function of the peptide bond can be replaced by CH2 (reduced bond: —CH2-NH—), C(=S) (endothiopeptide, —C(=S)—NH—) or PO2H (phosphonamide, —P(=O)OH—NH—), the NH-amide bond can be exchanged by O (depsipeptide, —CO—O—), S (thioester, —CO—S—) or CH2 (ketomethylene, —CO—CH2-), a retro-inverso bond (—NH—CO—), a methylene-oxy bond (—CH2-), a thiomethylene bond (—CH2-S—), a carba bond (—CH2-CH2-), and a hydroxyethylene bond (—CHOH—CH2-)], a disulfide-bridged conjugation with synthetic aromatics (see e.g., Chen et al. Org Biomol Chem. 2017, 15(8):1921-1929, which is incorporated by reference herein in its entirety), blocking N- or C-terminal ends of the peptide (e.g., by N-acylation, N-pyroglutamate, or C-amidation or the addition of carbohydrate chains through, for example, glycosylation with glucose, xylose, hexose), an N-terminal esterification (phosphoester), a pegylation modification, and a reagent or reagents (see, e.g., US Publication Application No. 2017/0198335). See. e.g., Vlieghe et al. Drug Discovery Today, 2010, 15, 40-56, which is incorporated by reference herein in its entirety.

In some embodiments, a drug loaded into platelets is modified to include an imaging agent. For example, a drug can be modified with an imaging agent in order to image the drug loaded platelet in vivo. In some embodiments, a drug can be modified with two or more imaging agents (e.g., any two or more of the imaging agents described herein). In some embodiments, a drug loaded into platelets is modified with a radioactive metal ion, a paramagnetic metal ion, a gamma-emitting radioactive halogen, a positron-emitting radioactive non-metal, a hyperpolarized NMR-active nucleus, a reporter suitable for in vivo optical imaging, or a beta-emitter suitable for intravascular detection. For example, a radioactive metal ion can include, but is not limited to, positron emitters such as $^{54}$Cu, $^{48}$V, $^{52}$Fe, $^{55}$Co, $^{94}$TC or $^{68}$Ga; or gamma-emitters such as $^{171}$Tc, $^{111}$In, $^{113}$In or $^{67}$Ga. For example, a paramagnetic metal ion can include, but is not limited to Gd(III), a Mn(II), a Cu(II), a Cr(III), a Fe(III), a Co(II), a Er(II), a Ni(II), a Eu(III) or a Dy(III), an element comprising an Fe element, a neodymium iron oxide (NdFeO3) or a dysprosium iron oxide (DyFeO3). For example, a paramagnetic metal ion can be chelated to a polypeptide or a monocrystalline nanoparticle. For example, a gamma-emitting radioactive halogen can include, but is not limited to $^{123}$I, $^{131}$I or $^{77}$Br. For example, a positron-emitting radioactive non-metal can include, but is not limited to $^{11}C$, $^{13}N$, $^{15}O$, $^{17}F$, $^{18}F$, $^{75}Br$, $^{76}Br$ or $^{124}I$. For example, a hyperpolarized NMR-active nucleus can include, but is not limited to $^{13}C$, $^{15}N$, $^{19}F$, $^{29}Si$ and $^{31}P$. For example, a reporter suitable for in vivo optical imaging can include, but is not limited to any moiety capable of detection either directly or indirectly in an optical imaging procedure. For example, the reporter suitable for in vivo optical imaging can be a light scatterer (e.g., a colored or uncolored particle), a light absorber or a light emitter. For example, the reporter can be any reporter that interacts with light in the electromagnetic spectrum with wavelengths from the ultraviolet to the near infrared. For example, organic chromophoric and fluorophoric reporters include groups having an extensive delocalized electron system, e.g. cyanines, merocyanines, indocyanines, phthalocyanines, naphthalocyanines, triphenylmethines, porphyrins, pyrylium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, b/s(dithiolene) complexes, bis(benzene-dithiolate) complexes, iodoaniline dyes, b/stS.O-dithiolene) complexes. For example, the reporter can be, but is not limited to a fluorescent, a bioluminescent, or chemiluminescent polypeptide. For example, a fluorescent or chemiluminescent polypeptide is a green florescent protein (GFP), a modified GFP to have different absorption/emission properties, a luciferase, an aequorin, an obelin, a mnemiopsin, a berovin, or a phenanthridinium ester. For example, a reporter can be, but is not limited to rare earth metals (e.g., europium, samarium, terbium, or dysprosium), or fluorescent nanocrystals (e.g., quantum dots). For example, a reporter may be a chromophore that can include, but is not limited to fluorescein, sulforhodamine 101 (Texas Red), rhodamine B, rhodamine 6G, rhodamine 19, indocyanine green, Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750. For example, a beta-emitter can include, but is not limited to radio metals $^{67}Cu$, $^{89}Sr$, $^{90}Y$, $^{153}Sm$, $^{185}Re$, $^{188}Re$ or $^{192}Ir$, and non-metals $^{32}P$, $^{33}P$, $^{38}S$, $^{38}Cl$, $^{39}Cl$, $^{82}Br$ and $^{83}Br$. In some embodiments, a drug loaded into platelets can be associated with gold or other equivalent metal particles (such as nanoparticles). For example, a metal particle system can include, but is not limited to gold nanoparticles (e.g., Nanogold™).

In some embodiments, a drug loaded into platelets that is modified with an imaging agent is imaged using an imaging unit. The imaging unit can be configured to image the drug loaded platelets in vivo based on an expected property (e.g., optical property from the imaging agent) to be characterized. For example, imaging techniques (in vivo imaging using an imaging unit) that can be used, but are not limited to are: computer assisted tomography (CAT), magnetic resonance spectroscopy (MRS), magnetic resonance imaging (MRI), positron emission tomography (PET), single-photon emission computed tomography (SPECT), or bioluminescence imaging (BLI). Chen Z., et. al., Advance of Molecular Imaging Technology and Targeted Imaging Agent in Imaging and Therapy, *Biomed Res Int.*, February 13, doi: 10.1155/2014/819324 (2014) have described various imaging techniques and which is incorporated by reference herein in its entirety.

In some embodiments, such as embodiments wherein the platelets are treated with the drug and the buffer sequentially as disclosed herein, the drug may be loaded in a liquid medium that may be modified to change the proportion of media components or to exchange components for similar products, or to add components necessary for a given application.

In some embodiments the loading buffer, and/or the liquid medium, may comprise one or more of a) water or a saline solution, b) one or more additional salts, or c) a base. In some embodiments, the loading buffer, and/or the liquid medium, may comprise one or more of a) DMSO, b) one or more salts, or c) a base.

In some embodiments the loading agent is loaded into the platelets in the presence of an aqueous medium. In some embodiments the loading agent is loaded in the presence of a medium comprising DMSO. As an example, one embodiment of the methods herein comprises treating platelets with a drug and with an aqueous loading buffer comprising a salt, a base, a loading agent, and optionally at least one organic solvent, to form the cargo-loaded platelets. As an example, one embodiment of the methods herein comprises treating platelets with a drug and with a loading buffer comprising DMSO and comprising a salt, a base, a loading agent, and optionally ethanol, to form the cargo-loaded platelets.

In some embodiments the loading buffer, and/or the liquid medium, may comprise one or more salts selected from phosphate salts, sodium salts, potassium salts, calcium salts, magnesium salts, and any other salt that can be found in blood or blood products, or that is known to be useful in drying platelets, or any combination of two or more of these. Preferably, these salts are present in the composition at an amount that is about the same as is found in whole blood.

In some embodiments, the drug-loaded platelets are prepared by incubating the platelets with the drug in the liquid medium for different durations at or at different temperatures from 15-45° C., or about 37° C. (cell to drug volume ratio of 1:2).

In some embodiments, the platelets form a suspension in a liquid medium at a concentration from 10,000 platelets/μL to 10,000,000 platelets/μL, such as 50,000 platelets/μL to 2,000,000 platelets/μL, such as 100,000 platelets/μL to 500,000 platelets/μL, such as 150,000 platelets/μL to 300,000 platelets/μL, such as 200,000 platelets/μL.

In some embodiments, one or more other components may be loaded in the platelets. In some embodiments, the one or more other components may be loaded concurrently with the drug. In some embodiments, the one or more other components and the drug may be loaded sequentially in either order. Components may include an agent (e.g., an anti-aggregation agent) that reduces or prevents platelet aggregation and activation during the loading process. Exemplary components (e.g., anti-aggregation agents) may include an anti-aggregation agent such as, Prostaglandin E1 or Prostacyclin and or EDTA/EGTA to prevent platelet aggregation and activation during the loading process. Additional non-limiting anti-aggregation agents may include, GR144053, FR171113, aspirin, MeSADP, PSB 0739, Cangrelor, Tirofiban (e.g., Aggrastat™), and MitoTEMPO, N-acetyyl-L-cysteine, cytcochalasin D, Staurosporine, Mepacrine, actezolamide, or dichloroacetate. These components may be used alone or in combination with one another.

Accordingly, in some embodiments, an agent suitable for treatment of cancer, such as doxorubicin, may be loaded together with, prior to, or following, a GPIIb/IIIa inhibitor. In some embodiments, the cancer is acute lymphoblastic leukemia. In some embodiments, the cancer is acute myeloid leukemia. In some embodiments, the cancer is breast cancer or metastasized breast cancer. In some embodiments, the cancer is gastric cancer. In some embodiments, the cancer is Hodgkin lymphoma. In some embodiments, the cancer is neuroblastoma. In some embodiments, the cancer is Non-Hodgkin lymphoma. In some embodiments, the cancer is ovarian cancer. In some embodiments, the cancer is small cell lung cancer. In some embodiments, the cancer is soft tissue and bone sarcomas. In some embodiments, the cancer is thyroid cancer. In some embodiments, the cancer is transitional cell bladder cancer. In some embodiments, the cancer is Wilms tumor.

Accordingly, in some embodiments, an agent suitable for treatment of cancer, such as olaparib (also known as AZD-2281, MK-7339, trade name Lynparza®), may be loaded together with, prior to, or following, a GPIIb/IIIa inhibitor.

In some embodiments, the cancer is ovarian cancer. In some embodiments, the cancer is breast cancer.

Accordingly, in some embodiments, an agent suitable for treatment of cancer, such as paclitaxel (Taxol®), may be loaded together with, prior to, or following, a GPIIb/IIIa inhibitor. In some embodiments, the cancer is Kaposi sarcoma. In some embodiments, the cancer is breast cancer. In some embodiments, the cancer is non-small cell lung cancer. In some embodiments, the cancer is ovarian cancer.

In some embodiments, an agent suitable for treatment of cancer, such as doxorubicin, may be loaded together with, prior to, or following, P2Y1 receptor activation inhibitor, a P2Y1 agonist, P2Y12 agonist, a P2Y13 agonist, a PAR 1 antagonist, a COX inhibitor, a P2Y12 inhibitor, a thiol supplement, a ROS antagonist, an actin polymerization inhibitor, protein kinase C inhibitor, phospholipase A2 inhibitor, Rho kinase inhibitor, a carbonic anhydrase inhibitor, or a PDK inhibitor.

In some embodiments, the one or more other components that are loaded in the platelets comprise Prostaglandin E1 (PGE1) or Prostacyclin.

In some embodiments, the one or more other components that are loaded in the platelets do not comprise Prostaglandin E1 or Prostacyclin.

In some embodiments, the one or more other components that are loaded in the platelets comprise EGTA.

In some embodiments, the one or more other components that are loaded in the platelets do not comprise EGTA.

In some embodiments, the one or more other components that are loaded in the platelets comprise EDTA.

In some embodiments, the one or more other components that are loaded in the platelets do not comprise EDTA.

The table below shows the effect of the addition of antiplatelet compounds on DOX-induced platelet aggregation:

TABLE A

| # | Reagent | Target | Source | Recommended concentration | Max Platelet Count (Normalized to Untreated) | | | |
|---|---|---|---|---|---|---|---|---|
| | | | | | 0.5 mg/mL DOX | 1 mg/mL DOX | 0.6 mM DOX | 1.2 mM DOX |
| 1 | GR144053 | GPIIb/IIIa inhibitor | PMID: 9700979 | IC50 = 37 nM | 83% | 42% | N/A | N/A |
| 2 | PGE1 | P2Y1 receptor activation Inhibitor | PMID: 22385219 PMID: 22268418 | 22 nM-1 μM | N/A | N/A | N/A | N/A |
| 3 | MeSADP | P2Y1, P2Y12, and P2Y13 Agonist | PMID: 9442039 | 10 μM | 33% | 10% | N/A | N/A |
| 4 | FR171113 | PAR1 antagonist | PMID: 10611442 | 0.3 μM | 51% | 16% | N/A | N/A |
| 5 | Aspirin (ASA) | COX inhibitor | PMID: 3370916 | 40-500 μM | 52% | 15% | N/A | N/A |
| 6 | Cangrelor | P2Y12 Inhibitor | PMID: 23236426 | 1 μM | 47% | 26% | N/A | N/A |
| 7 | PSB 0739 | P2Y12 Inhibitor | PMID: 27695417 | 500 nM | 26% | 18% | N/A | N/A |
| 8 | N-Acetylcysteine | Thiol Supplement | PMID: 19426282 page 1179 | 5 mM | N/A | N/A | 73% | N/A |
| 9 | MitoTEMPO | ROS Antagonist | PMID: 25988386 methods 4.3 | 10 μM | N/A | N/A | N/A | 37% |
| 10 | Tirofiban | GPIIb/IIIa inhibitor | PMID: 11406724 abstract | 5 μM | N/A | N/A | 73% | N/A |

The table below shows alternatively proposed antiplatelet compounds to combat DOX-induced platelet aggregation:

TABLE B

| # | Reagent | Target | Source | Recommended concentration |
|---|---|---|---|---|
| 1 | Cytochalasin D | actin polymerization | PMID: 10682859 page 357 | 10 μM |
| 2 | Staurosporine | protein kinase C inhibitor | PMID: 10051374 methods "PKC studies" PMID: 11895774 (function or reagent) | 25 nM to 10 μM |
| 3 | Mepacrine | Phospholipase A2 inhibitor | PMID: 3931692 | 2.5-20 μM |

In some embodiments, other components may include imaging agents. For example, an imaging agent can include, but is not limited to a radioactive metal ion, a paramagnetic metal ion, a gamma-emitting radioactive halogen, a positron-emitting radioactive non-metal, a hyperpolarized NMR-active nucleus, a reporter suitable for in vivo optical imaging, or a beta-emitter suitable for intravascular detection. For example, a radioactive metal ion can include, but is not limited to, positron emitters such as 54Cu, 48V, 52Fe, 55Co, 94Tc or 68Ga; or gamma-emitters such as 171Tc, 111In, 113In, or 67Ga. For example, a paramagnetic metal ion can include, but is not limited to Gd(III), a Mn(II), a Cu(II), a Cr(III), a Fe(III), a Co(II), a Er(II), a Ni(II), a Eu(III) or a Dy(III), an element comprising an Fe element, a neodymium iron oxide (NdFeO3) or a dysprosium iron oxide (DyFeO3). For example, a paramagnetic metal ion can be chelated to a polypeptide or a monocrystalline nanoparticle. For example, a gamma-emitting radioactive halogen can include, but is not limited to 123I, 131I or 77Br. For example, a positron-emitting radioactive non-metal can include, but is not limited to 11C, 13N, 15O, 17F, 18F, 75Br, 76Br or 124I. For example, a hyperpolarized NMR-active nucleus can include, but is not limited to 13C, 15N, 19F, 29Si and 31P. For example, a reporter suitable for in vivo optical imaging can include, but is not limited to any moiety capable of detection either directly or indirectly in an optical imaging procedure. For example, the reporter suitable for in vivo optical imaging can be a light scatterer (e.g., a colored or uncolored particle), a light absorber or a light emitter. For example, the reporter can be any reporter that interacts with light in the electromagnetic spectrum with wavelengths from the ultraviolet to the near infrared. For example, organic chromophoric and fluorophoric reporters include groups having an extensive delocalized electron system, e.g. cyanines, merocyanines, indocyanines, phthalocyanines, naphthalocyanines, triphenylmethines, porphyrins, pyrylium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, b/s(dithiolene) complexes, bιs(benzene-dithiolate) complexes, iodoaniline dyes, b/stS.O-dithiolene) complexes. For example, the reporter can be, but is not limited to a fluorescent, a bioluminescent, or chemiluminescent polypeptide. For example, a fluorescent or chemiluminescent polypeptide is a green florescent protein (GFP), a modified GFP to have different absorption/emission properties, a luciferase, an aequorin, an obelin, a mnemiopsin, a berovin, or a phenanthridinium ester. For example, a reporter can be, but is not limited to rare earth metals (e.g., europium, samarium, terbium, or dysprosium), or fluorescent nanocrystals (e.g., quantum dots). For example, a reporter may be a chromophore that can include, but is not limited to fluorescein, sulforhodamine 101 (Texas Red), rhodamine B, rhodamine 6G, rhodamine 19, indocyanine green, Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750. For example, a beta-emitter can include, but is not limited to radio metals 67Cu, 89Sr, 90Y, 153 Sm, 185Re, 188Re or 192Ir, and non-metals 32P, 33P, 38S, 38Cl, 39Cl, 82Br and 83Br. In some embodiments, a drug loaded into platelets can be associated with gold or other equivalent metal particles (such as nanoparticles). For example, a metal particle system can include, but is not limited to gold nanoparticles (e.g., Nanogold™).

In some embodiments, the one or more imaging agents loaded concurrently with a drug is imaged using an imaging unit. The imaging unit can be configured to image the drug loaded platelets in vivo based on an expected property (e.g., optical property from the imaging agent) to be characterized. For example, imaging techniques (in vivo imaging using an imaging unit) that can be used, but are not limited to are: computer assisted tomography (CAT), magnetic resonance spectroscopy (MRS), magnetic resonance imaging (MM), positron emission tomography (PET), single-photon emission computed tomography (SPECT), or bioluminescence imaging (BLI). Chen Z. et. al., (2014) have described various imaging techniques and which is incorporated by reference herein in its entirety.

In some embodiments, the drug-loaded platelets are prepared by incubating the platelets with the drug in the liquid medium for different durations. The step of incubating the platelets to load one or more cargo, such as a drug(s), includes incubating the platelets for a time suitable for loading, as long as the time, taken in conjunction with the temperature, is sufficient for the drug to come into contact with the platelets and, preferably, be incorporated, at least to some extent, into the platelets. For example, in some embodiments, the drug-loaded platelets are prepared by incubating the platelets with the drug in the liquid medium for at least about 5 minutes (mins) (e.g., at least about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, about 42 hrs, about 48 hrs, or at least about 48 hrs. In some embodiments, the drug-loaded platelets are prepared by incubating the platelets with the drug in the liquid medium for no more than about 48 hrs (e.g., no more than about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, or no more than about 42 hrs). In some embodiments, the drug-loaded platelets are prepared by incubating the platelets with the drug in the liquid medium from about 10 mins to about 48 hours (e.g., from about 20 mins to about 36 hrs, from about 30 mins to about 24 hrs, from about 1 hr to about 20 hrs, from about 2 hrs to about 16 hours, from about 10 mins to about 24 hours, from about 20 mins to about 12 hours, from about 30 mins to about 10 hrs, or from about 1 hr to about 6 hrs. In one embodiment, treating platelets, platelet derivatives, or thrombosomes with a drug, a liquid medium, a buffer comprising a salt, a base, a loading agent, and optionally at least one organic solvent, and/or with any loading protocol described herein to form the drug-loaded platelets comprises contacting the platelets, platelet derivatives, or thrombosomes with a drug, a liquid medium, a buffer comprising a salt, a base, a loading agent, and optionally at least one organic solvent and/or with any loading protocol described herein for a period of time, such as a period of 5 minutes to 48 hours, such as 2 hours.

In some embodiments, the drug-loaded platelets are prepared by incubating the platelets with the drug in the liquid medium at different temperatures. The step of incubating the platelets to load one or more cargo, such as a drug(s), includes incubating the platelets with the drug in the liquid medium at a temperature that, when selected in conjunction with the amount of time allotted for loading, is suitable for loading. In general, the platelets with the drug in the liquid medium are incubated at a suitable temperature (e.g., a temperature above freezing) for at least a sufficient time for the drug to come into contact with the platelets. In embodiments, incubation is conducted at 37° C. In certain embodiments, incubation is performed at 4° C. to 45° C., such as 15° C. to 42° C. For example, in embodiments, incubation is performed at 35° C. to 40° C. (e.g., 37° C.) for 110 to 130 (e.g., 120) minutes and for as long as 24-48 hours.

In some embodiments of a method of preparing drug-loaded platelets disclosed herein, the method further comprises acidifying the platelets, or pooled platelets, to a pH of about 6.0 to about 7.4, prior to a treating step disclosed herein. In some embodiments, the method comprises acidifying the platelets to a pH of about 6.5 to about 6.9. In some embodiments, the method comprises acidifying the platelets to a pH of about 6.6 to about 6.8. In some embodiments, the acidifying comprises adding to the pooled platelets a solution comprising Acid Citrate Dextrose.

In some embodiments, the platelets are isolated prior to a treating step. In some embodiments, the method further comprises isolating platelets by using centrifugation. In some embodiments, the centrifugation occurs at a relative centrifugal force (RCF) of about 800 g to about 2000 g. In some embodiments, the centrifugation occurs at relative centrifugal force (RCF) of about 1300 g to about 1800 g. In some embodiments, the centrifugation occurs at relative centrifugal force (RCF) of about 1500 g. In some embodiments, the centrifugation occurs for about 1 minute to about 60 minutes. In some embodiments, the centrifugation occurs for about 10 minutes to about 30 minutes. In some embodiments, the centrifugation occurs for about 30 minutes.

In some embodiments, the platelets are at a concentration from about 2,000 platelets/µl to about 500,000,000 platelets/µl. In some embodiments, the platelets are at a concentration from about 50,000 platelets/µl to about 4,000,000 platelets/µl. In some embodiments, the platelets are at a concentration from about 100,000 platelets/µl to about 300,000,000 platelets/µl. In some embodiments, the platelets are at a concentration from about 1,000,000 to about 2,000,000. In some embodiments, the platelets are at a concentration of about 200,000,000 platelets/µl.

In some embodiments, the buffer is a loading buffer comprising the components as listed in Table 1 herein. In some embodiments, the loading buffer comprises one or more salts, such as phosphate salts, sodium salts, potassium salts, calcium salts, magnesium salts, and any other salt that can be found in blood or blood products. Exemplary salts include sodium chloride (NaCl), potassium chloride (KCl), and combinations thereof. In some embodiments, the loading buffer includes from about 0.5 mM to about 100 mM of the one or more salts. In some embodiments, the loading buffer includes from about 1 mM to about 100 mM (e.g., about 2 mM to about 90 mM, about 2 mM to about 6 mM, about 50 mM to about 100 mM, about 60 mM to about 90 mM, about 70 to about 85 mM) about of the one or more salts. In some embodiments, the loading buffer includes about 5 mM, about 75 mM, or about 80 mM of the one or more salts.

In some embodiments, the loading buffer includes one or more buffers, e.g., N-2-hydroxyethylpiperazine-N'-2-ethanesulfonic acid (HEPES), or sodium-bicarbonate (NaHCO$_3$). In some embodiments, the loading buffer includes from about 5 to about 100 mM of the one or more buffers. In some embodiments, the loading buffer includes from about 5 to about 50 mM (e.g., from about 5 mM to about 40 mM, from about 8 mM to about 30 mM, about 10 mM to about 25 mM) about of the one or more buffers. In some embodiments, the loading buffer includes about 10 mM, about 20 mM, about 25 mM, or about 30 mM of the one or more buffers.

In some embodiments, the loading buffer includes one or more saccharides, such as monosaccharides and disaccharides, including sucrose, maltose, trehalose, glucose, mannose, dextrose, and xylose. In some embodiments, the loading buffer includes from about 10 mM to about 1,000 mM of the one or more saccharides. In some embodiments, the loading buffer includes from about 50 to about 500 mM of the one or more saccharides. In embodiments, one or more saccharides is present in an amount of from 10 mM 10 to 500 mM. In some embodiments, one or more saccharides is present in an amount of from 50 mM to 200 mM. In embodiments, one or more saccharides is present in an amount from 100 mM to 150 mM.

In some embodiments, the loading buffer includes adding an organic solvent, such as ethanol, to the loading solution. In such a loading buffer, the solvent can range from about 0.1% (v/v) to about 5.0% (v/v), such as from about 0.3% (v/v) to about 3.0% (v/v), or from about 0.5% (v/v) to about 2% (v/v).

In some embodiments, the drug comprises doxorubicin ("DOX"). DOX interacts with DNA by intercalation and inhibits macromolecular biosynthesis (Tacar, O. et. al., Doxorubicin: an update on anticancer molecular action, toxicity and novel drug delivery systems, *The Journal of Pharmacy and Pharmacology*, 65 (2): 157-70. doi:10.1111/j.2042-7158.2012.01567.x. PMID 23278683 (2013), which is incorporated herein by reference).

In some embodiment, the drug comprises paclitaxel. In some embodiment, the drug comprises paclitaxel that is not in the presence of Cremophor EL. In some embodiments, the drug comprises paclitaxel that is not in the presence (e.g., an excipient) of a polyexthoxylated castor oil. For example, paclitaxel that is not in the presence of an excipient comprising a polyethylene glycol ether.

In some embodiments, the drug comprises a poly ADP ribose polymerase (PARP) inhibitor (PARPi). PARPis prevent the normal repair of DNA breaks which in turn leads to cell death. In some embodiments, the PARPi is olaparib.

In some embodiments, the method further comprises incubating the drug in the presence of the loading buffer prior to the treatment step. In some embodiments, the method further comprises incubating the loading buffer and a solution comprising the drug and water at about 37° C. using different incubation periods. In some embodiments, the solution includes a concentration of about 1 nM to about 1000 mM of the drug. In some embodiments, the solution includes a concentration of about 10 nM to about 10 mM of the drug. In some embodiments, the solution includes a concentration of about 100 nM to 1 mM of the drug. In some embodiments, the solution includes a concentration of from about 10 mg/ml of water to about 100 mg/ml. In some embodiments, the solution includes a concentration of from about 20 mg/ml of water to about 80 mg/ml. In some embodiments, the solution includes a concentration of from about 40 mg/ml of water to about 60 mg/ml. In some embodiments, the incubation of the drug in the presence of the loading buffer is performed from about 1 minute to about 2 hours. In some embodiments, the incubation is performed at an incubation period of from about 5 minutes to about 1 hour. In some embodiments, the incubation is performed at an incubation period of from about 10 minutes to about 30 minutes. In some embodiments, the incubation is performed at an incubation period of about 20 minutes.

In some embodiments, the method further comprises mixing the platelets and the drug in the presence of the loading buffer at 37° C., using a platelet to drug volume ratio of 1:2. In some embodiments, the method further comprises incubating the platelets and the drug in the presence of the loading buffer at 37° C. using a platelet to drug volume ratio of 1:2, using different incubation periods. In some embodiments, the incubation is performed at an incubation period of from about 5 minutes to about 12 hours. In some embodiments, the incubation is performed at an incubation period of from about 10 minutes to about 6 hours. In some embodiments, the incubation is performed at an incubation period of from about 15 minutes to about 3 hours. In some embodiments, the incubation is performed at an incubation period of about 2 hours.

In some embodiments, the concentration of drug in the drug-loaded platelets is from about 1 nM to about 1000 mM. In some embodiments, the concentration of drug in the drug-loaded platelets is from about 10 nM to about 10 mM. In some embodiments, the concentration of drug in the drug-loaded platelets is from 100 nM to 1 mM.

In some embodiments, the method further comprises drying the drug-loaded platelets. In some embodiments, the drying step comprises freeze-drying the drug-loaded platelets. In some embodiments, the method further comprises rehydrating the drug-loaded platelets obtained from the drying step.

In some embodiments, drug-loaded platelets are prepared by using any one of the methods provided herein.

In some embodiments, rehydrated drug-loaded platelets are prepared by any one method comprising rehydrating the drug-loaded platelets provided herein.

The drug-loaded platelets may be then used, for example, for therapeutic applications as disclosed herein. As another example, the drug-loaded platelets may be employed in functional assays. In some embodiments, the drug-loaded platelets are cold stored, cryopreserved, or lyophilized (to produce thrombosomes) prior to use in therapy or in functional assays.

Any known technique for drying platelets can be used in accordance with the present disclosure, as long as the technique can achieve a final residual moisture content of less than 5%. Preferably, the technique achieves a final residual moisture content of less than 2%, such as 1%, 0.5%, or 0.1%. Non-limiting examples of suitable techniques are freeze-drying (lyophilization) and spray-drying. A suitable lyophilization method is presented in Table A. Additional exemplary lyophilization methods can be found in U.S. Pat. Nos. 7,811,558, 8,486,617, and 8,097,403. An exemplary spray-drying method includes: combining nitrogen, as a drying gas, with a loading buffer according to the present disclosure, then introducing the mixture into GEA Mobile Minor spray dryer from GEA Processing Engineering, Inc. (Columbia Md., USA), which has a Two-Fluid Nozzle configuration, spray drying the mixture at an inlet temperature in the range of 150° C. to 190° C., an outlet temperature in the range of 65° C. to 100° C., an atomic rate in the range of 0.5 to 2.0 bars, an atomic rate in the range of 5 to 13 kg/hr, a nitrogen use in the range of 60 to 100 kg/hr, and a run time of 10 to 35 minutes. The final step in spray drying is preferentially collecting the dried mixture. The dried composition in some embodiments is stable for at least six months at temperatures that range from −20° C. or lower to 90° C. or higher.

TABLE B

Exemplary Lyophilization Protocol

| | Step | Temp. Set | Type | Duration | Pressure Set |
|---|---|---|---|---|---|
| Freezing Step | F1 | −50° C. | Ramp | Var | N/A |
| | F2 | −50° C. | Hold | 3 Hrs | N/A |
| Vacuum Pulldown | F3 | −50° | Hold | Var | N/A |
| Primary Dry | P1 | −40° | Hold | 1.5 Hrs | 0 mT |
| | P2 | −35° | Ramp | 2 Hrs | 0 mT |
| | P3 | −25° | Ramp | 2 Hrs | 0 mT |
| | P4 | −17° C. | Ramp | 2 Hrs | 0 mT |
| | P5 | 0° C. | Ramp | 1.5 Hrs | 0 mT |
| | P6 | 27° C. | Ramp | 1.5 Hrs | 0 mT |
| | P7 | 27° C. | Hold | 16 Hrs | 0 mT |
| Secondary Dry | S1 | 27° C. | Hold | >8 Hrs | 0 mT |

In some embodiments, the step of drying the drug-loaded platelets that are obtained as disclosed herein, such as the step of freeze-drying the drug-loaded platelets that are obtained as disclosed herein, comprises incubating the platelets with a lyophilizing agent (e.g., a non-reducing disaccharide. Accordingly, in some embodiments, the methods for preparing drug-loaded platelets further comprise incubating the drug-loaded platelets with a lyophilizing agent.

In some embodiments the lyophilizing agent is a saccharide. In some embodiments the saccharide is a disaccharide, such as a non-reducing disaccharide).

In some embodiments, the platelets are incubated with a lyophilizing agent for a sufficient amount of time and at a suitable temperature to load the platelets with the lyophilizing agent. Non-limiting examples of suitable lyophilizing agents are saccharides, such as monosaccharides and disaccharides, including sucrose, maltose, trehalose, glucose (e.g., dextrose), mannose, and xylose. In some embodiments, non-limiting examples of a lyophilizing agent include serum albumin, dextran, polyvinyl pyrrolidone (PVP), starch, and hydroxyethyl starch (HES). In some embodiments, exemplary lyophilizing agents can include a high molecular weight polymer, into the loading composition. By "high molecular weight" it is meant a polymer having an average molecular weight of about or above 70 kDa. Non-limiting examples are polymers of sucrose and epichlorohydrin. In some embodiments, the lyophilizing agent is polysucrose. Although any amount of high molecular weight polymer can be used as a lyophilizing agent, it is preferred that an amount be used that achieves a final concentration of about 3% to 10% (w/v), such as 3% to 7%, for example 6%.

In some embodiments, the process for preparing a composition includes adding an organic solvent, such as ethanol, to the loading solution. In such a loading solution, the solvent can range from 0.1% to 5.0% (v/v).

Within the process provided herein for making the compositions provided herein, addition of the lyophilizing agent can be the last step prior to drying. However, in some embodiments, the lyophilizing agent is added at the same time or before the drug, the cryoprotectant, or other components of the loading composition. In some embodiments, the lyophilizing agent is added to the loading solution, thoroughly mixed to form a drying solution, dispensed into a drying vessel (e.g., a glass or plastic serum vial, a lyophilization bag), and subjected to conditions that allow for drying of the solution to form a dried composition.

An exemplary saccharide for use in the compositions disclosed herein is trehalose. Regardless of the identity of the saccharide, it can be present in the composition in any suitable amount. For example, it can be present in an amount of 1 mM to 1 M. In some embodiments, it is present in an amount of from 10 mM 10 to 500 mM. In some embodiments, it is present in an amount of from 20 mM to 200 mM. In some embodiments, it is present in an amount from 40 mM to 100 mM. In various embodiments, the saccharide is present in different specific concentrations within the ranges recited above, and one of skill in the art can immediately understand the various concentrations without the need to specifically recite each herein. Where more than one saccharide is present in the composition, each saccharide can be present in an amount according to the ranges and particular concentrations recited above.

The step of incubating the platelets to load them with a cryoprotectant or as a lyophilizing agent includes incubating the platelets for a time suitable for loading, as long as the time, taken in conjunction with the temperature, is sufficient for the cryoprotectant or lyophilizing agent to come into contact with the platelets and, preferably, be incorporated, at least to some extent, into the platelets. In some embodiments, incubation is carried out for about 1 minute to about 180 minutes or longer.

The step of incubating the platelets to load them with a cryoprotectant or lyophilizing agent includes incubating the platelets and the cryoprotectant at a temperature that, when selected in conjunction with the amount of time allotted for loading, is suitable for loading. In general, the composition is incubated at a temperature above freezing for at least a sufficient time for the cryoprotectant or lyophilizing agent to come into contact with the platelets. In embodiments, incubation is conducted at 37° C. In certain embodiments, incubation is performed at 20° C. to 42° C. For example, in embodiments, incubation is performed at 35° C. to 40° C. (e.g., 37° C.) for 110 to 130 (e.g., 120) minutes.

In various embodiments, the bag is a gas-permeable bag configured to allow gases to pass through at least a portion or all portions of the bag during the processing. The gas-permeable bag can allow for the exchange of gas within the interior of the bag with atmospheric gas present in the surrounding environment. The gas-permeable bag can be permeable to gases, such as oxygen, nitrogen, water, air, hydrogen, and carbon dioxide, allowing gas exchange to occur in the compositions provided herein. In some embodiments, the gas-permeable bag allows for the removal of some of the carbon dioxide present within an interior of the bag by allowing the carbon dioxide to permeate through its wall. In some embodiments, the release of carbon dioxide from the bag can be advantageous to maintaining a desired pH level of the composition contained within the bag.

In some embodiments, the container of the process herein is a gas-permeable container that is closed or sealed. In some embodiments, the container is a container that is closed or sealed and a portion of which is gas-permeable. In some embodiments, the surface area of a gas-permeable portion of a closed or sealed container (e.g., bag) relative to the volume of the product being contained in the container (hereinafter referred to as the "SA/V ratio") can be adjusted to improve pH maintenance of the compositions provided herein. For example, in some embodiments, the SA/V ratio of the container can be at least about 2.0 mL/cm² (e.g., at least about 2.1 mL/cm², at least about 2.2 mL/cm², at least about 2.3 mL/cm², at least about 2.4 mL/cm², at least about 2.5 mL/cm², at least about 2.6 mL/cm², at least about 2.7 mL/cm², at least about 2.8 mL/cm², at least about 2.9 mL/cm², at least about 3.0 mL/cm², at least about 3.1 mL/cm², at least about 3.2 mL/cm², at least about 3.3 mL/cm², at least about 3.4 mL/cm², at least about 3.5 mL/cm², at least about 3.6 mL/cm², at least about 3.7 mL/cm², at least about 3.8 mL/cm², at least about 3.9 mL/cm², at least about 4.0 mL/cm², at least about 4.1 mL/cm², at least about 4.2 mL/cm², at least about 4.3 mL/cm², at least about 4.4 mL/cm², at least about 4.5 mL/cm², at least about 4.6 mL/cm², at least about 4.7 mL/cm², at least about 4.8 mL/cm², at least about 4.9 mL/cm², or at least about 5.0 mL/cm². In some embodiments, the SA/V ratio of the container can be at most about 10.0 mL/cm² (e.g., at most about 9.9 mL/cm², at most about 9.8 mL/cm², at most about 9.7 mL/cm², at most about 9.6 mL/cm², at most about 9.5 mL/cm², at most about 9.4 mL/cm², at most about 9.3 mL/cm², at most about 9.2 mL/cm², at most about 9.1 mL/cm², at most about 9.0 mL/cm², at most about 8.9 mL/cm², at most about 8.8 mL/cm², at most about 8.7 mL/cm², at most about 8.6, mL/cm² at most about 8.5 mL/cm², at most about 8.4 mL/cm², at most about 8.3 mL/cm², at most about 8.2 mL/cm², at most about 8.1 mL/cm², at most about 8.0 mL/cm², at most about 7.9 mL/cm², at most about 7.8 mL/cm², at most about 7.7 mL/cm², at most about 7.6 mL/cm², at most about 7.5 mL/cm², at most about 7.4 mL/cm², at most about 7.3 mL/cm², at most about 7.2 mL/cm², at most about 7.1 mL/cm², at most about 6.9 mL/cm², at most about 6.8 mL/cm², at most about 6.7 mL/cm², at most about 6.6 mL/cm², at most about 6.5 mL/cm², at most about 6.4 mL/cm², at most about 6.3 mL/cm², at most about 6.2 mL/cm², at most about 6.1 mL/cm², at most about 6.0 mL/cm², at most about 5.9 mL/cm², at most about 5.8 mL/cm², at most about 5.7 mL/cm², at most about 5.6 mL/cm², at most about 5.5 mL/cm², at most about 5.4 mL/cm², at most about 5.3 mL/cm², at most about 5.2 mL/cm², at most about 5.1 mL/cm², at most about 5.0 mL/cm², at most about 4.9 mL/cm², at most about 4.8 mL/cm², at most about 4.7 mL/cm², at most about 4.6 mL/cm², at most about 4.5 mL/cm², at most about 4.4 mL/cm², at most about 4.3 mL/cm², at most about 4.2 mL/cm², at most about 4.1 mL/cm², or at most about 4.0 mL/cm². In some embodiments, the SA/V ratio of the container can range from about 2.0 to about 10.0 mL/cm² (e.g., from about 2.1 mL/cm² to about 9.9 mL/cm², from about 2.2 mL/cm² to about 9.8 mL/cm², from about 2.3 mL/cm² to about 9.7 mL/cm², from about 2.4 mL/cm² to about 9.6 mL/cm², from about 2.5 mL/cm² to about 9.5 mL/cm², from about 2.6 mL/cm² to about 9.4 mL/cm², from about 2.7 mL/cm² to about 9.3 mL/cm², from about 2.8 mL/cm² to about 9.2 mL/cm², from about 2.9 mL/cm² to about 9.1 mL/cm², from about 3.0 mL/cm² to about 9.0 mL/cm², from about 3.1 mL/cm² to about 8.9 mL/cm², from about 3.2 mL/cm² to about 8.8 mL/cm², from about 3.3 mL/cm² to about 8.7 mL/cm², from about 3.4 mL/cm² to about 8.6 mL/cm², from about 3.5 mL/cm² to about 8.5 mL/cm², from about 3.6 mL/cm² to about 8.4 mL/cm², from about 3.7 mL/cm² to about 8.3 mL/cm², from about 3.8 mL/cm² to about 8.2 mL/cm², from about 3.9 mL/cm² to about 8.1 mL/cm², from about 4.0 mL/cm² to about 8.0 mL/cm², from about 4.1 mL/cm² to about 7.9 mL/cm², from about 4.2 mL/cm² to about 7.8 mL/cm², from about 4.3 mL/cm² to about 7.7 mL/cm², from about 4.4 mL/cm² to about 7.6 mL/cm², from about 4.5 mL/cm² to about 7.5 mL/cm², from about 4.6 mL/cm² to about 7.4 mL/cm², from about 4.7 mL/cm² to about 7.3 mL/cm², from about 4.8 mL/cm² to about 7.2 mL/cm², from about 4.9 mL/cm² to about 7.1 mL/cm², from about 5.0 mL/cm² to about 6.9 mL/cm², from about 5.1 mL/cm² to about 6.8 mL/cm², from about 5.2 mL/cm² to about 6.7 mL/cm², from about 5.3 mL/cm² to about 6.6 mL/cm², from about 5.4 mL/cm$^2$ to about 6.5 mL/cm$^2$, from about 5.5 mL/cm$^2$ to about 6.4 mL/cm$^2$, from about 5.6 mL/cm$^2$ to about 6.3 mL/cm$^2$, from about 5.7 mL/cm$^2$ to about 6.2 mL/cm$^2$, or from about 5.8 mL/cm$^2$ to about 6.1 mL/cm$^2$.

Gas-permeable closed containers (e.g., bags) or portions thereof can be made of one or more various gas-permeable materials. In some embodiments, the gas-permeable bag can be made of one or more polymers including fluoropolymers (such as polytetrafluoroethylene (PTFE) and perfluoroalkoxy (PFA) polymers), polyolefins (such as low-density polyethylene (LDPE), high-density polyethylene (HDPE)), fluorinated ethylene propylene (FEP), polystyrene, polyvinylchloride (PVC), silicone, and any combinations thereof.

In some embodiments the lyophilizing agent as disclosed herein may be a high molecular weight polymer. By "high molecular weight" it is meant a polymer having an average molecular weight of about or above 70 kDa and up to 1,000,000 kDa. Non-limiting examples are polymers of sucrose and epichlorohydrin (poly sucrose). Although any amount of high molecular weight polymer can be used, it is preferred that an amount be used that achieves a final concentration of about 3% to 10% (w/v), such as 3% to 7%, for example 6%. Other non-limiting examples of lyoprotectants are serum albumin, dextran, polyvinyl pyrrolidone (PVP), starch, and hydroxyethyl starch (HES).

In some embodiments, the loading buffer comprises an organic solvent, such as an alcohol (e.g., ethanol). In such a loading buffer, the amount of solvent can range from 0.1% to 5.0% (v/v).

In some embodiments the drug-loaded platelets prepared as disclosed herein have a storage stability that is at least about equal to that of the platelets prior to the loading of the drug.

The loading buffer may be any buffer that is non-toxic to the platelets and provides adequate buffering capacity to the solution at the temperatures at which the solution will be exposed during the process provided herein. Thus, the buffer may comprise any of the known biologically compatible buffers available commercially, such as phosphate buffers, such as phosphate buffered saline (PBS), bicarbonate/carbonic acid, such as sodium-bicarbonate buffer, N-2-hydroxyethylpiperazine-N'-2-ethanesulfonic acid (HEPES), and tris-based buffers, such as tris-buffered saline (TBS). Likewise, it may comprise one or more of the following buffers: propane-1,2,3-tricarboxylic (tricarballylic); benzenepentacarboxylic; maleic; 2,2-dimethyl succinic; EDTA; 3,3-dimethylglutaric; bis(2-hydroxyethyl)imino-tris(hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3 tetramethylene-glutaric acid); piperazine-1,4-bis-(2-ethanesulfonic acid) (PIPES); N-(2-acetamido)-2-amnoethanesulfonic acid (ACES); 1,1-cyclohexanediacetic; 3,6-endomethylene-1,2,3,6-tetrahydrophthalic acid (EMTA; ENDCA); imidazole; 2-(aminoethyl)trimethylammonium chloride (CHOLAMINE); N,N-bis(2-hydroxyethyl)-2-aminoethanesulfonic acid (BES); 2-methylpropane-1,2,3-triscarboxylic (beta-methyltricarballylic); 2-(N-morpholino)propanesulfonic acid (MOPS); phosphoric; and N-tris(hydroxymethyl)methyl-2-amminoethane sulfonic acid (TES).

Flow cytometry is used to obtain a relative quantification of loading efficiency by measuring the mean fluorescence intensity of the drug in the drug-loaded platelets. Platelets are evaluated for functionality by ADP and/or TRAP stimulation post-loading.

In some embodiments the drug-loaded platelets are lyophilized. In some embodiments the drug-loaded platelets are cryopreserved.

In some embodiments the drug-loaded platelets retain the loaded drug upon rehydration and release the drug upon stimulation by endogenous platelet activators.

In some embodiments the dried platelets (such as freeze-dried platelets) retain the loaded drug upon rehydration and release the drug upon stimulation by endogenous platelet activators. In some embodiments at least about 10%, such as at least about 20%, such as at least about 30% of the drug is retained. In some embodiments from about 10% to about 20%, such as from about 20% to about 30% of the drug is retained.

An example of a drug that may be loaded in a platelet is doxorubicin. Another example is of a drug that may be loaded in a platelet is olaparib. Another example of a drug that may be loaded in a platelet is paclitaxel.

Various agents and/or procedures may be used to load the platelets with a drug. In some embodiments, the platelets are loaded with a liposomal formulation of the drug. In some embodiments, the drug is not comprised in a liposomal formulation. In some embodiments, the platelets are loaded with a drug previously incubated with a cell penetrating peptide. In some embodiments, the platelets are loaded with a drug previously incubated with a cationic lipid such as lipofectamine. In some embodiments, the platelets are loaded with the drug in the presence of a detergent. For example, the detergent may be saponin.

In some embodiments, the platelets are loaded by a process comprising endocytosis.

In some embodiments, the platelets are loaded by a process comprising electroporation.

In some embodiments, the platelets are loaded by a process comprising transduction.

In some embodiments, the platelets are loaded by a process comprising sonoporation.

In some embodiments, the platelets are loaded by a process comprising osmotic hypertonic/hypotonic loading/hypotonic shock. Hypotonic shock uses a solution with lower osmotic pressure to induce cell swelling leading to membrane permeability. Hypertonic shock may increase platelet loading of cryoprotectants or lyoprotectants (e.g., trehalose) (Zhou X., et. al., Loading Trehalose into Red Blood Cells by Improved Hypotonic Method, *Cell Preservation Technology*, 6(2), https://doi.org/10.1089/cpt.2008.0001 (2008), which is herein incorporated by reference). Additionally and alternatively, hypotonic shock may allow the uptake and internalization of large and/or charged molecules through passive means, such as, endocytosis, micropinocytosis, and/or diffusion.

In some embodiments, the solutes in the hypertonic solution can be, in a non-limiting way, salts, low-molecular weight sugars (e.g., monosaccharides, disaccharides), or low molecular weight inert hydrophilic polymers.

In some embodiments, the platelets are loaded by a process comprising the use of Transfection Reagents (also described in WO2014118817A2, incorporated by reference herein in its entirety).

Exemplary protocols that employ the foregoing agents or procedures are described below:

A liposome is a vesicle made of phospholipid bilayer. This vesicle can be designed to encapsulate drug of interest, which is delivered inside a cell following the fusion of vesicle and cell membrane.

Liposome encapsulated Doxorubicin (chemotherapy drug) is prepared through rehydration of lyophilized lipids (Sigma-Aldrich, L4395-1VL) with drug in PBS followed by 30 seconds of agitation via vortex, then 30 minutes of incubation at 37° C. The liposomes are then incubated with platelets at 37° C. for 30 minutes. Cells are washed once via centrifugation to remove incorporated liposome encapsulated doxorubicin or free doxorubicin. Drug loaded platelets can be lyophilized in appropriate buffer to create Thrombosomes. Flow cytometry and fluorescence microscopy may be performed to assess drug loading and intracellular localization. A fluorescence microplate reader can be used to obtain quantification of drug load. Light transmission aggregometry will be used to evaluate platelet function post drug load.

Endocytosis is a process through which a cell takes in material from its surroundings. The cell invaginates its plasma membrane to wrap around fluid or particles in its immediate environment. The internalized vesicle buds off from the plasma membrane and remains inside the cell.

Co-incubation of platelets with drug of interest occurs at 37° C. for 1-4 hours during which drug is loaded into platelets via endocytosis. Loaded platelets may then be lyophilized to make Thrombosomes. Loaded drug is detected via flow cytometry or fluorescence microscopy, provided drug is fluorescently tagged or is itself fluorescent. Loaded drug can be detected by HPLC or a microplate reader (e.g., a Tecan plate reader). Endocytic inhibitors such as amiloride (1 mM), phenylarsine oxide (10 μM), cytochalasin D (4 μM), or dynasore (25 μM) can be used to confirm that platelet loading is achieved by endocytosis.

Pep-1 is a 21 amino acid cell penetrating peptide with a C-terminal cysteamine group that shuttles cargo such as proteins or peptides into target cells. Pep-1 consists of a hydrophobic domain linked to a hydrophilic domain. The hydrophobic, tryptophan-rich domain can associate with a target cell membrane and the hydrophobic domains of the cargo protein (See e.g., Heitz, F., et. al., Twenty years of cell-penetrating peptides: from molecular mechanisms to therapeutics, British Journal of Pharmacology, 157, 195-206, (2009), which is incorporated herein by reference in its entirety).

The Pep-1 and the cargo protein are complexed by co-incubation at 37° C. for 30 minutes. The Pep-1:protein complex is incubated with platelets at 37° C. for at minimum 1 hour to allow Pep-1 mediated loading of protein cargo into the platelet. Platelets are washed by centrifugation to remove cell-free Pep-1:protein complex. Loaded platelets may then be lyophilized to make Thrombosomes. Platelets that have accumulated Pep-1 can be detected via flow cytometry or fluorescence microscopy if a fluorescent tag is attached to the C-terminus cysteamine of Pep-1. If the cargo protein is fluorescently labeled, then platelets containing this cargo may also be detected using flow cytometry or fluorescence microscopy.

The HIV Tat protein is another example of a cell penetrating peptide. The Tat protein includes between 86 and 101 amino acids depending on the subtype. Tat is a regulatory protein that enhances the viral transcription efficiency. Tat also contains a protein transduction domain which functions as a cell-penetrating domain allowing Tat to cross cellular membranes.

Lipofectamine is a cationic lipid; the Lipofectamine positively charged head group interacts with the negatively charged phosphate backbone of nucleic acids to facilitate transfection. Cellular internalization of the nucleic acid is achieved by incubating cells with the complex of Lipofectamine and nucleic acid.

Prepare the Lipofectamine and nucleic acid complex in aqueous buffer at room temperature. Incubate the complex of Lipofectamine and nucleic acid with platelets for 2-3 hours. Transfected platelets may be lyophilized to create Thrombosomes. Fluorescently labeled nucleic acid can be detected via flow cytometry and visualized using fluorescence microscopy. This method of loading is applicable to both RNA and DNA.

An electroporation machine generates electrical pulses which facilitate formation of transient openings in plasma membranes. The increased plasma membrane permeability allows entry of large and/or charged cargo that would otherwise not enter the cell due to membrane barrier.

Perform electroporation of platelets in the presence of desired cargo. Cargos of interest can be detected by flow cytometry and fluorescence microscopy if they are fluorescently tagged.

The influx cell loading strategy harnesses osmosis to load cells with water soluble, polar compounds. Cells are initially placed in a hypertonic solution containing drug of interest. In this hypertonic solution, water will move out of the cell into solution while drug will move into the cell via pinocytosis. Following that, cells are placed in a hypotonic solution in which water will enter the cell, lysing the pinocytic vesicles and thereby releasing drug into the cytosol.

Incubate platelets in hypertonic loading medium containing drug compound at 37° C. for at least 1 hour. Isolate loaded platelets from solution via centrifugation, resuspend platelets in hypotonic lysis medium, and incubate at 37° C. Pinocytic vesicles will burst and release drug into the cytosol. Fluorescently labeled drug can be visualized using fluorescence microscopy to confirm internalization. Flow cytometry may be performed to quantify drug load per cell for fluorescent drug.

Viral vectors are commonly used for transduction of cells. The host cell is driven by the viral vector to express the protein of interest at high load.

Use lentiviral vector to transfect 293T cells to generate pseudovirus, which is collected from the supernatant of this cell culture. The pseudovirus is then used to transduce megakaryocytes. Inside the transduced megakaryocyte, viral core plasmid containing cytomegalovirus promoter drives overexpression of the protein of interest, which gets packaged into platelets that bud off from transduced megakaryocytes.

Human platelets express FcγRIIA receptor which binds to the Fc region of IgG and facilitates internalization of IgG immune complexes. This method of loading platelets provides a route for delivery of therapeutic antibodies.

Incubate fluorescently labeled IgG at 62° C. for 20 minutes to prepare IgG immune complexes. Incubate IgG immune complexes with platelets for 1 hour at 4° C. to allow cells to bind immune complexes. Next, incubate immune complex-bound platelets at 37° C. to allow internalization of immune complexes. Flow cytometry can detect internalized fluorophore labeled IgG immune complexes. An anti-IgG-PE antibody specific for immune complexes can be used to identify surface bound, but not internalized, IgG-FITC immune complex.

Examples of drugs and of loading agents are as follows:

| Endocytosis | Cell penetrating peptide | Osmotic hypertonic/ hypotonic loading |
|---|---|---|
| Dextran 10K | Dextran 10K | Dextran 10K |
| Dextran 500K | Dextran 3K | Dextran 3K |
| FITC-Albumin | Dextran 500K | Dextran 500K |
| FITC-Bovine IGG | FITC-albumin | FITC-albumin |

| Endocytosis | Cell penetrating peptide | Osmotic hypertonic/ hypotonic loading |
|---|---|---|
| FITC-F(ab)2 | FITC-Bovine IGG | FMLP |
| Histone H1 | FITC-F(ab)2 | Histone H1 |
| Lucifer yellow-slow uptake | FMLP | Lucifer Yellow |
| PE | Histone H1 | PE (PHYCOERYTRIN) |
| Rabbit IGG | Lucifer yellow | Rabbit IGG |
| Soybean Trypsin Inhibitor | PE | Soybean Trypsin Inhibitor |
| Doxorubicin | Rabbit IGG | Doxorubicin |
| Olaparib | Soybean Trypsin Inhibitor | |
| Paclitaxel | | |

In some embodiments, the loading step comprises the use of dextran as a lyophilizing agent. In some embodiments the drug is an antibody. In some embodiments when the drug is an antibody, the drug is labeled with FITC (fluorescein isothiocyanate or 3',6'-dihydroxy-6-isothiocyanatospiro[2-benzofuran-3,9'-xanthene]-1-one).

In some embodiments, drug-loaded platelets, drug-loaded platelet derivatives, or drug-loaded thrombosomes may shield the drug from exposure in circulation, thereby reducing or eliminating systemic toxicity (e.g. cardiotoxicity) associated with the drug. In some embodiments, drug-loaded platelets, drug-loaded platelet derivatives, or drug-loaded thrombosomes may also protect the drug from metabolic degradation or inactivation. In some embodiments, drug delivery with drug-loaded platelets, drug-loaded platelet derivatives, or drug-loaded thrombosomes may therefore be advantageous in treatment of diseases such as cancer, since drug-loaded platelets, drug-loaded platelet derivatives, or drug-loaded thrombosomes facilitate targeting of cancer cells while mitigating systemic side effects. In some embodiments, drug-loaded platelets, drug-loaded platelet derivatives, or drug-loaded thrombosomes may be used in any therapeutic setting in which expedited healing process is required or advantageous. In some embodiments, the therapeutic indications for cargo to be loaded into platelets include, for example, targeted depletion of cancer cells with chemotherapy drugs and therapeutic or prophylactic treatment of bacterial infection at site of injury with antibiotics.

In some embodiments, provided herein is a method of treating a disease as disclosed herein, comprising administering drug-loaded platelets, drug-loaded platelet derivatives, or drug-loaded thrombosomes as disclosed herein. In some embodiments, provided herein is a method of treating a disease as disclosed herein, comprising administering cold stored, room temperature stored, cryopreserved thawed, rehydrated, and/or lyophilized platelets, platelet derivatives, or thrombosomes as disclosed herein.

Examples of diseases (therapeutic indications) that may be treated with the drug-loaded platelets are as follows:

| Therapeutic indications |
|---|
| Acute lymphoblastic leukemia (ALL) |
| Acute myeloid leukemia (AML) |
| Breast cancer (can also be used as an adjuvant therapy for metastasized breast cancer post-surgery) |
| Gastric cancer |
| Hodgkin lymphoma |
| Neuroblastoma |
| Non-Hodgkin lymphoma |
| Ovarian cancer |
| Small cell lung cancer |
| Soft tissue and bone sarcomas |
| Thyroid cancer |
| Transitional cell bladder cancer |
| Wilms tumor |
| Cancer |

Examples of cargo and therapeutic indications for cargo(s) to be loaded into platelets are as follows:

| Cargo | Therapeutic indications |
|---|---|
| Chemotherapy drug (e.g., DOX, Olaparib, Paclitaxel) | Acute lymphoblastic leukemia (ALL) |
| | Acute myeloid leukemia (AML) |
| | Breast cancer (can also be used as an adjuvant therapy for metastasized breast cancer post-surgery) |
| | Cancer |
| | Gastric cancer |
| | Hodgkin lymphoma |
| | Neuroblastoma |
| | Non-Hodgkin lymphoma |
| | Ovarian cancer |
| | Small cell lung cancer |
| | Soft tissue and bone sarcomas |
| | Thyroid cancer |
| | Transitional cell bladder cancer |
| | Wilms tumor |

In some embodiments, a drug may be fluorescent or labeled with a fluorescent moiety. For such a fluorescent or labeled drug, a correlation may be established between the fluorescence intensity and its concentration, and such a correlation may then be used to determine the concentration of the drug over a range of values. For example, FIG. 7 illustrates the correlation between fluorescence and concentration for doxorubicin. As FIG. 7 shows, the value of the concentration for doxorubicin in μM is determined according to the equation $$X = (Y + 344.92)/996.6$$

where Y is the fluorescence and X is the concentration.

An analogous correlation can be derived for the value of the amount of doxorubicin in mg:

$$\text{mg of doxorubicin} = \text{concentration (μmol/L)} \times 543.42 \text{ g/mol} \times 50 \text{ μl/well}/10^9$$

or $$\text{mg of doxorubicin} = (\text{\# μmol DOX/L})(\text{mol}/10^6 \text{ μmol})(543.52 \text{ g/mol})(10^3 \text{ mg/g})(\text{L}/10^3 \text{ ml})(1 \text{ ml}/10^3 \text{ ml})(50 \text{ μl/well})$$

An analogous correlation can be derived for the value of the amount of doxorubicin in mg/cell:

$$\text{mg/cell} = \text{mg (Intracellular+Membrane-bound doxorubicin)/total \# of cells in a well.}$$

Thus, the concentration of doxorubicin may be quantified from its excitation/emission spectra.

Examples of loading buffer that may be used are shown in Tables 1-4:

TABLE 1

Loading Buffer

| Component | Concentration (mM unless otherwise specified) |
|---|---|
| NaCl | 75.0 |
| KCl | 4.8 |
| HEPES | 9.5 |
| NaHCO3 | 12.0 |
| Dextrose | 3 |
| Trehalose | 100 |
| Ethanol | 1% (v/v) |

Table 1. Loading Buffer is used to load platelets via endocytosis at 37° C. with gentle agitation as sample is placed on a rocker. Adjust pH to 6.6-6.8

TABLE 2

Buffer A

| Component | Concentration (mM unless specified otherwise) |
|---|---|
| CaCl$_2$ | 1.8 |
| MgCl$_2$ | 1.1 |
| KCl | 2.7 |
| NaCl | 137 |
| NaH$_2$PO$_4$ | 0.4 |
| HEPES | 10 |
| D-glucose | 5.6 |
| pH | 6.5 |

Table 2. Buffer A is used for loading platelets with liposome encapsulated drug. Incubation done at 37° C. with gentle agitation as sample is placed on a rocker.

TABLE 3

Buffer B

| Component | Concentration (mM unless otherwise specified) |
|---|---|
| Buffer and Salts | Table 4 (below) |
| BSA | 0.35% |
| Dextrose | 5 |
| pH | 7.4 |

Table 3. Buffer B is used when incubating platelets with fluorophore conjugated antibodies for flow cytometry. This incubation is done at room temperature in the dark.
Albumin is an optional component of Buffer B

TABLE 4

Concentration of HEPES and of Salts in Buffer B

| Component | Concentration (mM unless otherwise specified) |
|---|---|
| HEPES | 25 |
| NaCl | 119 |
| KCl | 5 |

TABLE 4-continued

Concentration of HEPES and of Salts in Buffer B

| Component | Concentration (mM unless otherwise specified) |
|---|---|
| CaCl$_2$ | 2 |
| MgCl$_2$ | 2 |
| Glucose | 6 g/l |

In Table 4 the pH adjusted to 7.4 with NaOH
Albumin is an optional component of Buffer B
In some embodiments, drug-loaded platelets are prepared by incubating the platelets with the drug in a loading buffer having the components shown in the table below.

In some embodiments, the loading buffer has the components as listed above in Table 1.

In some embodiments, incubation is performed at 37° C. using a platelet to drug volume ratio of 1:2, using different incubation periods.

Example 1. Doxorubicin-Loaded Platelets

Doxorubicin-loaded platelets were prepared by incubating the platelets with doxorubicin in a loading buffer having the components shown in Table 5. Protocol 1 (described below) was used.

The platelet concentration in the loading buffer was 200,000 platelets/µl. The loading buffer had the following components:

TABLE 5

| Component | Concentration (mM unless specified otherwise) |
|---|---|
| NaCl | 75.0 |
| KCl | 4.8 |
| HEPES | 9.5 |
| NaHCO3 | 12.0 |
| Dextrose | 3 |
| Trehalose | 0.1M |
| Ethanol | 1% (v/v) |

Incubation was performed at 37° C. using a platelet to drug volume ratio of 1:2, using different incubation periods.

Figure 4:
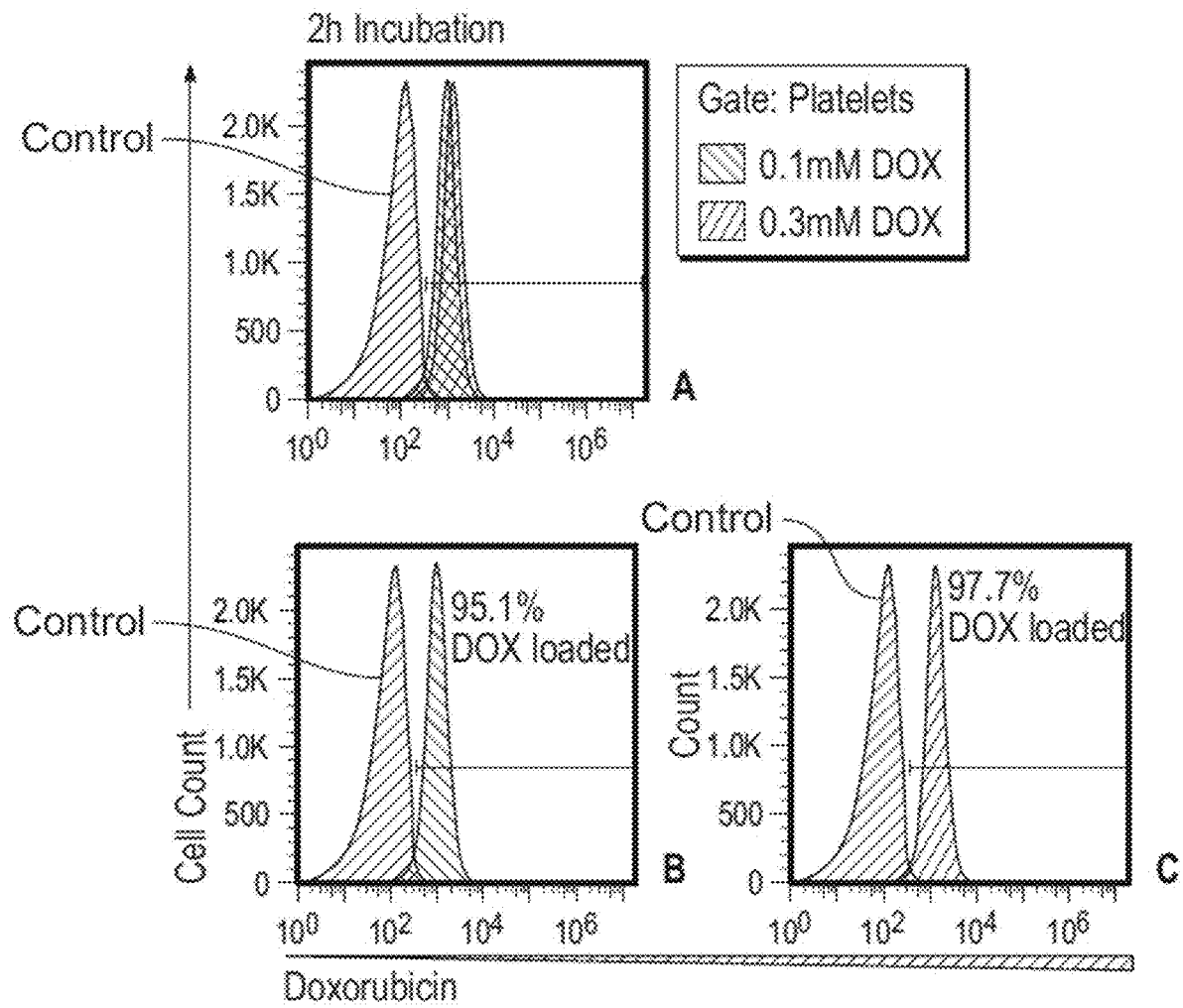
FIGS. 4A-4C shows flow cytometry data relating to the endocytic loading of DOX into platelets. The top graph shows amalgamated data that includes the bottom left graph (Doxorubicin at 0.1 mM) and the bottom right graph (Doxorubicin at 0.3 mM).

The drug-loading method was evaluated by flow cytometry to obtain a relative quantification of loading efficiency as mean fluorescence intensity of Doxorubicin in drug-loaded platelets. Platelets were evaluated for function by ADP and/or TRAP stimulation post-loading. The resulting amounts of doxorubicin load as a function of incubation time are provided in FIG. 1. Platelets were loaded with fluorescent DOX (excitation 470 nm, emission 560 nm) and evaluated by flow cytometry for fluorescence uptake. CD42b+ platelets load increasingly more DOX over time. % of platelets loaded with DOX is >90%, as shown in FIG. 4. DOX=doxorubicin. N=1.

Figure 2:
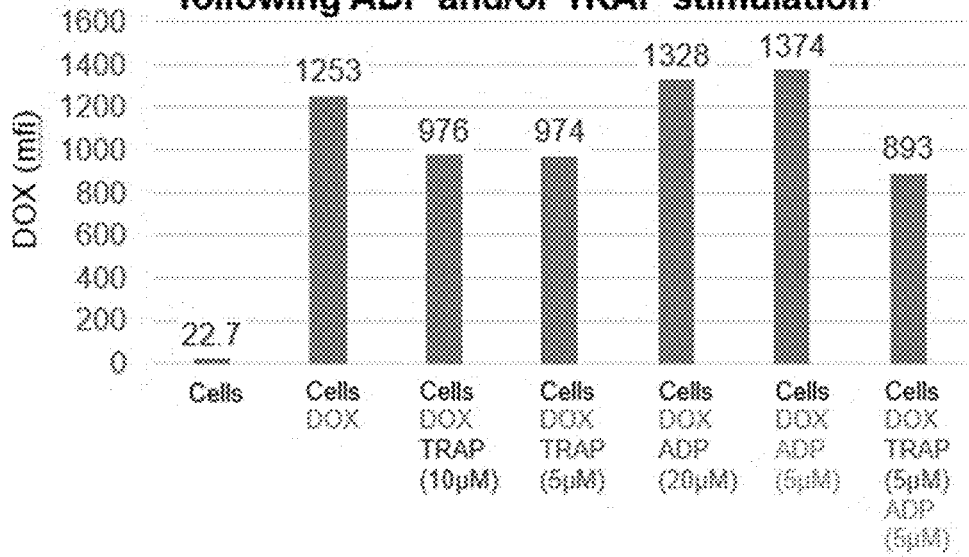
FIG. 2 shows resulting amounts of doxorubicin load in platelets following ADP and TRAP simulation when evaluated by flow cytometry.

In FIG. 2, DOX loaded platelets were incubated in loading buffer with ADP and/or TRAP for 10 minutes at room temperature to stimulate drug release. Following this incubation, flow cytometry was performed to assess decrease in drug load. DOX+ populations were gated on CD42b+ platelets. TRAP partially induced DOX release from drug-loaded platelets while ADP did not.

There is no synergistic effect of TRAP and ADP on DOX release from loaded platelets. ADP=adenosine diphosphate; TRAP=thrombin receptor activating peptide; DOX=doxorubicin. N=1.

Figure 3:
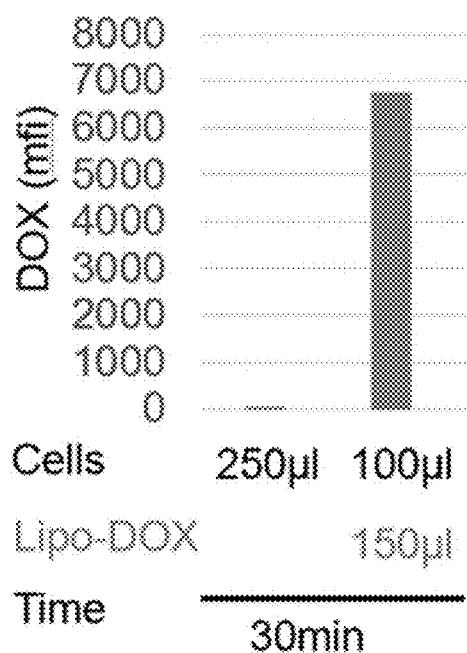
FIG. 3 shows fluorescence intensity as measured by flow cytometry after platelet incubation with DOX encapsulated liposomes.
Figure 5:
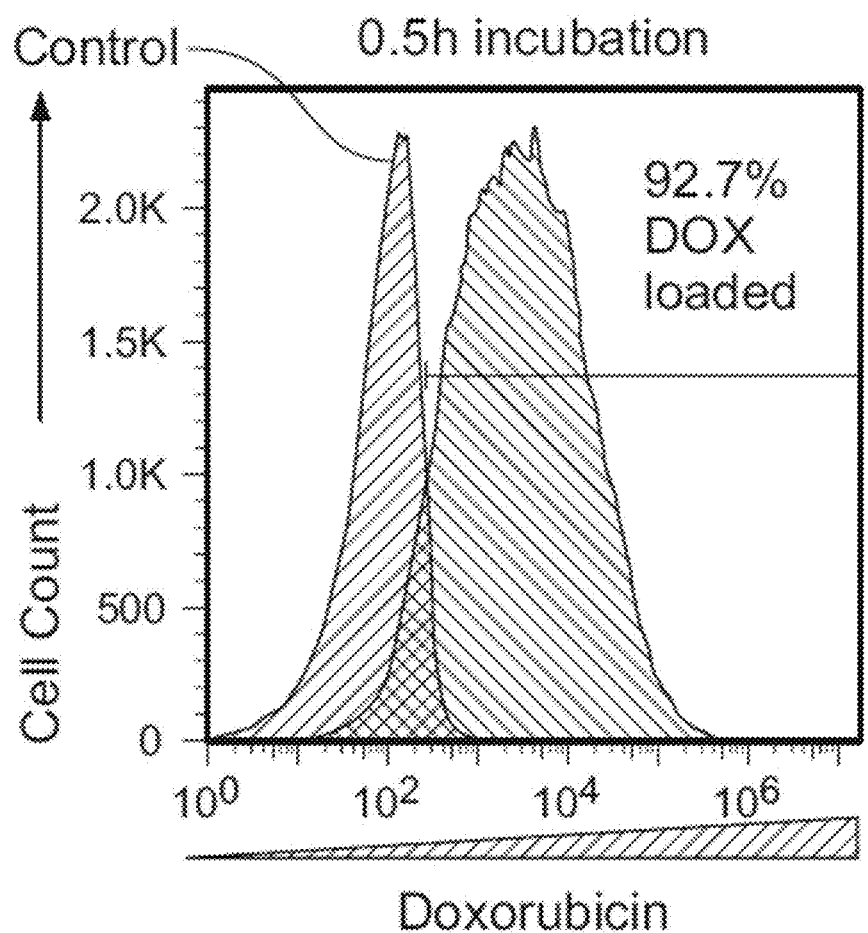
FIG. 5 provides flow cytometry data relating to liposome-mediated loading of Doxorubicin into platelets.

In FIG. 3, platelets (200,000 platelets/μl) were loaded with liposome encapsulated DOX (2 mg/ml). Liposome encapsulated DOX was prepared by rehydrating lyophilized lipid mixture (from Liposome Kit, Sigma-Aldrich, L4395) with 2 mg/ml DOX in PBS, followed by incubation at 37° C. for 30 minutes. Platelets and liposome encapsulated DOX were incubated at 37° C. for 30 minutes in Tyrode's HEPES buffer (Table 2). Flow cytometry was performed to obtain qualitative quantification of amount of DOX loaded per platelet. % of CD42b+ platelets loaded with liposome encapsulated DOX was >90% as shown in FIG. 5. N=1.

Example 2. Time Course of Endocytic Loading Vs. Liposome-Mediated Loading of Doxorubicin into Platelets The efficiency of Doxorubicin loading into platelets via standard endocytosis or using liposome-encapsulated Doxorubicin ("Doxosomes") was tested.

FIGS. 4A-4C provide data relating to endocytic loading of Doxorubicin into platelets. Platelets were incubated with 0.1 mM Doxorubicin or 0.3 mM Doxorubicin for two hours. Doxorubicin was allowed to enter the platelets via endocytosis. The top graph shows amalgamated data that includes the bottom left graph (Doxorubicin at 0.1 mM) and the bottom right graph (Doxorubicin at 0.3 mM). Doxorubicin was efficiently loaded after two hours of incubation at concentrations of both 0.1 mM and 0.3 mM. For each graph, the left-most curve represents cells only.

FIG. 5 provides data relating to liposome-mediated loading of Doxorubicin into platelets. Platelets were incubated with 13.5 μM of Doxorubicin-containing doxosomes for 0.5 hours. Briefly, a total of 90 μmol of lipids (63 μmol L-A-Phosphatidylcholine, 18 μmol Stearylamine, and 9 μmol Cholesterol) were resuspended in 1 mL of Doxorubicin in PBS to generate the doxosomes. 150 μL of doxosome containing 12 mg/mL of liposome-encapsulated Doxorubicin was incubated with platelets to a final doxosome concentration of 13.5 μM. Doxorubicin was efficiently loaded after 0.5 hours of incubation with the doxosomes.

As can be seen from the Figures, loading of doxorubicin occurred efficiently both via doxosomes (FIG. 5) and using endocytotic loading (FIGS. 4A-4C).

Exemplary protocols for the loading of platelets with doxorubicin are shown below:

Protocol 1. Loading Platelets with DOX Via Endocytosis

The starting apheresis platelet material was pooled and characterized. The platelet pool was acidified to pH 6.6-6.8 using Acid Citrate Dextrose solution. Platelets were isolated by centrifugation at 1500 g for 20 minutes, with slow acceleration and braking. The supernatant plasma was aspirated and disposed of.

The platelets were suspended in the loading buffer of Table 1 at a concentration of 200,000 platelets/μl. While the platelets were being centrifuged, a doxorubicin ("DOX") solution having a concentration of 0.3 mM in the loading buffer was prepared as follows: a solution of DOX in water (50 mg/ml) was pre-warmed at 37° C. for 20 minutes; DOX was then incubated in the loading buffer at a concentration of 0.3 mM at 37° C. for 20 minutes, periodically subjecting it to a vortex.

The platelets and DOX (1 ml platelets at 200,000 platelets/μl+2 ml DOX at 0.3 mM) were then mixed and the mixture was incubated at 37° C. for 2 hours. The resulting DOX-loaded platelets were lyophilized.

Optionally, the lyophilized DOX-loaded platelets could be suspended in water at a concentration suitable for the uses disclosed herein.

Protocol 2. Loading Platelets with Liposome Encapsulated DOX

The starting apheresis platelet material was pooled and characterized. The platelet pool was acidified to pH 6.6-6.8 using Acid Citrate Dextrose solution. Platelets were isolated by centrifugation at 1500 g for 20 minutes, with slow acceleration and braking. The supernatant plasma was aspirated and disposed of.

The platelets were suspended in Buffer A at a concentration of 200,000 platelets/μl. The components of Buffer A are shown above Table 2.

TABLE 6

| Tyrode's HEPES Buffer | |
|---|---|
| Component | Concentration (mM) |
| $CaCl_2$ | 1.8 |
| $MgCl_2$ | 1.1 |
| KCl | 2.7 |
| NaCl | 137 |
| $NaH_2PO_4$ | 0.4 |
| HEPES | 10 |
| D-glucose | 5.6 |
| pH | 6.5 |

While the platelets were being centrifuged, liposome-encapsulated doxorubicin ("DOX") was prepared as follows: lyophilized phospholipids (Sigma-Aldrich, SKU # DOX-1000) were rehydrated with a 2 mg/ml solution of DOX in PBS; the rehydrated mixture was then subjected it to a vortex for 30 seconds and incubated at 37° C. for 30 minutes.

The platelets in Tyrode's HEPES buffer and the liposomal DOX were then mixed and the mixture was incubated at 37° C. for 30 minutes.

The resulting DOX-loaded platelets were washed in 1 mL Tyrode's HEPES buffer to remove unincorporated liposome by centrifugation at 1500 g for 20 minutes.

Optionally, the lyophilized DOX-loaded platelets could be suspended in water at a concentration suitable for the uses disclosed herein.

Protocol 3. Loading Platelets with Liposome Encapsulated DOX

This protocol was similar to Protocol 2 herein, except that the buffer was as follows instead of the buffer of Table 6 above:

TABLE 7

| Tyrode's HEPES Buffer (plus PGE1) | |
|---|---|
| Component | Concentration (mM) |
| $CaCl_2$ | 1.8 |
| $MgCl_2$ | 1.1 |
| KCl | 2.7 |
| NaCl | 137 |
| $NaH_2PO_4$ | 0.4 |
| HEPES | 10 |
| D-glucose | 5.6 |
| pH | 6.5 |
| Prostaglandin E1 (PGE1) | 1 μg/ml |

Protocol 4. Loading Platelets with Liposome Encapsulated DOX

This protocol was similar to protocol 2 herein, except that the buffer of Table 1 was used (shown again below) instead of the buffer of Table 6 above:
Experimental Results. Effect of Buffer on Liposome-Mediated Loading of Doxorubicin into Platelets Platelets were incubated with doxosomes containing fluorescent doxorubicin as described above in Example 2 in the presence of trehalose-containing loading buffer (as shown in Table 1) or HMT (as shown in Table 7) As can be seen in FIG. 6, trehalose-containing loading buffer increased the total amount of Doxorubicin that was loaded as compared to HMT.

FIGS. 6A and 6B provide a comparison of doxosome loading efficiency between conventional HMT buffer (Protocol 3, shown in continuous line) and trehalose-containing loading buffer (Protocol 4, shown in individual points) described herein. The x axis represents the amount of doxosome added to the platelets. The y axis represents mean-fluorescence intensity. FIG. 6A provides the doxosome loading efficiency of loading platelets with CD42b antibodies to define the platelets while FIG. 6B provides the doxosome loading efficiency of platelets without CD42b. A higher drug load is obtained with the trehalose-containing loading buffer of Protocol 4 as compared to the conventional HMT loading buffer at all points after about 20 minutes.

Example 3—Determination of Amount of Doxorubicin ("DOX") in a Platelet

Protocol A:
Fresh donor platelets were provided. Incubation with the drug took place by endocytosis at 37 C for 3 hours in a rocker at low frequency, in the presence of a buffer containing HMT and 1 µM PGE1. The correlation between fluorescence and concentration is shown in FIG. 7.

Calculations of Amounts—Example 3A-1

1) Concentration:
In a well containing 50 µL and having a concentration of 250K cells per the intracellular doxorubicin fluorescence was 10811 and the membrane-bound doxorubicin fluorescence was 1263. Calculating the concentration from the formula $X=(Y+344.92)/996.6$, where Y is the fluorescence and X is the concentration, provides an intracellular concentration 11 µM and a membrane-bound concentration of 2 µM.
2) Quantity in mg:
The amount in mg is calculated from the formula:

mg of doxorubicin=concentration (µmol/L)×543.42× 50/10$^9$

3) Quantity in mg/Platelet:
The amount in mg/platelet is calculated from the formula:

(Intracellular DOX amount (per well)+membrane-bound DOX amount (per well))/total # of platelets in a well For example, for an intracellular amount of $3.04 \times 10^{-4}$ mg and a membrane-bound amount of $4.38 \times 10^{-5}$ mg, if there are 250,000 cells/µl and 50 µl/well, then the total amount will be $2.78 \times 10^{-11}$ mg/platelet.

The calculations have a percentage error of 7.16%, calculated as follows:
Intracellular concentration of doxorubicin: 11 µM
membrane-bound concentration of doxorubicin: 2 µM.
Soluble concentration of doxorubicin: 298 µM.
Total concentration of doxorubicin: 290 µM.

% error=[(298+11+2)−290)/290]×100%=7.16%

Calculations of Amounts—Example 3A-2

1) Concentration:
In a well containing 50 µL and having a concentration of 125K cells per the intracellular doxorubicin fluorescence was 7496 and the membrane-bound doxorubicin fluorescence was 438. Calculating the concentration from the formula $X=(Y+344.92)/996.6$, where Y is the fluorescence and X is the concentration, provides an intracellular concentration 8 µM and a membrane-bound concentration of 1 µM.
2) Quantity in mg:
The amount in mg in a 50 µL sample is calculated from the formula:

mg of doxorubicin=concentration (µmol/L)×543.42× 50/10$^9$

3) Quantity in mg/Platelet:
The amount in mg/platelet is calculated from the formula:

(Intracellular DOX amount+membrane-bound DOX amount)/total # of platelets in a well For example, for an intracellular amount of $2.14 \times 10^{-4}$ mg and a membrane-bound amount of $2.13 \times 10^{-5}$, if there are 125,000 cells/µl and 50 µl/well, then the total amount will be $1.88 \times 10^{11}$ mg/platelet.
The calculations have a percentage error of 1.94%, calculated as follows:
Intracellular concentration of doxorubicin: 8 µM
membrane-bound concentration of doxorubicin: 1 µM.
Soluble concentration of doxorubicin: 295 µM.
Total concentration of doxorubicin: 310 µM.

% error=[(295+8+1)−310)/310]×100%=1.94%

Protocol B:
Four apheresis units were pooled. Incubation with the drug took place at 37 C for 4 hours in a rocker at low frequency, in the presence of a buffer containing HMT and 1 µM PGE1. The correlation between fluorescence and concentration is shown in FIG. 13.

Calculations of Amounts—Example 3B-1

1) Concentration:
Calculations were performed in a manner analogous to Example 3A-1 and 3A-2 above, the correlation between fluorescence and concentration was based on a standard curve.
The resulting quantity of DOX in mg/platelet for various values of cells/µl is as follows:

| Cells/µl | DOX (mg/cell) |
| --- | --- |
| 108K | $4.4 \times 10^{-6}$ |
| 235K | $3.2 \times 10^{-6}$ |
| 454K | $2.2 \times 10^{-6}$ |
| 915K | $1.5 \times 10^{-6}$ |
| 1448K | $1.0 \times 10^{-7}$ |
| 1745K | $9.3 \times 10^{-7}$ |

Figure 8:
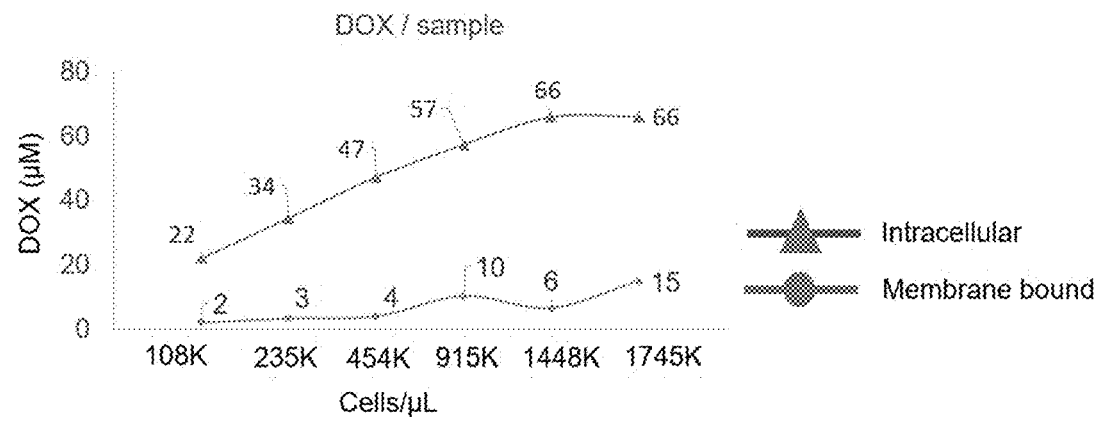
FIG. 8 shows the total concentration of (a) intracellular doxorubicin (triangle), and (b) membrane-bound doxorubicin (circle), with increasing concentration of platelets/μL.
Figure 9:
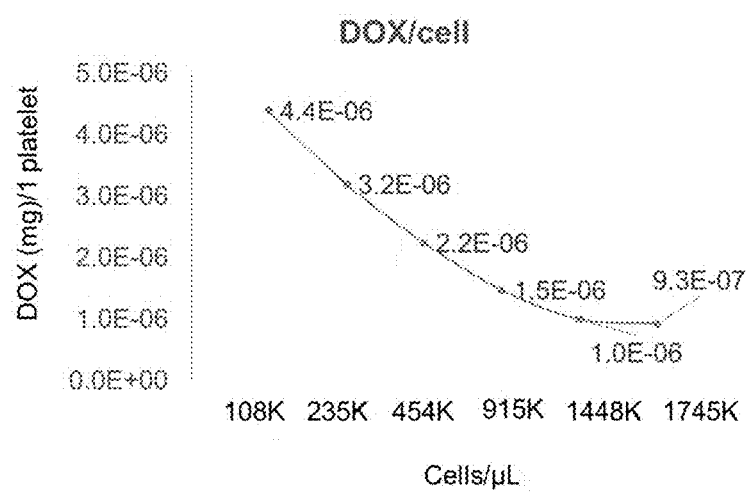
FIG. 9 shows how for a given concentration of doxorubicin (DOX) (0.2 mM), the amount of DOX/platelet decreases as the number of platelets increases.

FIGS. 8 and 9 are based on the same data showing that the total amount of DOX loaded into platelets increases as a function of increasing platelet count, but the amount of DOX loaded into an individual platelet decreases.

FIG. 8 shows the total concentration of (a) intracellular doxorubicin, and (b) membrane-bound doxorubicin, with increasing concentration of platelets/µL.

FIG. 9 shows how for a given concentration of doxorubicin (DOX) (0.2 mM), the amount of DOX/platelet decreases as the number of platelets increases.

Example 4. Comparison of Amount of Drug Loaded with Loading Buffer and with HMT Buffer Platelets pooled from eight apheresis units, at a concentration of (250,000 cells/µL, were incubated in either the Loading Buffer of Table 1 (LB in FIG. 12) or HMT containing PGE1 (1 µM) (Table 7) in the presence of DOX (0.6 mM or 0.36 mg/ml) compared to a control with no DOX for 3 hours at 37° C. Following incubation, platelets were isolated from buffer via centrifugation (Beckman Coulter Microfuge 18 Centrifuge, 845×g, 10 minutes, room temperature), then washed twice with LB or HMT using the same centrifugation setting as stated. After that, the platelets were sonicated 3 times to release intracellular DOX at 26 kHz for 30 seconds with 2-5 minutes interval of rest at room temperature. These samples are then centrifuged (Eppendorf Centrifuge 5424, 18,000 G, 20 minutes, room temperature) to separate intracellular DOX (supernatant) from membrane bound DOX (pellet). The pellet was resuspended in 1 ml of buffer (HMT or LB) then sonicated 3 times at previously stated setting to generate homogenized sample of membrane bound DOX in buffer. Quantification of DOX is achieved with 500 nm excitation and 600 nm emission using the TECAN Infinite M200 PRO. A 96-welled polystyrene, half area, non-treated, black with clear flat bottom plate (Corning) is used in which 504, of sample is plated per well in triplicates. DOX load per platelet (mg/cell) is calculated based on standard curve (linear regression, $R^2$=0.9873 for cell lysate in HMT, $R^2$=0.9902) generated from serial dilution of cell lysate.

Figure 12:
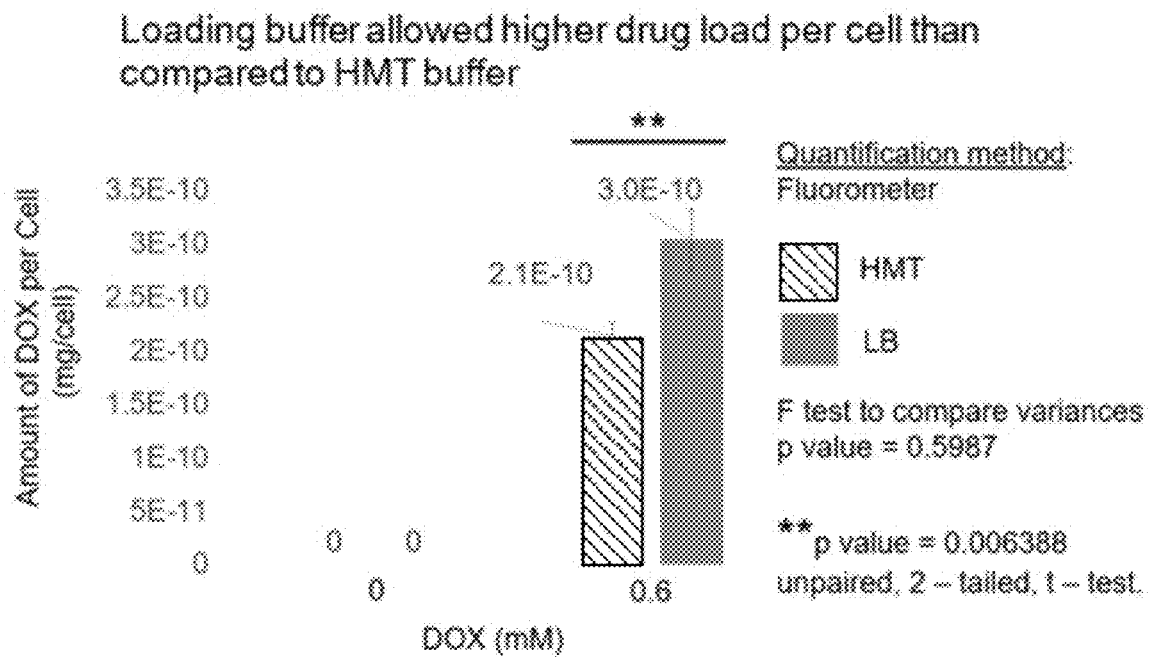
FIG. 12 shows a comparison of the amount of doxorubicin loaded into platelets with loading buffer (right) vs. the amount loaded with HMT buffer (left).

As shown in FIG. 12, the loading buffer allowed higher drug load per cell than compared to HMT buffer.

Example 5—Induced Drug Release from Doxorubicin-Loaded Platelets

Pooled apheresis platelets from between 8 and 11 apheresis units (defined as 200-400 mL of plasma from a single donor) were diluted to 250,000 cells/µL. A test group included 0.2 mM doxorubicin (DOX) and a control group contained no agonist. Both the test and control groups were incubated in a HMT buffer of pH 6.8 containing 1 µM Prostaglandin E1 (PGE1) for 3 hours at 37° C.

Any excess drug not loaded into the platelet was removed by subjecting the test group to centrifugation at 800×g for 10 minutes at room temperature and by discarding the supernatant. The drug-loaded cells of the test group were resuspended to the same concentration in HMT buffer at pH 7.4 then stimulated with agonists including collagen, ADP, thrombin, arachidonic acid (AA) and thrombin receptor activating peptide (TRAP-6) for 15 minutes at room temperature. The supernatant was harvested by centrifugation as described above.

The control group for intracellular drug was prepared by three rounds of vibration sonication for 30 seconds at 20 kHz prior to centrifugation.

Fifty µl of supernatant of the test and control groups was applied to fluorescent compatible clear flat bottom ½ area of 96 well micro-titer plates and analyzed on a Tecan Sapphire plate reader with excitation at 500 nm and emission at 600 nm and the released Doxorubicin quantified relative to a standard curve obtained under the same conditions.

Figure 10:
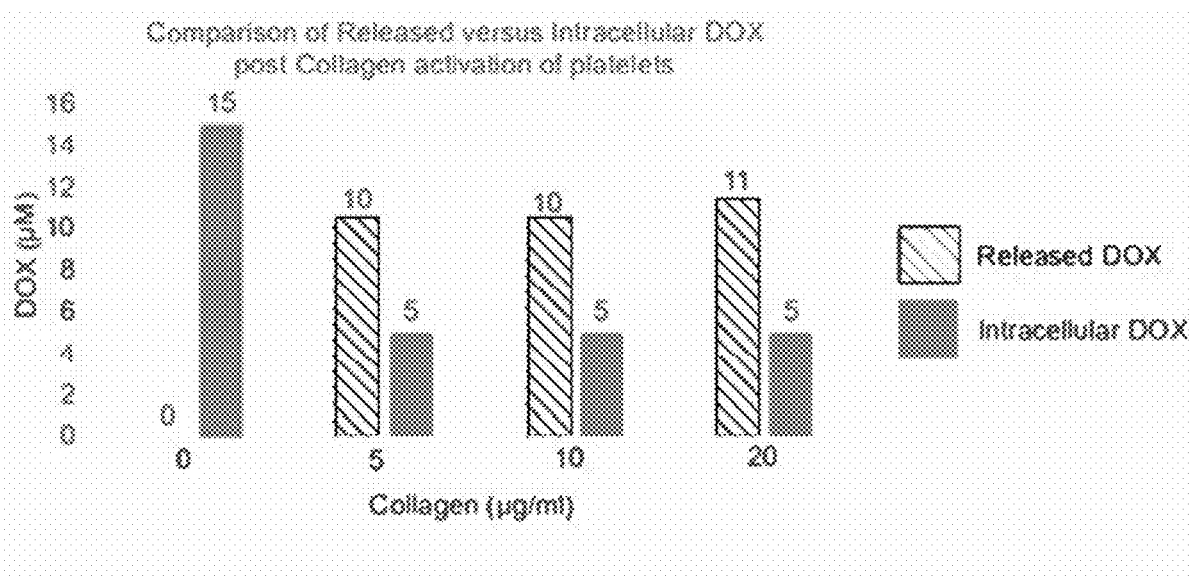
FIG. 10 shows the effect of collagen on inducing drug release from doxorubicin-loaded platelets. Released DOX is plotted on the left and intracellular DOX is plotted to the right for each group.

The amount of released and intracellular DOX in DOX-loaded platelets when stimulated with varying amounts of collagen are shown in FIG. 10. The effect of varying amounts of collagen on inducing drug release on DOX-loaded platelet, as measured by light excitation and emission, is shown in FIG. 10 in comparison with a control group containing no collagen.

Figure 11:
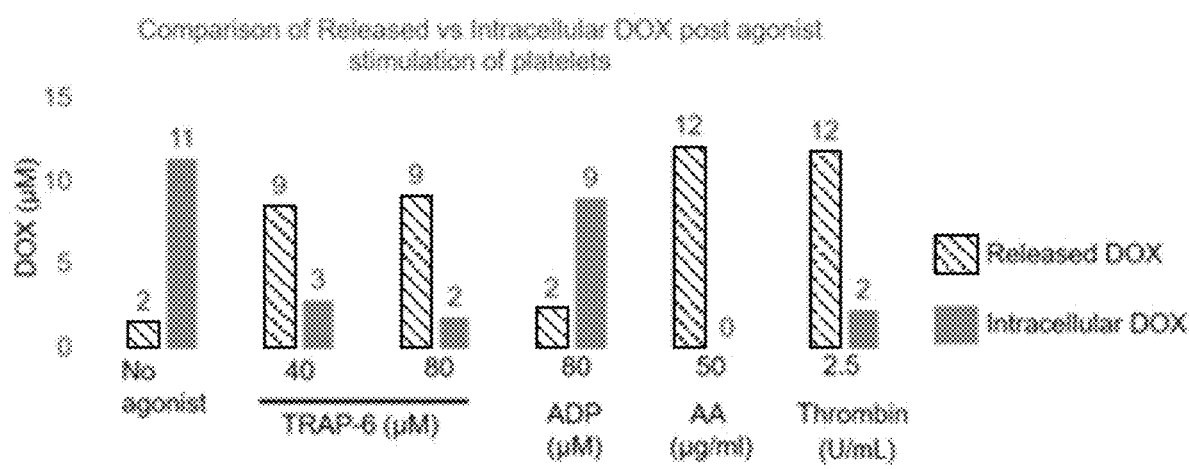
FIG. 11 shows the effect of TRAP-6, ADP, arachidonic acid, and thrombin on inducing drug release from doxorubicin-loaded platelets. Released DOX is plotted on the left and intracellular DOX is plotted to the right for each group.

The amount of released and intracellular DOX in DOX-loaded platelets when stimulated with TRAP-6, ADP, AA, and thrombin are shown in FIG. 11. The effect of different agonists on inducing drug release on DOX-loaded platelet, as measured by light excitation and emission, is shown in FIG. 11 in comparison with a control group containing no agonist.

Example 6—Loading Buffer Allows Higher Drug Load Per Cell than HMT Buffer

FIG. 12 shows a higher drug load per cell when using loading buffer as compared to HMT buffer. The amount of DOX is measured in mg/cell by a fluorometer.

Example 7—DOX Induced Aggregation of Platelets

Figure 13A:
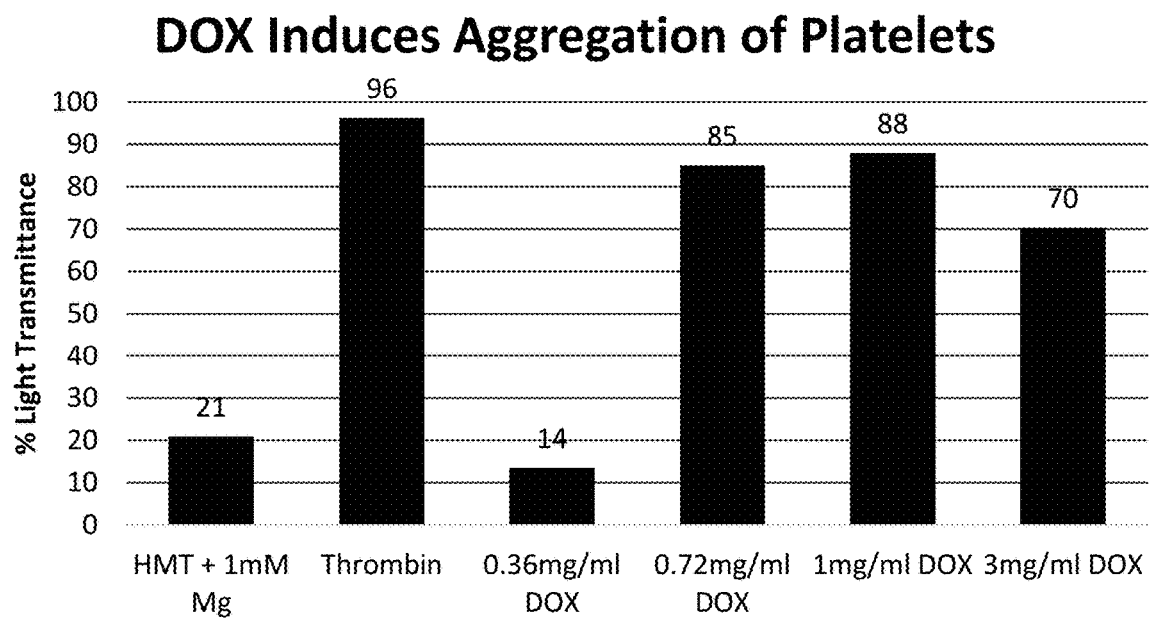
FIG. 13A shows the effect of DOX on the aggregation of platelets as measured by light transmittance.

Loading platelets with DOX causes the platelets to aggregate resulting in a decrease in platelet count. The extent of platelet aggregation is measured as a function of the transmittance of light through a stirred suspension of platelets on an AggRAM. Platelets as single cells in a suspension are too turbid for light to effectively pass through. However, when platelets aggregate they fall out of suspension and allow more light to pass through, thus increasing the transmittance. FIG. 13A shows the DOX induced platelet aggregation measured by percent light transmittance.

Platelets were treated with 0.36 mg/ml, 0.72 mg/mL, 1 mg/mL, and 3 mg/ml of DOX. Thrombin was used as a positive control. HMT and 1 mM magnesium were used as a negative control (FIG. 13A).

Figure 13B:
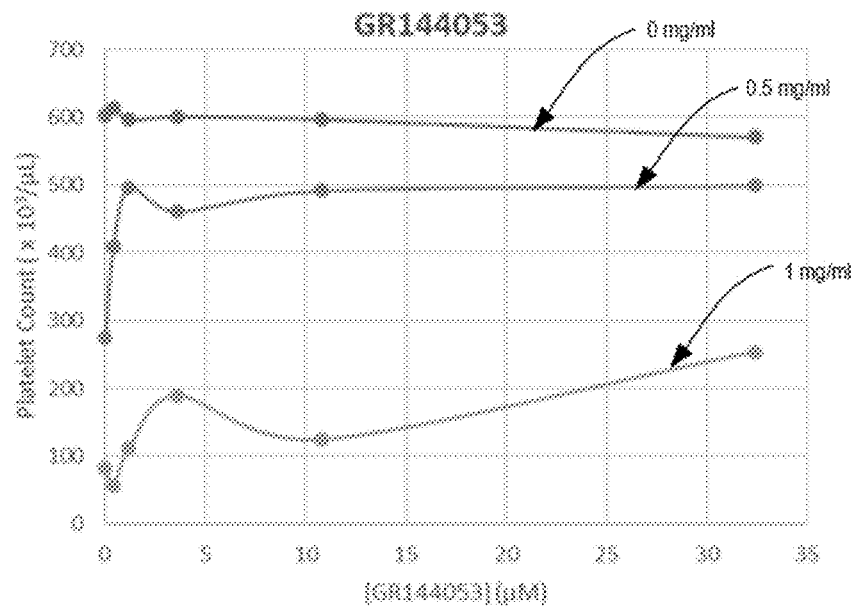
FIG. 13B shows the effect of the addition of a GPIIb/IIIa inhibitor, GR 144053, on the aggregation of platelets by 0 (top), 0.5 mg/mL (middle), or 1 mg/mL (bottom) doxorubicin as measured by light transmittance.
Figure 13C:
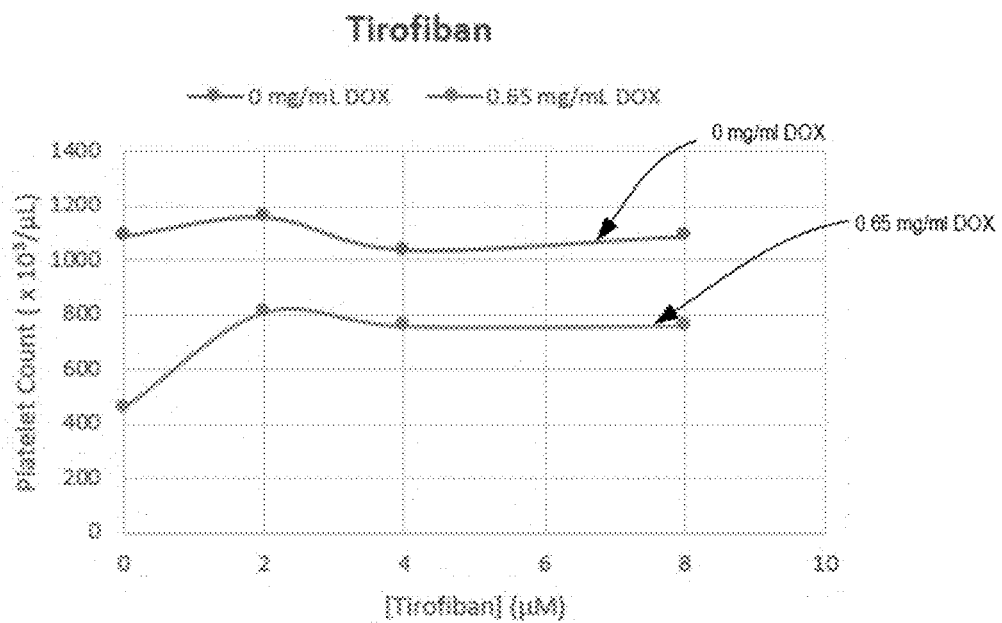
FIG. 13C shows the effect of the addition of Tirofiban on the aggregation of platelets by 0 (top) or 0.65 mg/mL (bottom) doxorubicin.

The concentration of platelets (count) is determined on an AcT-Diff hematology analyzer. As shown in FIG. 13B-C, the platelet count decreases with increasing DOX concentration after incubation for 3 hours. The only anti-platelet compounds that shows effective inhibition of DOX-induced aggregation in this assay were the GPIIb/IIIa inhibitors GR144053 and Tirofiban (See Table 1)

FIG. 13B shows that a GPIIb/IIIa inhibitor GR 144053 (>1.2 µM) limited reduction of platelet count following coincubation with 0.5 mg/ml DOX for 1 hour at 37° C. The data were generated from platelets pooled from seven apheresis units. Platelets (600,000 cells/µL), DOX (0 mg/ml top line, 0.5 mg/ml middle line, 1 mg/ml bottom line), and GR 144053 (0, 0.4, 1.2, 3.6, 10.8, and 32.4 µM. Tocris Bioscience Cat. #1263.) were incubated in loading buffer for 1 hour at 37° C. Following incubation, platelets were quantified via Coulter AcoT diff2 Hematology Analyzer (×10³/µL).

Example 8—Platelets Retain DOX after Cryopreservation or Lyophilization

The concentration of Dox loaded into platelets remains the same after cryopreservation. Platelets were incubated with 600 µM Dox in the presence of PGE1 and GR144053 at 37° C. for 3 hours, then washed, and subjected to cryopreservation in loading buffer containing 6% polysucrose.

Figure 17:
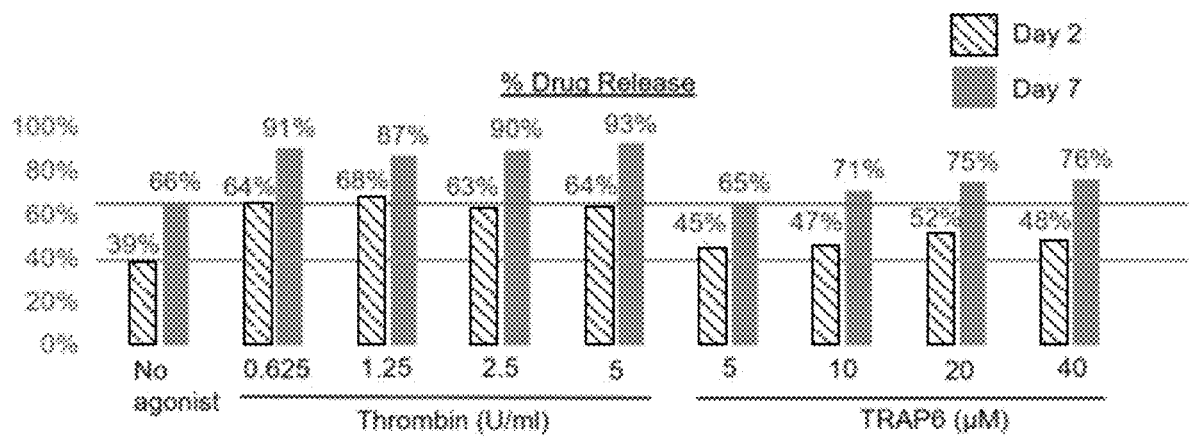
FIG. 17 shows the release of DOX from within platelets in response to strong platelet activating agents after cryopreservation for up to 7 days. Day 2 is plotted on the left and Day 7 is plotted on the right for each group.

After cryopreservation, DOX can be released from within platelets in response to strong platelet activating agents described herein. The released DOX concentration was measured by fluorescence on a plate reader after 2 (left hand columns) and 7 (right hand columns) days after incubation and centrifugation (FIG. 17). The released DOX is shown here as a percentage of the total DOX measured before cryopreservation. The bottom line marks the DOX release without agonist at 2 days and the top line marks the DOX release without agonist after 7 days.

A series of quality control experiments were performed with DOX loaded thrombosomes. The batch is a large batch measured in apheresis units. The batch contains Sublot A with 98 vials of unloaded thrombosomes and Sublot B with 98 vials of DOX-loaded thrombosomes.

Figure 18:
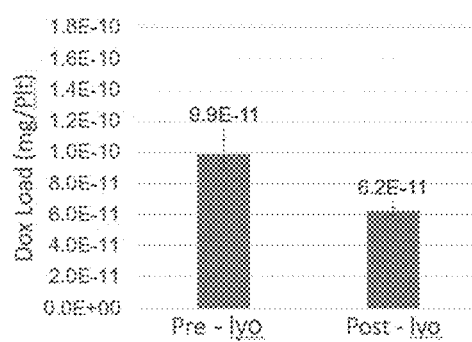
FIG. 18 shows DOX-loaded thrombosomes (mg/Plt) prepared by incubation with 600 μM Dox. Pre-lyo is during preparation before lyophilization and post-lyo is after lyophilization and rehydration of the DOX-loaded Thrombosomes.

DOX-loaded thrombosomes were prepared by incubation with 600 µM DOX then following thrombosomes manufacturing specifications. The concentration of DOX loaded into platelets was measured by fluorescence after sonication as described herein. FIG. 18 shows the concentration of DOX loaded into platelets before and after lyophilization to a dry powder and rehydration was found to be >43% of the concentration measured immediately prior to lyophilization.

Figure 19:
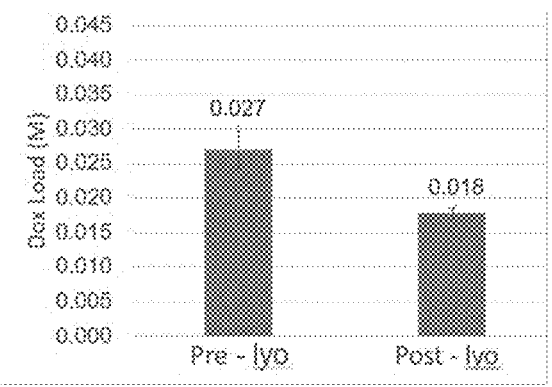
FIG. 19 shows that the intracellular DOX concentration is increased 50-fold prior to lyophilization (platelets) and maintained at 30-fold after lyophilization (thrombosomes) relative to the external DOX concentration during incubation.

FIG. 19 represents the same data from FIG. 18, but the data were converted to molar concentration by using the mean platelet volume (MPV) after DOX loading. FIG. 19 shows that the intracellular DOX concentration is increased 50-fold prior to lyophilization and maintained at 30-fold after lyophilization relative to the external DOX concentration during incubation.

Figure 20:
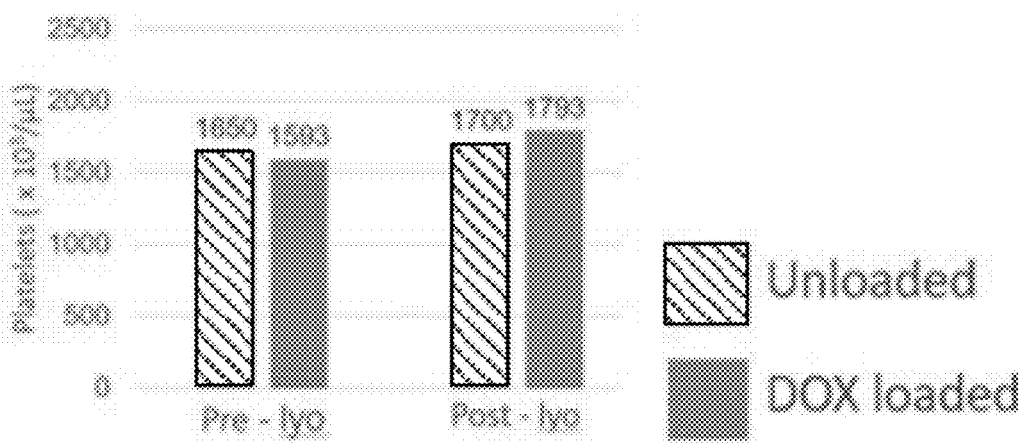
FIG. 20 shows platelet counts according to AcT-Diff hematology analyzer remain unchanged after lyophilization (thrombosomes). Unloaded Thrombosomes is plotted on the left and DOX-loaded Thrombosomes is plotted to the right for each group.

FIG. 20 shows that platelet counts, as measured by the AcT-Diff hematology analyzer, remain mostly unchanged after lyophilization. The target platelet count when preparing the platelet suspensions for lyophilization was $2000 \times 10^3/\mu L$, and should remain similar after lyophilization and rehydration in the same volume used to aliquot the platelet suspensions prior to lyophilization.

Figure 21:
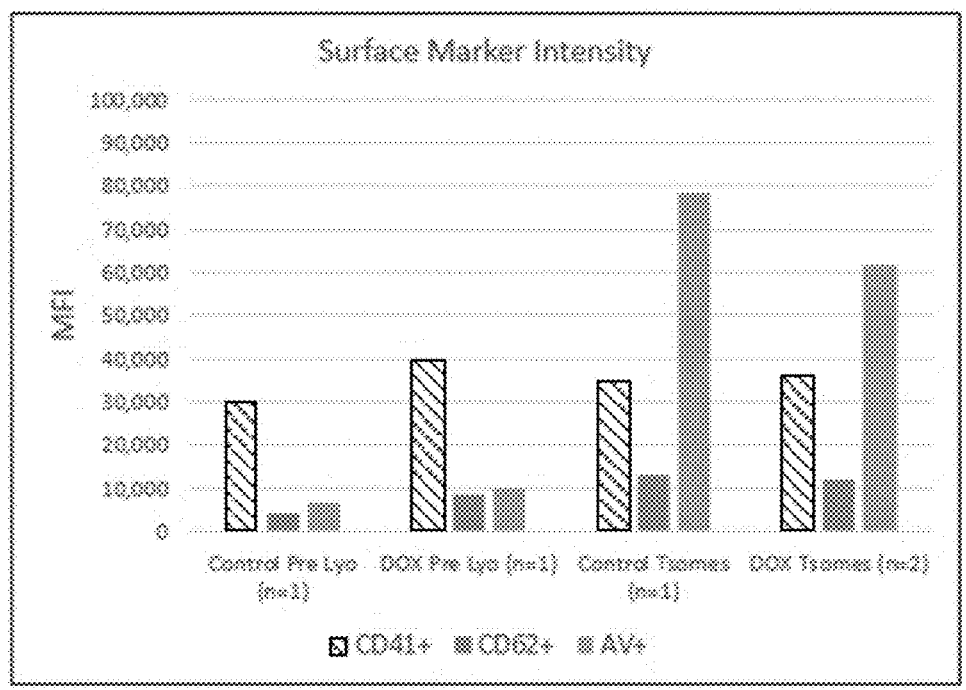
FIG. 21 shows that DOX loaded thrombosomes have similar platelet receptor biomarker expression relative to unloaded thrombosomes immediately prior to (platelets) and after lyophilization (thrombosomes).

FIG. 21 shows that DOX-loaded thrombosomes have similar platelet receptor biomarker expression relative to unlabeled thrombosomes immediately prior to and after lyophilization. CD41 (left hand columns), CD62 (middle columns), and Annexin V (right hand columns) expression levels were measured using fluorescently-labeled antibodies for each receptor. The fluorescent labels were chosen such that DOX fluorescence would not interfere with the antibody fluorescence signal.

Figure 22:
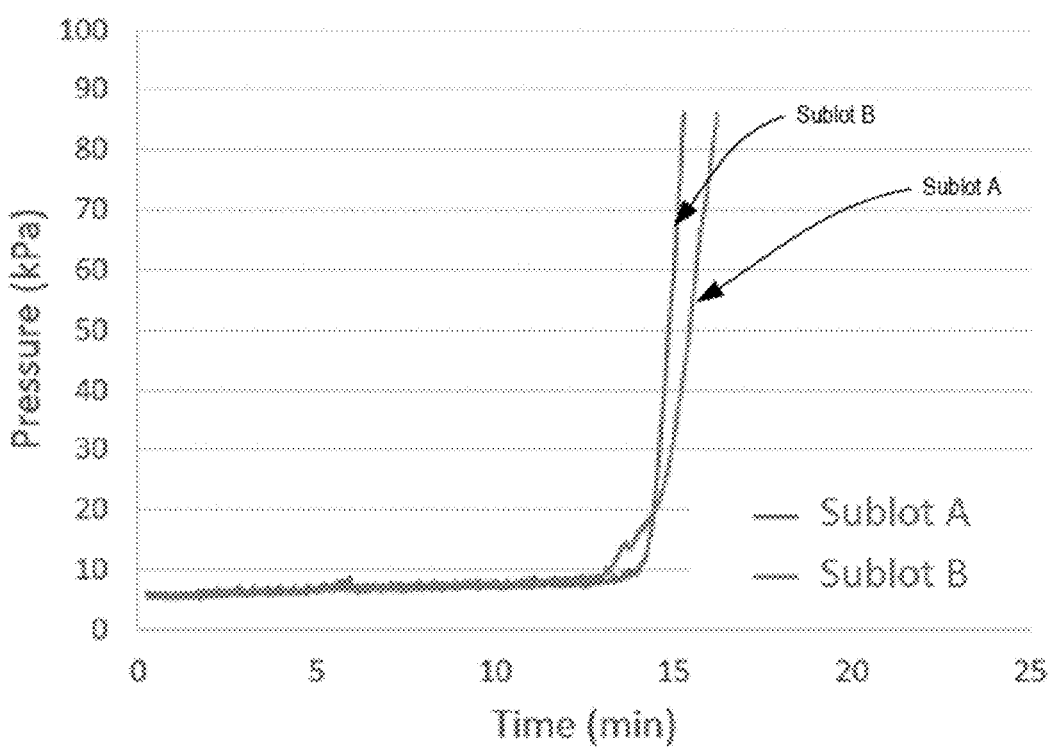
FIG. 22 shows DOX-loaded thrombosomes adhere to collagen and tissue factor coated microchips similar to unloaded thrombosomes.

FIG. 22 shows the batch containing Sublot A with 98 vials of unloaded thrombosomes and Sublot B with 98 vials of DOX-loaded thrombosomes adhere to collagen and tissue factor coated microchips. Specifically, DOX-loaded thrombosomes adhere to collagen and tissue factor coated microchips similar to unloaded thrombosomes. The occlusion times were determined on a T-TAS by measurement of the pressure while suspensions of thrombosomes were flowed over coated surfaces.

Figure 23:
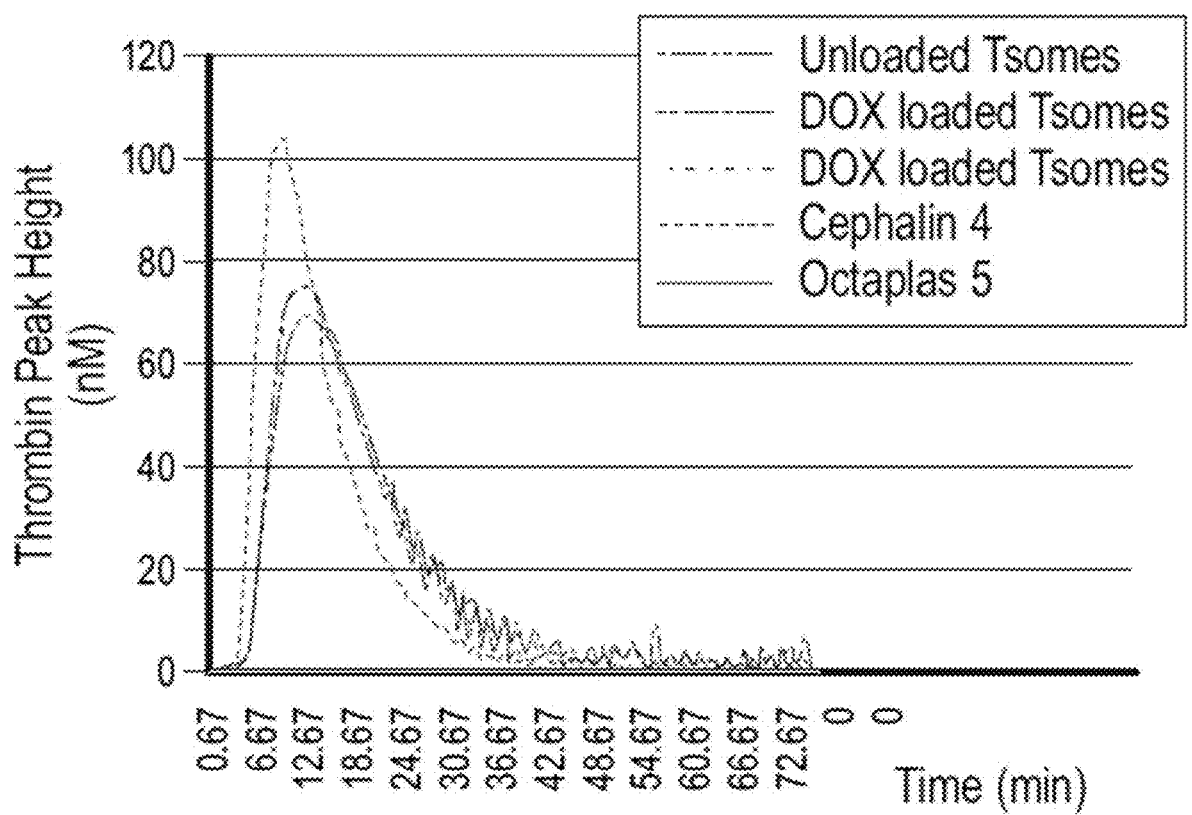
FIG. 23 shows DOX-loaded thrombosomes generate thrombin similar to unloaded thrombosomes.

FIG. 23 shows that DOX-loaded thrombosomes generate thrombin similar to unloaded thrombosomes. Thrombin generation was determined by the measurement of fluorescent signal from a substrate that does not fluoresce until cleavage by thrombin, relative to a control. Cephalin is a positive control to show the maximum possible thrombin generation in the assay, and octaplas is negative control unable to generate thrombin.

Figure 24:
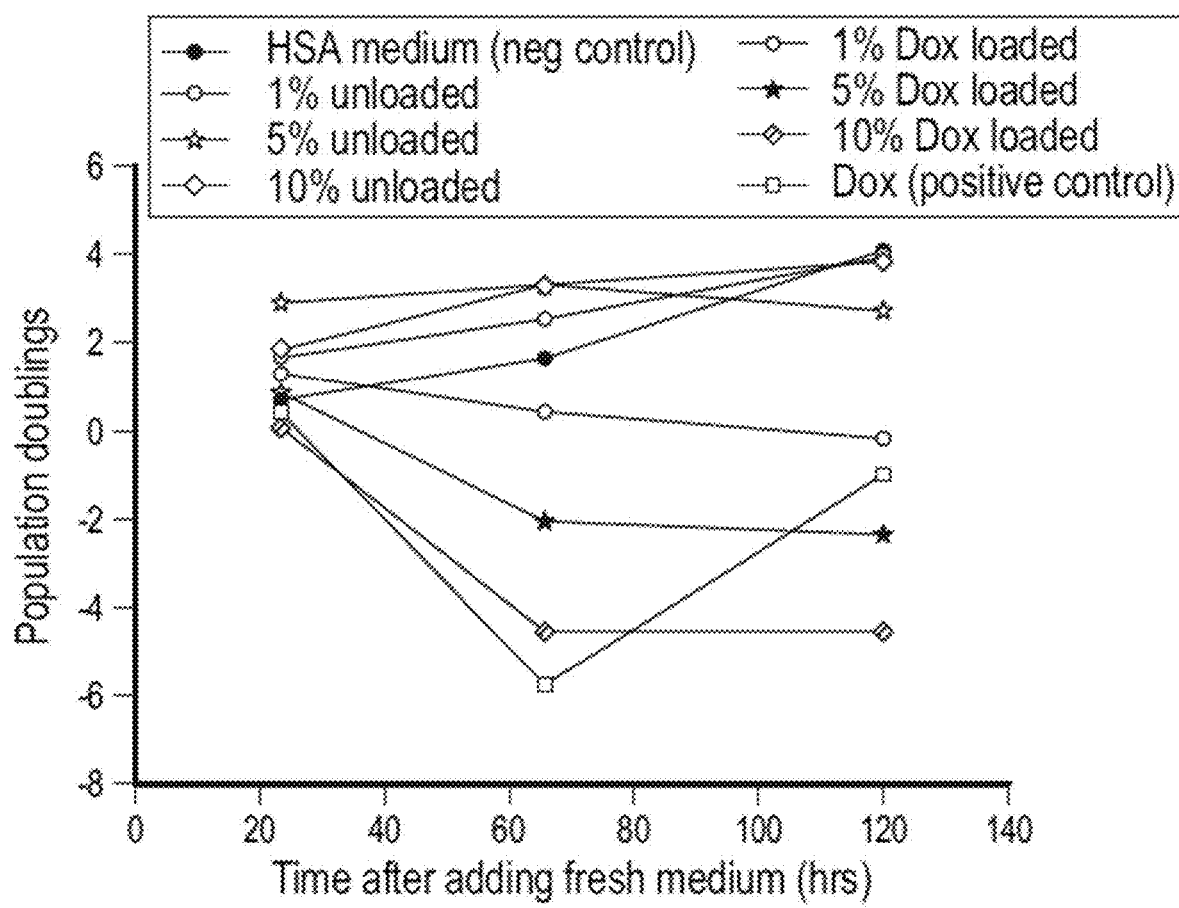
FIG. 24 shows the effect of DOX-loaded thrombosomes on cell growth in a hemangiosarcoma cell model using different amounts of DOX-loaded and unloaded thrombosomes.

FIG. 24 shows that DOX loaded thrombosomes can inhibit cancer cell growth more effectively than DOX alone. Dog hemangiosarcoma cells (DHSA) (Kerafast, DHSA-1426, Cat. # EMN017) were plated at a fixed density in triplicate in 24-well plates and grown overnight. The following day, the loaded and unloaded thrombosomes were rehydrated as described herein and assayed within one hour. The DHSA cells were exposed to medium without thrombosomes (HAS) as a negative control and 1%, 5%, or 10% unloaded thrombosomes and 1%, 5%, or 10% DOX loaded thrombosomes, or free DOX (in medium, 5 uM). The next day after about 24 hours of exposure, the test medium was removed by gentle aspiration, the plates were washed once with fresh medium, and fresh medium was added. The point at which fresh medium was added is considered time zero (FIG. 24). At day 1 (24 hours), 3 (72 hours) and 5 (120 hours), a 24 well plate was harvested. The triplicate wells were pooled and counted using the Nexcelom cell counter Auto 2000 with AO/PI live/dead cell count.

Example 9—Olaparib-Loaded Platelets

Figure 14:
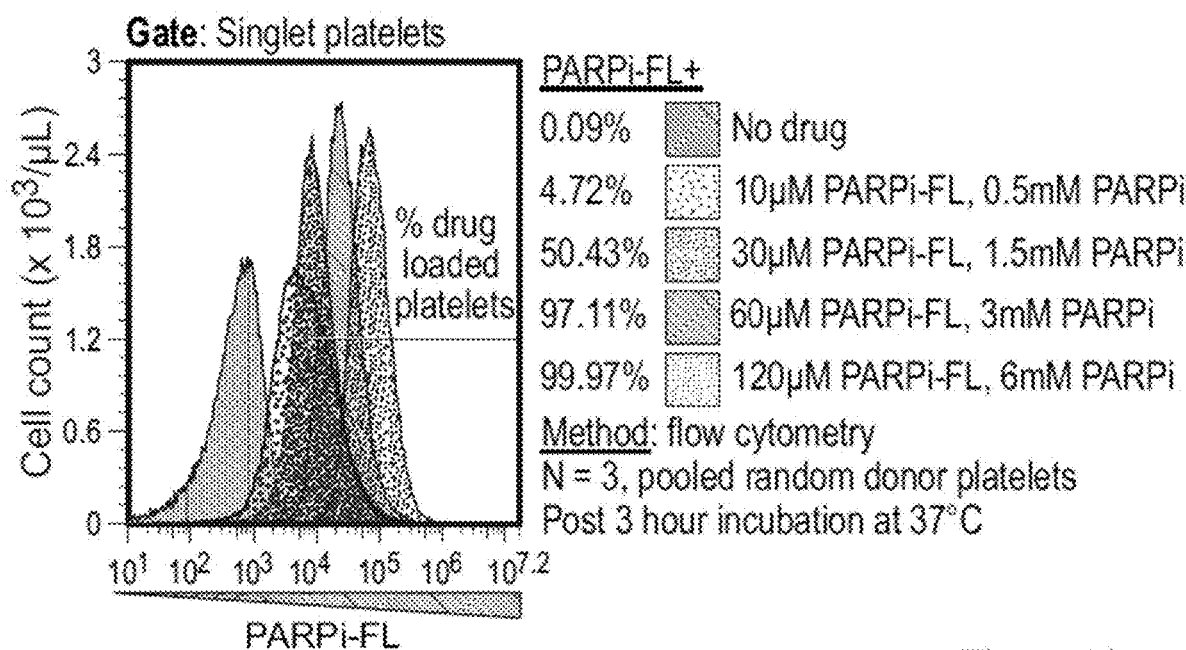
FIG. 14 shows the effect of increasing concentration of a PARP inhibitor (olaparib) on the total number of platelets loaded with PARPi and the amount of PARPi loaded.
Figure 15:
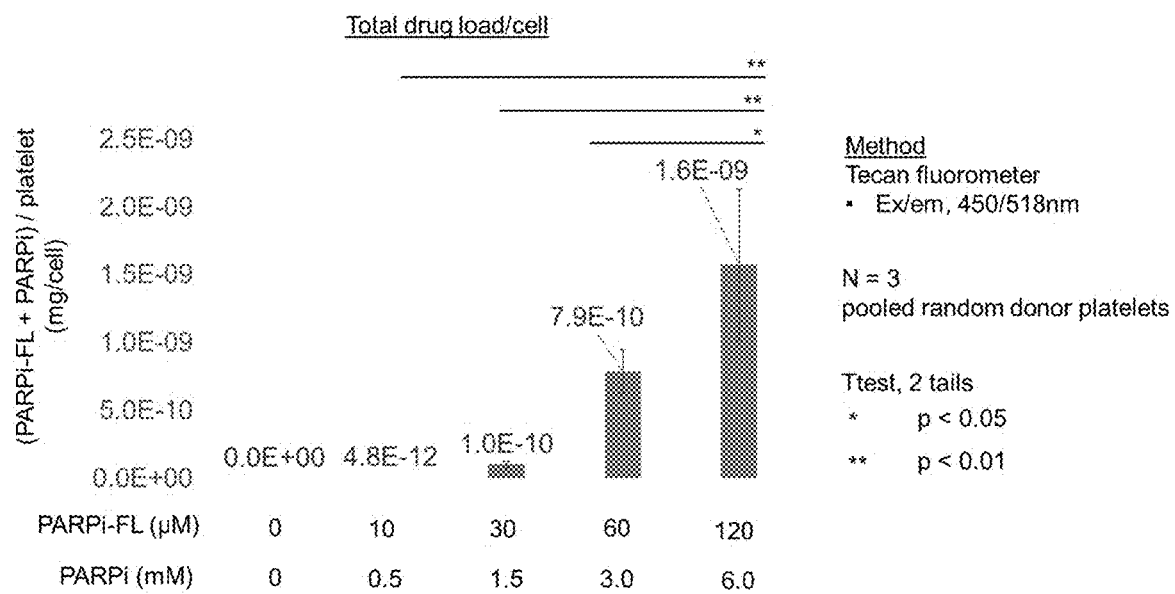
FIG. 15 shows the total drug load (PARP inhibitor) increase following incubation of platelets with increasing concentration of drug.

Poly ADP ribosome polymerase (PARP) inhibitors are drugs used in the treatment of cancer. PARP inhibitors interfere with a cell's ability to repair DNA breaks. Olaparib (also known as AZD-2281, MK-7339, or Lynparza®) is a PARP inhibitor. FIG. 14 shows that Olaparib loads into platelets in a dose-dependent manner. After incubation with increasing total concentrations of PARPi (Olaparib) and a fluorescently labeled PARPi-FL, keeping the ratio at 20:1, platelets were analyzed by flow cytometry. PARPi and PARP-FL were tested at the following concentrations: 10 µM PARPi-FL and 0.5 mM PARPi, 30 µM PARPi-FL and 1.5 mM PARPi, 60 µM PARPi-FL and 3 mM PARPi, and 120 µM PARPi-FL and 6 mM PARPi. The percentage of loaded PARPi-loaded platelets increases with increasing concentrations as measured by the mean fluorescence intensity. FIG. 15 shows the total drug load increase following incubation of cells with increasing concentrations of olparib. The platelets were sonicated and the intracellular fluorescence signal was measured on a plate reader.

Figure 16:
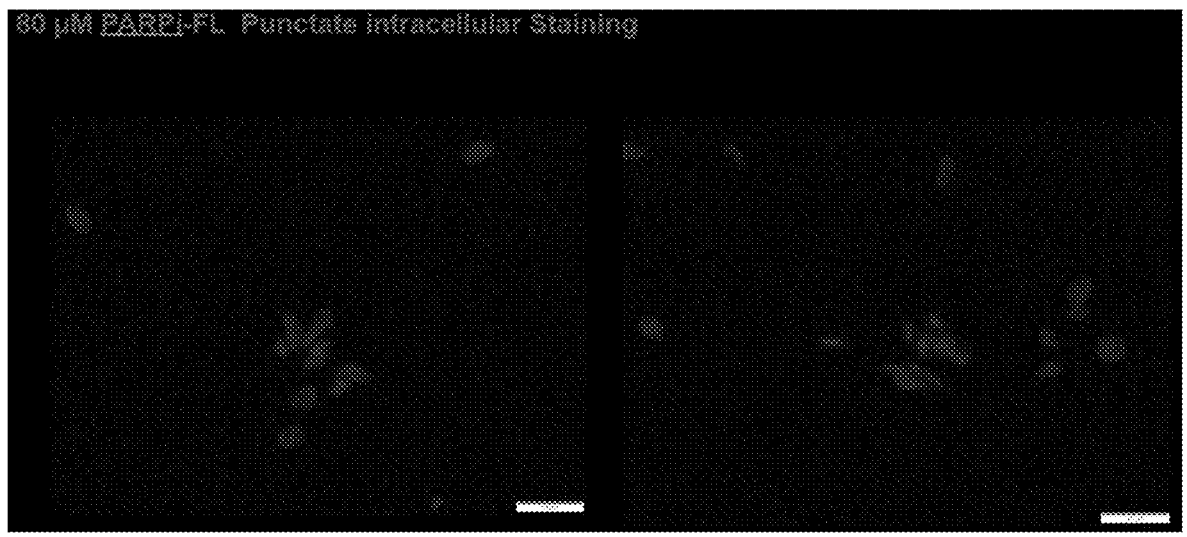
FIG. 16 shows punctate intracellular staining of fluorescently tagged PARP inhibitor (80 μM) after incubation with platelets for 3 h.

Olaparib loaded platelets were verified by loading microscopy. FIG. 16 shows a fluorescence image. Olaparib is localized within platelets. After incubation with 80 µM PARPi-FL at 37° C. for 3 hours, platelets were washed to remove excess fluorophore and fixed on microscope slides at 4° C. overnight. Images were collected on a fluorescence microscope at 100× magnification. These images show the internalization of PARPi into platelets.

Example 10—Paclitaxel-Loaded Platelets

Figure 25A:
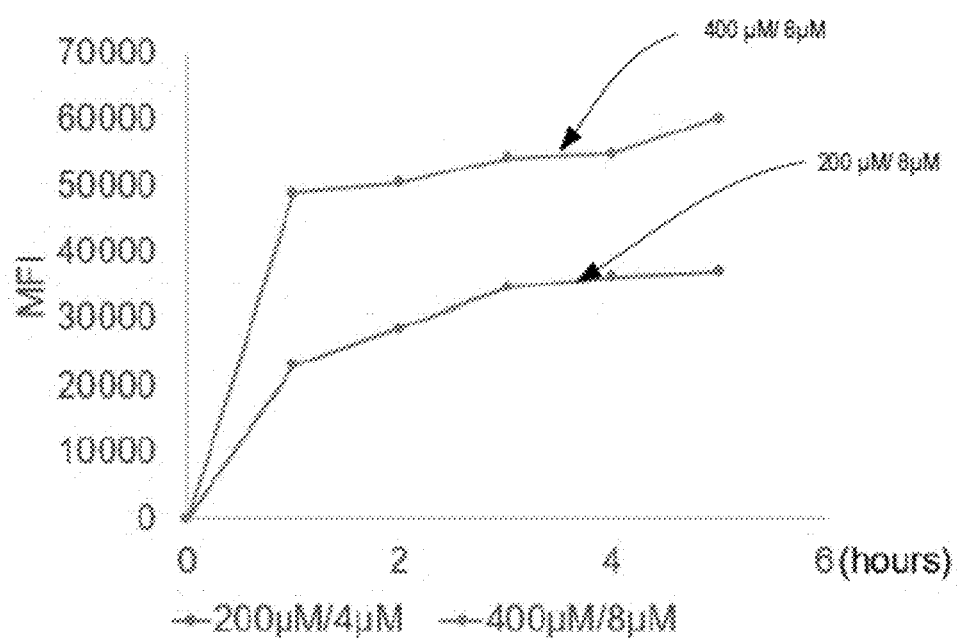
FIG. 25A shows that paclitaxel loads into platelets in a dose-dependent manner as measured by flow cytometry. 200 μM/4 μM is plotted on the bottom and 400 μM/8 μM is plotted on top.
Figure 25B:
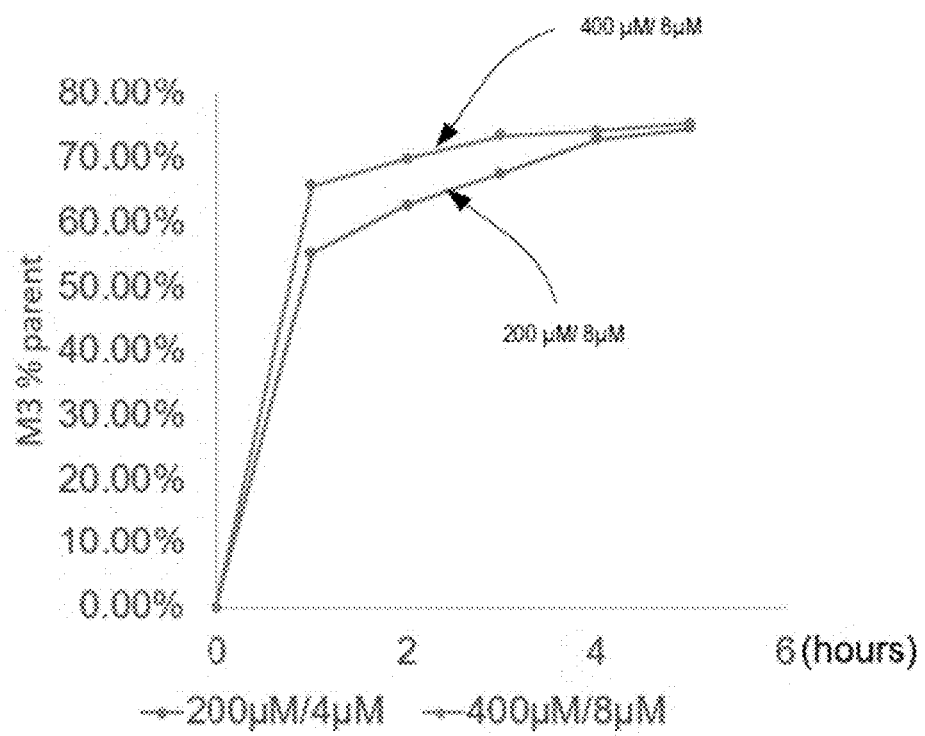
FIG. 25B shows that the percent of platelets loaded with paclitaxel increases with increasing concentration of paclitaxel over time. 200 μM/4 μM is plotted on the bottom and 400 μM/8 μM is plotted on top.

Paclitaxel is a chemotherapy agent that interferes with the normal function of microtubules during cell division. Paclitaxel is loaded into platelets in a dose-dependent manner. FIGS. 25A and B show incubation of platelets with increasing total concentrations of Paclitaxel and fluorescently labeled Paclitaxel-Oregon Green. The platelets were kept at a ratio of 50:1, unlabeled drug to labeled drug. Uptake of paclitaxel was measured by flow cytometry. Measurements were taken at 2, 4, and 6 hours. As time increased from 0 to 6 hours the concentration increased as measured by MFI and percent loaded increases.

Figure 26A:
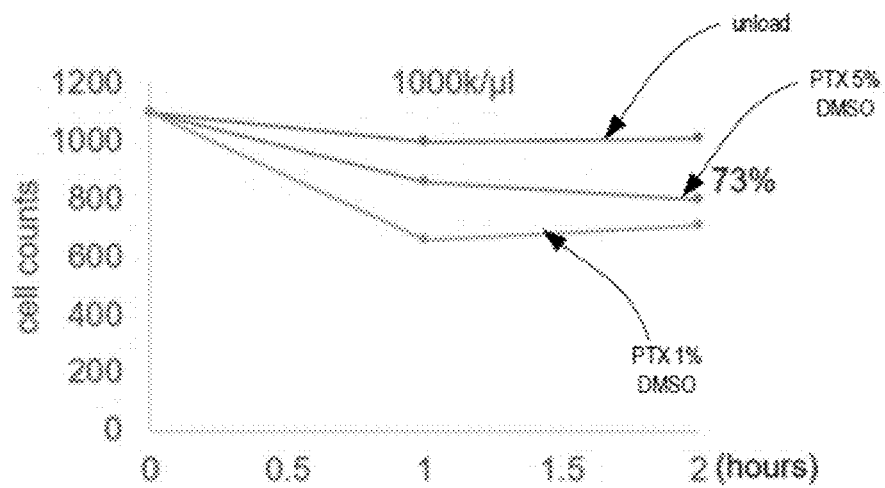
FIGS. 26A-C show that platelet counts remain more stable as a function of a higher initial starting cell count and minimally 50% are retained after loading. PTX in 1% DMSO is plotted on the bottom, PTX in 5% DMSO is plotted in the middle and unloaded is plotted on top.
Figure 26B:
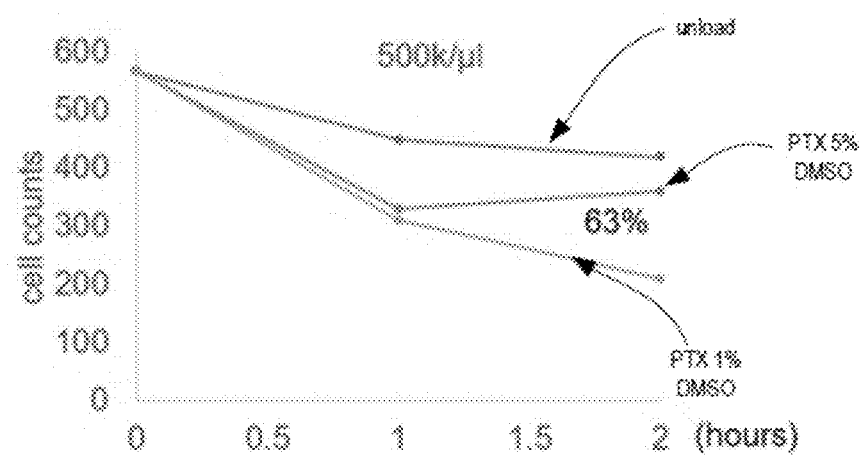
Figure 26C:
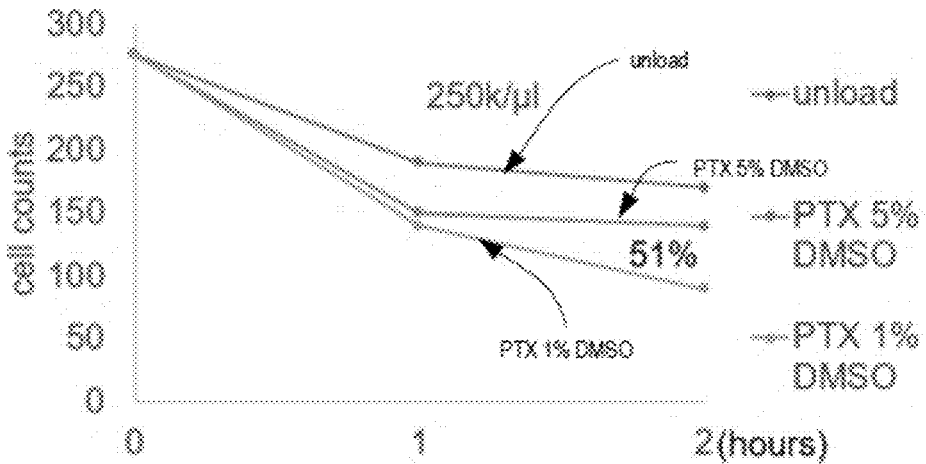

FIG. 26A-C shows the concentration of platelets (measured by count) is determined on an AcT-Diff hematology analyzer during incubation with Paclitaxel. The platelet count is maintained as a function of increasing initial platelet concentration in the presence of paclitaxel, irrespective of the DMSO concentration. Minimally 50% of platelets (platelet count) are retained after loading.

Figure 27:
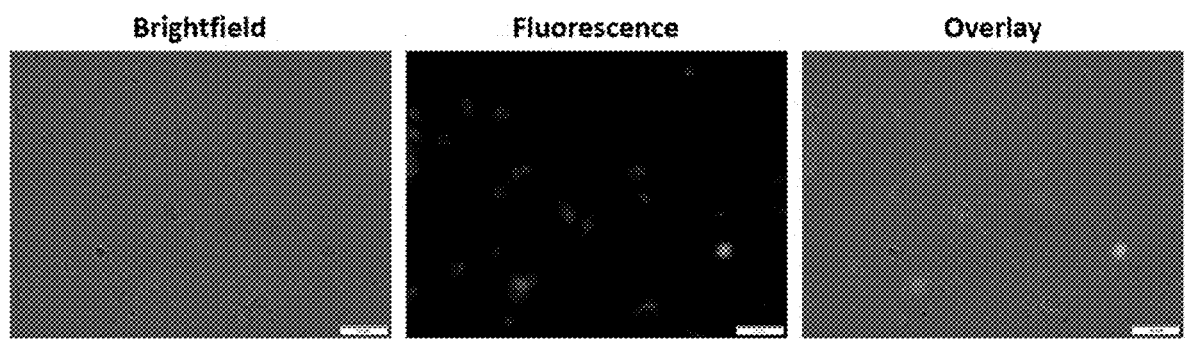
FIG. 27 shows brightfield, fluorescence, and overlaid microscope images of platelets loaded with fluorescently labeled Paclitaxel.

Paclitaxel loaded platelets were verified by loading microscopy. FIG. 27 shows brightfield and fluorescence images, followed by an overlay image. Paclitaxel is localized within platelets. After incubation with 100 μM Paclitaxel-Oregon Green at 37° C. for 2 hours, platelets were washed to remove excess fluorophore and fixed on microscope slides at 4° C. overnight. Images were collected on a fluorescence microscope at 100× magnification. FIG. 27 shows the internalization of Paclitaxel into platelets.

While the embodiments of the invention are amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

1. A method of preparing drug-loaded platelets, comprising:
treating platelets with a drug and with a loading buffer comprising a salt, a base, a loading agent, and optionally at least one organic solvent,
to form the drug-loaded platelets.

2. A method of preparing drug-loaded platelets, comprising:
a) providing platelets; and
b) treating the platelets with a drug and with a loading buffer comprising a salt, a base, a loading agent, and optionally at least one organic solvent
to form the drug-loaded platelets.

3. The method of any one of the preceding embodiments, wherein the platelets are treated with the drug and with the buffer sequentially, in either order.

4. A method of preparing drug-loaded platelets, comprising:
(1) treating platelets with a drug to form a first composition; and
(2) treating the first composition with a buffer comprising a salt, a base, a loading agent, and optionally at least one organic solvent, to form the drug-loaded platelets.

5. A method of preparing drug-loaded platelets, comprising:
(1) treating the platelets with a buffer comprising a salt, a base, a loading agent, and optionally at least one organic solvent to form a first composition; and
(2) treating the first composition with a drug, to form the drug-loaded platelets.

6. The method of embodiment 1 or 2, wherein the platelets are treated with the drug and with the buffer concurrently.

7. A method of preparing drug-loaded platelets, comprising:
treating the platelets with a drug in the presence of a buffer comprising a salt, a base, a loading agent, and optionally at least one organic solvent to form the drug-loaded platelets.

8. The method of any one of the preceding embodiments, wherein the platelets are pooled from a plurality of donors prior to a treating step.

9. A method of preparing drug-loaded platelets comprising
A) pooling platelets from a plurality of donors; and
B) treating the platelets from step (A) with a drug and with a loading buffer comprising a salt, a base, a loading agent, and optionally at least one organic solvent, to form the drug-loaded platelets.

10. A method of preparing drug-loaded platelets comprising
A) pooling platelets from a plurality of donors; and
B)
(1) treating the platelets from step (A) with a drug to form a first composition; and
(2) treating the first composition with a buffer comprising a salt, a base, a loading agent, and optionally at least one organic solvent, to form the drug-loaded platelets.

11. A method of preparing drug-loaded platelets comprising
A) pooling platelets from a plurality of donors; and
B)
(1) treating the platelets from step (A) with a buffer comprising a salt, a base, a loading agent, and optionally at least one organic solvent, to form a first composition; and
(2) treating the first composition with a drug to form the drug-loaded platelets.

12. A method of preparing drug-loaded platelets comprising
A) pooling platelets from a plurality of donors; and
B) treating the platelets with a drug in the presence of a buffer comprising a salt, a base, a loading agent, and optionally at least one organic solvent, to form the drug-loaded platelets.

13. The method of any one of the preceding embodiments, wherein the loading agent is a monosaccharide or a disaccharide.

14. The method of any one of the preceding embodiments, wherein the loading agent is sucrose, maltose, trehalose, glucose, mannose, or xylose.

15. The method of any one of the preceding embodiments, wherein the platelets are isolated prior to a treating step.

16. The method of any one of the preceding embodiments, wherein the platelets are loaded with the drug in a period of time of 5 minutes to 48 hours.

17. The method of any one of the preceding embodiments, wherein the concentration of drug in the drug-loaded platelets is from about 1 nM to about 100 mM.

18. The method of any one of the preceding embodiments, wherein the one or more organic solvents selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof.

19. The method of any one of the preceding embodiments, further comprising cold storing, cryopreserving, freeze-drying, thawing, rehydrating, and combinations thereof the drug-loaded platelets.

20. The method of embodiment 19, wherein the drying step comprises freeze-drying the drug-loaded platelets.

21. The method of embodiment 19 or 20, further comprising rehydrating the drug-loaded platelets obtained from the drying step.

22. Drug-loaded platelets prepared by the method of any one of the preceding embodiments.

23. Rehydrated drug-loaded platelets prepared by a method comprising rehydrating the drug-loaded platelets of c embodiment 22.

24. The method of any one of the preceding embodiments, wherein the drug is modified with an imaging agent.

25. The method of embodiment 24, wherein the drug is modified with the imaging agent prior to treating platelets with the drug.

26. The method of any one of the preceding embodiments, wherein the platelets are further treated with an imaging agent, wherein the drug-loaded platelets are loaded with the imaging agent.

27. The method of any one of the preceding embodiments, wherein the method does not comprise treating the platelets with an organic solvent.

28. The method of any one of embodiments 4, 5, 10 or 11, wherein the method does not comprise treating the first composition with an organic solvent.

29. The method of any one of the preceding embodiments, wherein the method comprises treating the platelets with Prostaglandin E1 (PGE1) or Prostacyclin.

30. The method of any one of embodiments 1 to 28, wherein the method does not comprise treating the platelets with Prostaglandin E1 (PGE1) or Prostacyclin.

31. The method of any one of the preceding embodiments, wherein the method comprises treating the platelets with a chelating agent such as EGTA.

32. The method of any one of embodiments 1 to 30, wherein the method does not comprise treating the platelets with a chelating agent such as EGTA.

33. The method of any one of embodiments 1 to 29, wherein the method comprises treating the first composition with Prostaglandin E1 (PGE1) or Prostacyclin.

34. The method of any one of embodiments 1 to 28 or 30, wherein the method does not comprise treating the first composition with Prostaglandin E1 (PGE1) or Prostacyclin.

35. The method of any one of embodiments 1 to 31, 33 or 34, wherein the method comprises treating the first composition with a chelating agent such as EGTA.

36. The method of any one of embodiments 1 to 30 or 32 to 34, wherein the method does not comprise treating the first composition with a chelating agent such as EGTA.

37. The method of any one of the preceding embodiments, wherein the method further comprises treating the drug-loaded platelets with an anti-aggregation agent.

38. The method of embodiment 37, wherein the anti-aggregation agent is a GPIIb/IIIa inhibitor.

39. The method of embodiment 38, wherein the GPIIb/IIIa inhibitor is GR144053.

40. The method of embodiment 39, wherein GR144053 is present in a concentration of at least 1.2 µM.

41. The method of any one of embodiments 38-41, wherein the platelets are treated with the anti-aggregation agent before being treated with the drug.

42. The method of any one of embodiments 38-41, wherein the platelets are treated with the anti-aggregation agent concurrently with the drug.

43. The method of any one of the preceding claims, wherein the drug is a small molecule, a protein, an oligopeptide, an aptamer, and combinations thereof.

44. The method of any one of the preceding embodiments, wherein the drug is a drug for the treatment of cancer.

45. The method of embodiment 44, wherein the cancer comprises hemangiosarcoma.

46. The method of embodiments 44-45, wherein the drug for the treatment of cancer is doxorubicin.

47. The method of embodiments 45-46, wherein the drug for the treatment of hemangiosarcoma is doxorubicin.

48. The method of embodiment 44, wherein the drug for the treatment of cancer is paclitaxel.

49. The method of embodiment 44, wherein the drug for the treatment of cancer is a PARP inhibitor.

50. The method of embodiment 49, wherein the PARP inhibitor is olaparib.

The invention claimed is:

1. A method of preparing chemotherapy drug-loaded, freeze-dried platelet derivatives, comprising:
   a) providing platelets;
   b) treating the platelets with a rubicin selected from the group consisting of daunorubicin, doxorubicin, epirubicin, idarubicin, and valrubicin in the presence of a loading buffer comprising a salt, a base, and a loading agent comprising trehalose in an amount of 10 mM to 500 mM to form chemotherapy drug-loaded platelets, wherein the chemotherapy drug-loaded platelets comprise 1 nM to 100 mM of the rubicin; and
   c) lyophilizing the chemotherapy drug-loaded platelets to form chemotherapy drug-loaded, freeze-dried platelet derivatives
   having the property of retaining at least 20% of the rubicin upon rehydration, having less than 10% crosslinking of platelet membranes via proteins and/or lipids present on the platelet membranes, and having the property of inhibiting cancer cell growth more effectively than the rubicin alone.

2. The method of claim 1, wherein the loading buffer further comprises a monosaccharide selected from the group consisting of glucose, mannose, and xylose.

3. The method of claim 2, wherein the treating step comprises treating the platelets with the rubicin in the presence of at least one organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof.

4. The method of claim 3, wherein the at least one organic solvent is ethanol in a concentration range of 0.3% to 3% (v/v), and wherein the chemotherapy drug-loaded, freeze-dried platelet derivatives have less than 4% crosslinking of platelet membranes via proteins and/or lipids present on the platelet membranes.

5. The method of claim 2, wherein the trehalose is at a concentration of 50 mM to 500 mM, wherein the treating step comprises treating the platelets with the rubicin in the presence of at least one organic solvent, the lyophilizing is done in the presence of the loading buffer further comprising polysucrose in an amount of 3% to 10% (w/v), and the chemotherapy drug-loaded, freeze-dried platelet derivatives have the property of retaining at least 30% of the loaded drug upon rehydration.

6. The method of claim 5, wherein the chemotherapy drug-loaded, freeze-dried platelet derivatives have less than 6% crosslinking of platelet membranes via proteins and/or lipids present on the membranes.

7. The method of claim 6, wherein the at least one organic solvent comprises ethanol having a concentration in the range of 0.1% to 5.0% (v/v).

8. The method of claim 1, wherein the rubicin is doxorubicin.

9. The method of claim 8, wherein the doxorubicin-loaded freeze-dried platelet derivatives have the property of inhibiting cancer cell growth more effectively than doxorubicin alone.

10. The method of claim 1, wherein the trehalose is in a concentration of 50 mM to 500 mM, wherein the chemotherapy drug-loaded, freeze-dried platelet derivatives have the property of retaining at least 30% of the loaded drug upon rehydration, and wherein the chemotherapy drug-loaded, freeze-dried platelet derivatives have less than 2% crosslinking of platelet membranes via proteins and/or lipids present on the platelet membranes.

11. The method of claim 10, wherein the method further comprises rehydrating the chemotherapy drug-loaded freeze-dried platelet derivatives to form rehydrated chemotherapy drug-loaded platelet derivatives.

12. The method of claim 5, wherein the rubicin is doxorubicin.

13. The method of claim 10, wherein the treating is done further in the presence of at least one organic solvent that comprises ethanol a concentration in the range of 0.1% to 5.0% (v/v), and wherein the lyophilizing is done in the presence of polysucrose in the range of 3% to 10% (w/v).

14. The method of claim 1, wherein the lyophilizing is done in the presence of the loading buffer further comprising polysucrose in an amount of 3% to 10% (w/v).

15. The method of claim 1, wherein the treating the platelets is done for a time of 10 minutes to 6 hours at a temperature of 20° C. to 42° C.

\* \* \* \* \*